(12) United States Patent
Chapoux et al.

(10) Patent No.: US 9,624,206 B2
(45) Date of Patent: Apr. 18, 2017

(54) ANTIBACTERIAL 1H-INDAZOLE AND 1H-INDOLE DERIVATIVES

(71) Applicant: ACTELION PHARMACEUTICALS LTD, Allschwil (CH)

(72) Inventors: Gaelle Chapoux, Allschwil (CH); Jean-Christophe Gauvin, Allschwil (CH); Christian Hubschwerlen, Durmenach (CH); Azely Mirre, Allschwil (CH); Etienne Ochala, Blotzheim (CH); Jean-Luc Specklin, Allschwil (CH); Jean-Philippe Surivet, Allschwil (CH)

(73) Assignee: ACTELION PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/106,790

(22) PCT Filed: Dec. 18, 2014

(86) PCT No.: PCT/EP2014/078384
§ 371 (c)(1),
(2) Date: Jun. 20, 2016

(87) PCT Pub. No.: WO2015/091741
PCT Pub. Date: Jun. 25, 2015

(65) Prior Publication Data
US 2017/0029411 A1    Feb. 2, 2017

(30) Foreign Application Priority Data
Dec. 19, 2013  (EP) ................ 13198338

(51) Int. Cl.
*C07D 409/06*   (2006.01)
*C07D 231/56*   (2006.01)
(Continued)

(52) U.S. Cl.
CPC ......... *C07D 409/06* (2013.01); *C07D 209/08* (2013.01); *C07D 231/56* (2013.01);
(Continued)

(58) Field of Classification Search
None
See application file for complete search history.

(56) References Cited

U.S. PATENT DOCUMENTS 8,809,333 B2 * 8/2014 Brown .................. C07D 231/12
514/249

FOREIGN PATENT DOCUMENTS

WO  WO 03/077914 A1   9/2003
WO  WO 2005/103032 A2  11/2005
(Continued)

OTHER PUBLICATIONS

U.S. Appl. No. 15/123,184, filed Sep. 1, 2016.
(Continued)

*Primary Examiner* — Kamal Saeed
(74) *Attorney, Agent, or Firm* — Arent Fox LLP

(57) ABSTRACT

The invention relates to antibacterial compounds of formula I

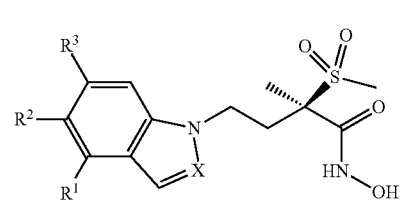

wherein X is N or CH; $R^1$ is H or halogen; $R^2$ is alkynyloxy or the group M; $R^3$ is H or halogen; M is one of the groups $M^A$ and $M^B$ represented below

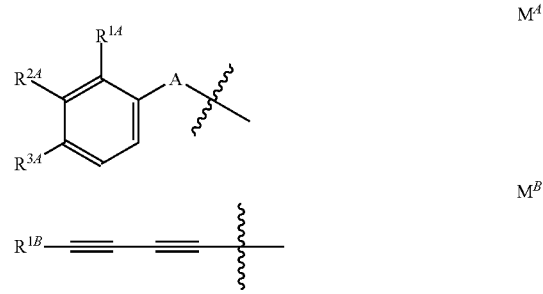

wherein A is a bond, $CH_2CH_2$, CH=CH or C≡C; $R^{1A}$ is H or halogen; $R^{2A}$ is H, alkoxy or halogen; $R^{3A}$ is H, alkoxy, hydroxyalkoxy, alkoxyalkoxy, thioalkoxy, trifluoromethoxy, amino, hydroxyalkyl, 2-hydroxyacetamido, 1-aminocyclopropyl, 1-hydroxymethyl-cycloprop-1-yl, 1-((phosphonooxy)methyl)cyclopropyl, 1-(((dimethylglycyl)oxy)methyl)cyclopropyl, trans-2-hydroxymethyl-cycloprop-1-yl, 1,2-dihydroxyethyl, 3-hydroxyoxetan-3-yl, 3-(hydroxyalkyl)oxetan-3-yl, 3-aminooxetan-3-yl, 3-hydroxythietan-3-yl, morpholin-4-ylalkoxy, morpholin-4-ylalkyl, oxazol-2-yl or [1,2,3]triazol-2-yl; and $R^{1B}$ is hydroxyalkyl, dihydroxyalkyl, aminoalkyl, 1-hydroxymethyl-cycloprop-1-yl, 1-aminomethyl-cycloprop-1-yl, trans-2-hydroxymethyl-cycloprop-1-yl, 3-hydroxyoxetan-3-yl, 3-hydroxythietan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl or 3-hydroxymethylbicyclo[1,1,1]pentan-1-yl; and salts thereof.

15 Claims, No Drawings

(51) Int. Cl.
*C07D 209/08* (2006.01)
*C07D 405/06* (2006.01)
*C07D 403/12* (2006.01)
*C07D 403/06* (2006.01)

(52) U.S. Cl.
CPC ......... *C07D 403/06* (2013.01); *C07D 403/12* (2013.01); *C07D 405/06* (2013.01)

(56) References Cited

FOREIGN PATENT DOCUMENTS

| WO | WO 2006/044860 A2 | 4/2006 |
|---|---|---|
| WO | WO 2006/099972 A1 | 9/2006 |
| WO | WO 2008/154642 A2 | 12/2008 |
| WO | WO 2010/135536 A2 | 11/2010 |
| WO | WO 2011/045703 A2 | 4/2011 |
| WO | WO 2011/073845 A1 | 6/2011 |
| WO | WO 2012/037410 A2 | 3/2012 |
| WO | WO 2012/093809 A2 | 7/2012 |
| WO | WO 2012/120397 A1 | 9/2012 |
| WO | WO 2012/137094 A1 | 10/2012 |
| WO | WO 2012/137099 A1 | 10/2012 |
| WO | WO 2012/154204 A1 | 11/2012 |
| WO | WO 2013/170030 A1 | 11/2013 |
| WO | WO 2013/170165 A1 | 11/2013 |
| WO | WO 2015/036964 A1 | 3/2015 |
| WO | WO 2015/132228 A1 | 9/2015 |
| WO | WO 2015/173329 A1 | 11/2015 |

OTHER PUBLICATIONS

"Methods for Dilution Antimicrobial Susceptibility Tests for Bacteria That Grow Aerobically," Approved standard 7th ed., Clinical and Laboratory Standards Institute (CLSI) Document M7-A7, USA (2006).
Bellina et al., "Palladium Catalysts for the Suzuki Cross-Coupling Reaction: An Overview of Recent Advances," Synthesis (2004), pp. 2419-2440.
Benz, "Synthesis of Amides and Related Compounds," Comprehensive Organic Synthesis, New York (1991), pp. 381-417.
Chodkiewicz and Cadiot, C.R. Hebd. Seances Acad. Sci. (1955), 241, pp. 1055-1057.
Fu, "The Development of Versatile Methods for Palladium-Catalyzed Coupling Reactions of Aryl Electrophiles through the Use of P(t-BU)3 and PCy3 as Ligands," Acc. Chem. Res. (2008), 41, pp. 1555-1564.
J.P. Sanford et al., "The Sanford Guide to Antimicrobial Therapy," 26th Edition, (Antimicrobial Therapy, Inc., 1996), pp. 1-4.
Kantchev et al., "Pd-N-Heterocyclic Carbene (NHC) Catalysts for Cross-Coupling Reactions," Aldrichimica Acta (2006), 39, pp. 97-111.
Marmer et al., "The Preparation and Reactions of Novel O-Acylhydroxylamines," J. Org. Chem. (1972), 37, pp. 3520-3523.
Mauger et al., "Synthetic Applications of Buchwald's Phosphines in Palladium-Catalyzed Aromatic-Bond-Forming Reactions," Aldrichimica Acta (2006), 39, pp. 17-24.
McAllister et al., "Heterocyclic methylsulfone hydroxamic acid LpxC inhibitors as Gram-negative antibacterial agents," Biooragnic & Medicinal Chemistry Letters, 22, 2012, pp. 6832-6838.
Miyaura et al., "Palladium-Catalyzed Cross-Coupling Reactions of Organoboron Compounds," Chem. Rev. (1995), 95, pp. 2457-2483.
Perner et al., "Synthesis and biological evaluation of 6,7-disubstituted 4-aminopyrido[2,3-d]pyrimidines as adenosine kinas inhibitors," Biorg. Med. Chem. Lett. (2005), 15, pp. 2803-2807.
R.C. Larock, "Comprehensive Organic Transformations, A guide to Functional Group Preparations," 2nd Edition (1999), Section nitriles, carboxylic acids and derivatives, pp. 1941-1949.
Reddy et al., "Mild and efficient oxy-iodination of alkynes and phenols with potassium iodide and tert-butyl hydroperoxide," Tetrahedron Letters, (2010), 51, pp. 2170-2173.
Remington, The Science and Practice of Pharmacy, 21st Edition (2005), Part 5, "Pharmaceutical Manufacturing," pp. 1-5.
Sleveland et al., "Synthesis of Phenylboronic Acids in Continuous Flow by Means of a Multijet Oscillating Disc Reactor System Operating at Cryogenic Temperatures," Organic Process Research & Development (2012), 16, pp. 1121-1130.
Sonogashira K. In Metal-Catalyzed Reactions, Diederich, F., Stang, P.J., Eds.; Wiley-VCH, New York (1998), pp. 1-27.
Stahl et al., "Handbook of Pharmaceutical Salts. Properties, Selection and Use," 2008, pp. 1-24.
T.W. Greene and P.G.M. Wuts, Protecting Groups in Organic Synthesis, 3rd Ed (1999), pp. 1-3.
T.W. Greene and P.G.M. Wuts, Protection for the Carboxyl Group, Protecting Groups in Organic Synthesis, 3rd. (1999), pp. 361-441.
T.W. Greene, P.G.M. Wuts, Protecting Groups in Organic Synthesis, 3rd Ed. (1999), pp. 23-147.
Tsuda et al., "Application of Modified Mosher's Method for Primary Alcohols with a Methyl Group at C2 Position," Chem. Pharm. Bull. (2003), 51, pp. 448-451.
U.S. Appl. No. 15/021,649, filed Mar. 11, 2016.
Wouters et al., "Pharmaceutical Salts and Co-crystals," (2012) pp. 1-10.
U.S. Appl. No. 15/311,758, filed Nov. 16, 2016.

* cited by examiner

ANTIBACTERIAL 1H-INDAZOLE AND 1H-INDOLE DERIVATIVES

CROSS REFERENCE TO RELATED APPLICATION

This application is a 35 U.S.C. 371 National Phase PCT Application No. PCT/EP2014/078384 filed Dec. 18, 2014, which claims priority to European Patent Application No. 13198338.9 filed Dec. 19, 2013, the disclosure of these prior applications are hereby incorporated in their entirety by reference.

The present invention concerns antibacterial 1H-indazole and 1H-substituted indole derivatives, pharmaceutical compositions containing them and uses of these compounds in the manufacture of medicaments for the treatment of bacterial infections. These compounds are useful antimicrobial agents effective against a variety of human and veterinary pathogens, especially Gram-negative aerobic and anaerobic bacteria. The compounds of the present invention can optionally be employed in combination, either sequentially or simultaneously, with one or more therapeutic agents effective against bacterial infections.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriaceae such as *Klebsiella pneumoniae, Acinetobacter baumannii* and *Pseudomonas aeruginosa*, major sources of infections, are becoming multi-drug resistant and therefore difficult if not impossible to treat. This is particularly the case for Gram-negative organisms where the situation is getting worrisome since no novel agents have been approved for decades and the development pipeline looks empty.

Therefore, there is an important medical need for new antibacterial compounds addressing Gram-negative resistant bacteria, in particular third generation cephalosporins- and carbapenem-resistant *Klebsiella pneumoniae* and multi-drug-resistant *Pseudomonas aeruginosa* and *Acinetobacter baumannii*. One way to tackle the problem of cross resistance to established classes of antibiotics is to inhibit a new target. In this respect, LpxC, which is an essential enzyme in the biosynthesis of lipopolysaccharides (a major constituent of the outer membrane of Gram-negative bacteria), has received some attention and several patent applications relating to LpxC inhibitors have been published recently.

For example, WO 2011/045703 describes antibacterial compounds of formula (A1)

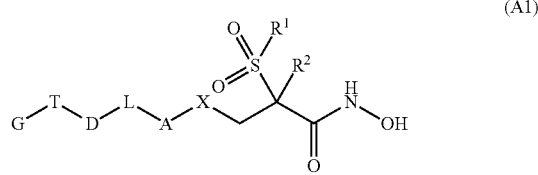

(A1)

wherein $R^1$ is $(C_1-C_3)$alkyl; $R^2$ is H or $(C_1-C_3)$alkyl; X is $CH_2$, O, NH, S or $SO_2$; A is an optionally substituted phenyl or a 6-membered heteroaryl group; L is absent or is S, SH, OH, —$(CH_2)_p$—O—$(CH_2)_n$—, —$(CH_2)_p$—O—$(CH_2)_z$—O—$(CH_2)_n$—, —S—$(CH_2)_z$— or —$(CH_2)_z$—S—; D is absent or is an optionally substituted group containing a carbocyclic or heterocyclic component with optionally a $(C_1-C_3)$alkyl chain appended; T is absent or is —$(CH_2)_z$—, —$(CH_2)_z$—O— or —O—$(CH_2)_p$—C(O)—$(CH_2)_n$—; G is absent or is an optionally substituted carbocyclic or heterocyclic group; and n and p are integers each ranging from 0 to 3 and z is an integer ranging from 1 to 3.

WO 2011/073845 and WO 2012/120397 describe antibacterial compounds with a structural formula similar to formula (A1), whereby the group corresponding to the group A of formula (A1) however respectively represents a pyridin-2-one or a fluoropyridin-2-one residue.

WO 2012/137094 describes antibacterial compounds of formulae (A2) and (A3)

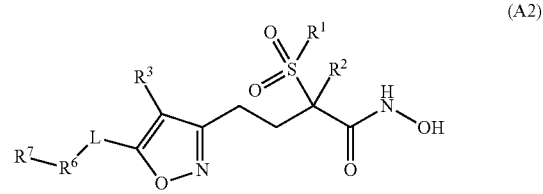

(A2)

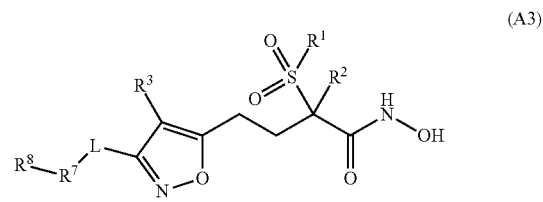

(A3)

wherein $R^1$ is $(C_1-C_3)$alkyl; $R^2$ is H or $(C_1-C_3)$alkyl; $R^3$ is H, $(C_1-C_3)$alkoxy, $(C_1-C_3)$alkyl, cyano, $(C_1-C_3)$haloalkoxy, $(C_1-C_3)$haloalkyl, halogen or hydroxy; L is a bond, —$(CH_2)_n$—, —$(CH_2)_nO(CH_2)_p$—, —$(CH_2)_nNR^4(CH_2)_p$—, —$(CH_2)_nSO_2NR^4(CH_2)_p$—, —$(CH_2)_nCONR^4(CH_2)_p$— or —$(CH_2)_nNR^4CO(CH_2)$—; $R^4$ and $R^5$ are independently H, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl or formyl; n is 0, 1, 2, 3 or 4; p is 0, 1, 2, 3 or 4; $R^6$ is $(C_1-C_6)$alkoxy$(C_1-C_6)$alkyl, $(C_1-C_6)$alkoxycarbonyl, $(C_1-C_6)$alkyl-$NR^4$—$(C_1-C_6)$alkyl, $(C_1-C_6)$alkylthio$(C_1-C_6)$alkyl, $(C_1-C_6)$alkylthiocarbonyl, $(C_6-C_{12})$aryl, $(C_6-C_{12})$aryloxy, $(C_6-C_{12})$arylthio, $(C_6-C_{12})$aryl-$NR^4$—, $(C_3-C_8)$cycloalkyl, $(C_3-C_8)$cycloalkyloxy, $(C_3-C_8)$cycloalkylthio, $(C_5-C_8)$cycloalkyl-$NR^4$—, $(C_5-C_{12})$heteroaryl, $(C_5-C_{12})$heteroaryloxy, $(C_5-C_{12})$heteroarylthio, $(C_5-C_2)$heteroaryl-$NR^4$—, $(C_3-C_{13})$heterocyclyl, $(C_3-C_{13})$heterocyclyloxy, $(C_3-C_{13})$heterocyclylthio, $(C_3-C_{13})$heterocycle-$NR^4$—, hydroxy$(C_1-C_{10})$alkyl, mercapto$(C_1-C_6)$alkyl, $(NR^4R^5)$alkyl, or $(NR^4R^5)$carbonyl; and $R^7$ is absent or is $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocyclyl or $(C_3-C_{13})$heterocyclyl$(C_1-C_6)$alkyl.

WO 2012/137099 describes antibacterial compounds of formula (A4)

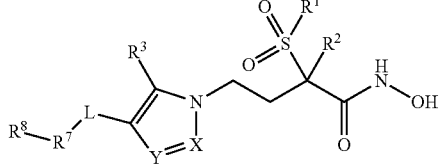
(A4)

wherein $R^1$ is $(C_1-C_3)$alkyl; $R^2$ is H or $(C_1-C_3)$alkyl; $R^3$ is H or $(C_1-C_3)$alkyl; X is N or $CR^4$; Y is N or $CR^4$; $R^4$ is H or $(C_1-C_3)$alkyl; L is a bond, $(C_2-C_6)$alkenylene, $(C_1-C_6)$alkylene, $(C_2-C_6)$alkynylene, —$(CH_2)_nO(CH_2)_p$—, —$(CH_2)_nS(CH_2)_p$—, —$(CH_2)_nNR^5(CH_2)_p$—, —$(CH_2)_nSO_2NR^5(CH_2)_p$—, —$(CH_2)_nNR^5SO_2(CH_2)_p$—, —$(CH_2)_nCONR^5(CH_2)_p$— or —$(CH_2)_nNR^5CO(CH_2)_p$—; $R^5$ and $R^6$ are independently H, $(C_1-C_6)$alkyl, $(C_1-C_6)$alkylcarbonyl, $(C_3-C_8)$cycloalkyl, $(C_3-C_8)$cycloalkyl$(C_1-C_6)$alkyl or formyl; n is 0, 1, 2, 3 or 4; p is 0, 1, 2, 3 or 4; $R^7$ is $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkylcarbonyl, $(C_1-C_6)$alkyl-$NR^5$—$(C_1-C_6)$alkyl, $(C_1-C_6)$alkylthio, $(C_1-C_6)$alkylthio$(C_1-C_6)$alkyl, $(C_1-C_6)$alkylthiocarbonyl, $(C_2-C_6)$alkynyl, $(C_6-C_{12})$aryl, $(C_6-C_{12})$aryloxy, $(C_6-C_{12})$arylthio, $(C_6-C_{12})$aryl-$NR^5$—, cyano, cyano$(C_1-C_6)$alkyl, $(C_5-C_8)$cycloalkenyl, $(C_3-C_8)$cycloalkyl, $(C_3-C_8)$cycloalkyloxy, $(C_3-C_8)$cycloalkylthio, $(C_5-C_8)$cycloalkyl-$NR^5$— $(C_5-C_{12})$heteroaryl, $(C_5-C_{12})$heteroaryloxy, $(C_5-C_{12})$heteroarylthio, $(C_5-C_{12})$heteroaryl-$NR^5$—, $(C_3-C_{13})$heterocyclyl, $(C_3-C_{13})$heterocyclyloxy, $(C_3-C_{13})$heterocyclylthio, $(C_3-C_{13})$heterocyclyl-$NR^5$—, hydroxy$(C_1-C_{10})$alkyl, mercapto$(C_1-C_6)$alkyl, $(NR^5R^6)$alkyl, or $(NR^5R^6)$carbonyl; and $R^8$ is absent or is $(C_6-C_{12})$aryl, $(C_6-C_{12})$aryl$(C_1-C_6)$alkyl, $(C_3-C_8)$cycloalkyl, $(C_3-C_8)$cycloalkyl$(C_1-C_6)$alkyl, $(C_5-C_{12})$heteroaryl, $(C_5-C_{12})$heteroaryl$(C_1-C_6)$alkyl, $(C_3-C_{13})$heterocyclyl or $(C_3-C_{13})$heterocyclyl$(C_1-C_6)$alkyl.

WO 2013/170165 describes notably antibacterial compounds of formula (A5)

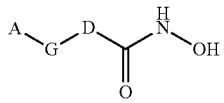
(A5)

wherein A is a substituted alkyl group, wherein at least one substituent is hydroxy, or A is a substituted cycloalkyl group, wherein at least one substituent is hydroxy or hydroxyalkyl; G is a group comprising at least one carbon-carbon double or triple bond and/or a phenyl ring; D represents a group selected from

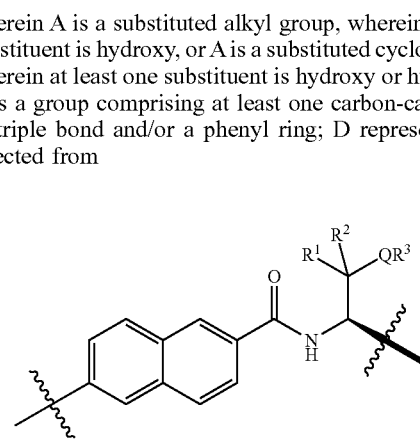

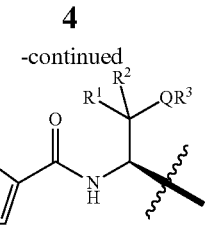

Q is O or NR, wherein R is H or an unsubstituted $(C_1-C_3)$ alkyl; $R^1$ and $R^2$ independently are selected from the group consisting of H and substituted or unsubstituted $(C_1-C_3)$ alkyl, or $R^1$ and $R^2$, together with the carbon atom to which they are attached, form an unsubstituted $(C_3-C_4)$cycloalkyl group or an unsubstituted 4-6 membered heterocyclic group; and $R^3$ is selected from the group consisting of hydrogen, substituted or unsubstituted $(C_1-C_3)$alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, and substituted or unsubstituted heteroarylalkyl.

In a previous, yet unpublished patent application, we have reported antibacterial 2H-indazole derivatives of general formula (A6)

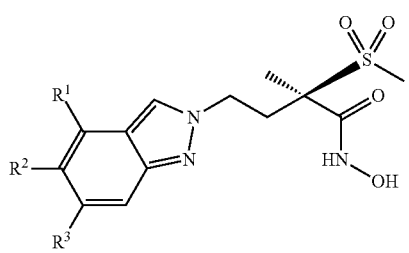
(A6)

wherein
$R^1$ is H or halogen; $R^2$ is $(C_3-C_4)$alkynyloxy or the group M; $R^3$ is H or halogen; M is one of the groups $M^A$ and $M^B$ represented below

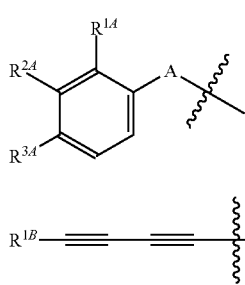

wherein A is a bond, $CH_2CH_2$, $CH$=$CH$ or $C$≡$C$; $R^{1A}$ represents H or halogen; $R^{2A}$ represents H, alkoxy or halogen; $R^{3A}$ represents H, alkoxy, hydroxyalkoxy, thioalkoxy, trifluoromethoxy, amino, dialkylamino, hydroxyalkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxyalkyl)oxetan-3-yl, 3-aminooxetan-3-yl, 3-(dialkylamino)oxetan-3-yl, 3-hydroxythietan-3-yl, morpholin-4-ylalkoxy, morpholin-4-ylalkyl, oxazol-2-yl or [1,2,3]triazol-2-yl; and R$^{1B}$ represents 3-hydroxyoxetan-3-yl, 3-hydroxythietan-3-yl, hydroxyalkyl, aminoalkyl, trans-2-hydroxymethyl-cycloprop-1-yl or 4-hydroxytetrahydro-2H-pyran-4-yl.

The instant invention provides new antibacterial 1H-indazole and 1H-substituted indole derivatives, namely the compounds of formula I described herein.

Various embodiments of the invention are presented hereafter:

1) The invention relates to compounds of formula I

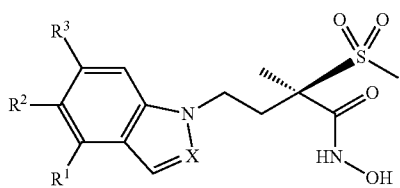

I wherein
X represents N or CH;
R$^1$ represents H or halogen;
R$^2$ represents (C$_3$-C$_4$)alkynyloxy or the group M;
R$^3$ represents H or halogen;
M is one of the groups M$^A$ and M$^B$ represented below

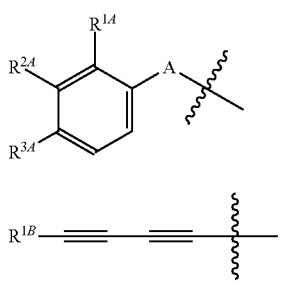

wherein A represents a bond, CH$_2$CH$_2$, CH=CH or C≡C;
R$^{1A}$ represents H or halogen;
R$^{2A}$ represents H, (C$_1$-C$_3$)alkoxy or halogen;
R$^{3A}$ represents H, (C$_1$-C$_3$)alkoxy, hydroxy(C$_1$-C$_4$)alkoxy, (C$_1$-C$_3$)alkoxy(C$_2$-C$_3$)alkoxy, (C$_1$-C$_3$)thioalkoxy, trifluoromethoxy, amino, hydroxy(C$_1$-C$_4$)alkyl, 2-hydroxyacetamido, 1-aminocyclopropyl, 1-hydroxymethyl-cycloprop-1-yl, 1-((phosphonooxy)methyl)cyclopropyl, 1-(((dimethylglycyl)oxy)methyl)cyclopropyl, trans-2-hydroxymethyl-cycloprop-1-yl, 1,2-dihydroxyethyl, 3-hydroxyoxetan-3-yl, 3-(hydroxy(C$_1$-C$_3$)alkyl)oxetan-3-yl, 3-aminooxetan-3-yl, 3-hydroxythietan-3-yl, morpholin-4-yl(C$_2$-C$_3$)alkoxy, morpholin-4-yl-(C$_1$-C$_2$)alkyl, oxazol-2-yl or [1,2,3]triazol-2-yl; and
R$^{1B}$ represents hydroxy(C$_1$-C$_3$)alkyl, dihydroxy(C$_2$-C$_4$) alkyl, amino(C$_1$-C$_3$)alkyl, (dimethylamino)methyl, 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, 1-aminomethyl-cycloprop-1-yl, trans-2-hydroxymethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxyoxetan-3-yl, 3-hydroxymethyl-oxetan-3-yl, 3-hydroxythietan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethylbicyclo[1,1,1]pentan-1-yl, 3-hydroxymethylbicyclo[1,1,1]pentan-1-yl, piperidin-4-yl, 1-(2-hydroxyacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl;
and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "(C$_x$-C$_y$)alkyl" (x and y each being an integer) refers to a straight or branched chain alkyl group containing x to y carbon atoms. For example, a (C$_1$-C$_3$)alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "hydroxyalkyl", used alone or in combination, refers to an alkyl group as defined before wherein one hydrogen atom has been replaced by a hydroxy group. The term "hydroxy(C$_x$-C$_y$)alkyl" (x and y each being an integer) refers to a hydroxyalkyl group as defined before which contains x to y carbon atoms. For example, a hydroxy(C$_1$-C$_4$)alkyl group is a hydroxyalkyl group as defined before which contains from one to four carbon atoms. Representative examples of hydroxyalkyl groups include hydroxymethyl, 2-hydroxyethyl, 2-hydroxypropyl and 3-hydroxypropyl. Preferred are hydroxymethyl and 2-hydroxyethyl. Most preferred is hydroxymethyl.

The term "dihydroxyalkyl", used alone or in combination, refers to an alkyl group containing from two to four carbon atoms wherein two hydrogen atoms on two different carbon atoms have each been replaced by a hydroxy group. The term "dihydroxy(C$_x$-C$_y$)alkyl" (x and y each being an integer) refers to a dihydroxyalkyl group as defined before which contains x to y carbon atoms. A preferred dihydroxyalkyl group is 2,3-dihydroxyprop-1-yl.

The term "aminoalkyl", used alone or in combination, refers to an alkyl group as defined before wherein one hydrogen atom has been replaced by an amino group. The term "amino(C$_x$-C$_y$)alkyl" (x and y each being an integer) refers to an aminoalkyl group as defined which contains x to y carbon atoms. For example, an amino (C$_1$-C$_4$)alkyl group is an aminoalkyl group as defined before which contains from one to four carbon atoms. Representative examples of aminoalkyl groups include aminomethyl, 2-aminoethyl, 2-aminopropyl, 2-aminoprop-2-yl and 3-aminopropyl. Preferred are aminomethyl, 2-aminoethyl and 2-aminopropyl. Most preferred is 2-aminoprop-2-yl.

The term "alkoxy", used alone or in combination, refers to a straight or branched chain alkoxy group containing from one to four carbon atoms. The term "(C$_x$-C$_y$)

alkoxy" (x and y each being an integer) refers to an alkoxy group as defined before containing x to y carbon atoms. For example, a ($C_1$-$C_3$)alkoxy group contains from one to three carbon atoms. Representative examples of alkoxy groups include methoxy, ethoxy, n-propoxy and iso-propoxy. Preferred are methoxy and ethoxy. Most preferred is methoxy.

The term "hydroxyalkoxy", used alone or in combination, refers to a straight or branched chain alkoxy group containing from one to four carbon atoms wherein one of the carbon atoms bears a hydroxy group. The term "hydroxy($C_x$-$C_y$)alkoxy" (x and y each being an integer) refers to a hydroxyalkoxy group as defined before containing x to y carbon atoms. For example, a hydroxy($C_1$-$C_4$)alkoxy group contains from one to four carbon atoms. Representative examples of hydroxyalkoxy groups include 2-hydroxyethoxy, 2-hydroxypropoxy, 3-hydroxypropoxy and 4-hydroxybutoxy. Preferred are 2-hydroxyethoxy and 3-hydroxypropoxy. Most preferred is 2-hydroxyethoxy.

The term "alkoxyalkoxy", used alone or in combination, refers to an alkoxy group containing from two to four carbon atoms wherein one hydrogen atom has been replaced by an alkoxy group containing from one to four carbon atoms. For example "($C_1$-$C_3$)alkoxy($C_2$-$C_3$)alkoxy" refers to a straight or branched chain alkoxy group containing from two to three carbon atoms, one hydrogen atom of which has been replaced by a straight or branched chain alkoxy group containing from one to three carbon atoms. A preferred ($C_1$-$C_3$)alkoxy($C_2$-$C_3$)alkoxy group is 2-methoxyethoxy.

The term "thioalkoxy", used alone or in combination, refers to a straight or branched chain alkoxy group containing from one to four carbon atoms wherein the oxygen atom has been replaced by a sulphur atom. The term "($C_x$-$C_y$)thioalkoxy" (x and y each being an integer) refers to a thioalkoxy group as defined before containing x to y carbon atoms. For example, a ($C_1$-$C_3$)thioalkoxy group contains from one to three carbon atoms. Representative examples of thioalkoxy groups include methylthio, ethylthio, n-propylthio and iso-propylthio. Preferred are methylthio and ethylthio. Most preferred is methylthio.

The term "alkynyloxy", used alone or in combination, refers to a straight or branched chain alkynyloxy group containing from two to five carbon atoms. The term "($C_x$-$C_y$)alkynyloxy" (x and y each being an integer) refers to an alkynyloxy group as defined before containing x to y carbon atoms. For example, a ($C_3$-$C_4$) alkynyloxy group contains from three to four carbon atoms. Representative examples of alkynyloxy groups include prop-2-yn-1-yloxy, but-2-yn-1-yloxy and but-3-yn-1-yloxy. Preferred are but-2-yn-1-yloxy and but-3-yn-1-yloxy.

The term "3-(hydroxy($C_1$-$C_3$)alkyl)oxetan-3-yl" refers to an oxetan-3-yl group wherein the hydrogen on the carbon at position 3 of the oxetane ring has been replaced by a hydroxy($C_1$-$C_3$)alkyl group as defined before. Examples of 3-(hydroxy($C_1$-$C_3$)alkyl)oxetan-3-yl groups are 3-hydroxymethyl-oxetan-3-yl and 3-(2-hydroxyethyl)-oxetan-3-yl. The most preferred 3-(hydroxy($C_1$-$C_3$)alkyl)oxetan-3-yl group is 3-hydroxymethyl-oxetan-3-yl.

The term "morpholin-4-yl-($C_1$-$C_2$)alkyl" refers to a ($C_1$-$C_2$)alkyl group as defined before wherein one of the hydrogen atoms has been replaced by a morpholin-4-yl group. Examples of morpholin-4-yl-($C_1$-$C_2$)alkyl groups are morpholin-4-ylmethyl and 2-morpholin-4-yl-ethyl. The most preferred morpholino($C_1$-$C_2$)alkyl group is morpholin-4-ylmethyl.

The term "halogen" refers to fluorine, chlorine, bromine or iodine, and preferably to fluorine or chlorine, and most preferably to fluorine.

The term "quinolone-resistant", when used in this text, refers to a bacterial strain against which ciprofloxacin has a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, $7^{th}$ ed., Clinical and Laboratory Standards Institute (CLSI) Document M7-A7, Wayne, Pa., USA (2006)).

The term "multi-drug resistant", when used in this text, refers to a bacterial strain against which at least three antibiotic compounds selected from three distinct antibiotic categories have Minimal Inhibitory Concentrations (MICs) over their respective clinical breakpoints, whereby said three distinct antibiotic categories are chosen among penicillins, combinations of penicillins with beta-lactamase inhibitors, cephalosporins, carbapenems, monobactams, fluoro-quinolones, aminoglycosides, phosphonic acids, tetracyclins and polymixins. Clinical breakpoints are defined according to the latest available list published by Clinical and Laboratory Standards Institute (Wayne, Pa., USA). Accordingly, clinical breakpoints are the levels of MIC at which, at a given time, a bacterium is deemed either susceptible or resistant to treatment by the corresponding antibiotic or antibiotic combination.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH (2008) and 'Pharmaceutical Salts and Co-crystals', Johan Wouters and Luc Quéré (Eds.), RSC Publishing (2012).

In this text, a bond interrupted by a wavy line shows a point of attachment of the radical drawn to the rest of the molecule. For example, the radical drawn below

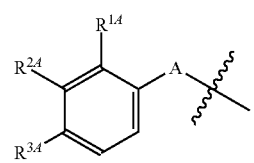

wherein A represents a bond, and each of $R^{1A}$, $R^{2A}$ and $R^{3A}$ represents H is the phenyl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) The invention notably relates to compounds of formula I according to embodiment 1) that are also compounds of formula $I_P$

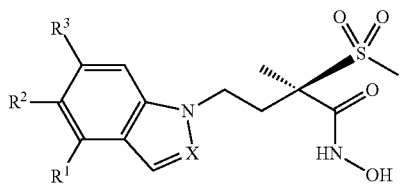

wherein
X represents N or CH;
$R^1$ represents H or halogen;
$R^2$ represents $(C_3-C_4)$alkynyloxy or the group M;
$R^3$ represents H or halogen;
M is one of the groups $M^A$ and $M^B$ represented below

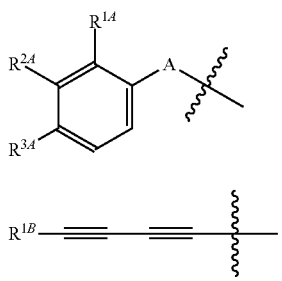

wherein A represents a bond, $CH_2CH_2$, CH=CH or C≡C;
$R^{1A}$ represents H or halogen;
$R^{2A}$ represents H, $(C_1-C_3)$alkoxy or halogen;
$R^{3A}$ represents H, $(C_1-C_3)$alkoxy, hydroxy$(C_1-C_4)$alkoxy, $(C_1-C_3)$thioalkoxy, trifluoromethoxy, amino, hydroxy$(C_1-C_4)$alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, 3-hydroxythietan-3-yl, morpholin-4-yl$(C_2-C_3)$alkoxy, morpholin-4-yl-$(C_1-C_2)$alkyl, oxazol-2-yl or [1,2,3]triazol-2-yl; and
$R^{1B}$ represents 3-hydroxyoxetan-3-yl, 3-hydroxythietan-3-yl, hydroxy$(C_1-C_3)$alkyl, amino$(C_1-C_3)$alkyl, 1-hydroxymethyl-cycloprop-1-yl or trans-2-hydroxymethyl-cycloprop-1-yl;
and to salts (in particular pharmaceutically acceptable salts) of compounds of formula $I_P$.

3) The invention in particular relates to compounds of formula I according to embodiment 1) which are also compounds of formula $I_{CE}$

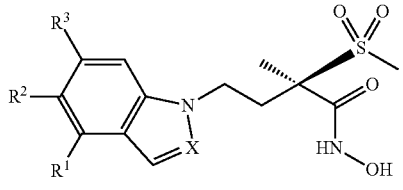

wherein
X represents N or CH;
$R^1$ represents H or halogen;
$R^2$ represents $(C_3-C_4)$alkynyloxy or the group M;
$R^3$ represents H or halogen;
M is one of the groups $M^A$ and $M^B$ represented below

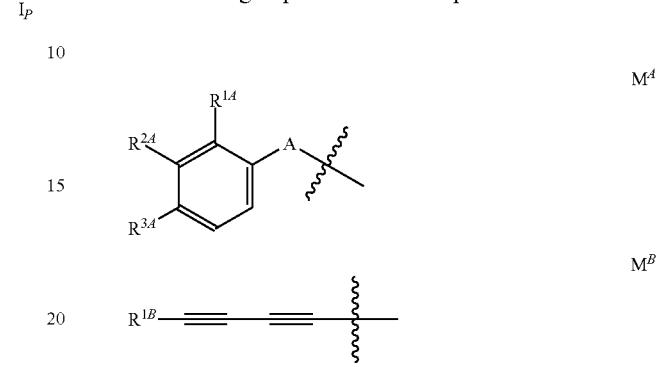

wherein A represents a bond, $CH_2CH_2$, CH=CH or C≡C;
$R^{1A}$ represents H or halogen;
$R^{2A}$ represents H or $(C_1-C_3)$alkoxy;
$R^{3A}$ represents H, $(C_1-C_3)$alkoxy, hydroxy$(C_1-C_4)$alkoxy, $(C_1-C_3)$thioalkoxy, trifluoromethoxy, amino, hydroxy$(C_1-C_4)$alkyl, 2-hydroxyacetamido, 1-hydroxymethyl-cycloprop-1-yl, 1-((phosphonooxy)methyl)cyclopropyl, 1-(((dimethylglycyl)oxy)methyl)cyclopropyl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-hydroxythietan-3-yl, morpholin-4-yl-$(C_1-C_2)$alkyl or [1,2,3]triazol-2-yl; and
$R^{1B}$ represents 3-hydroxyoxetan-3-yl, 3-hydroxythietan-3-yl, hydroxy$(C_1-C_3)$alkyl, dihydroxy$(C_2-C_4)$alkyl, amino $(C_1-C_3)$alkyl, 1-hydroxymethyl-cycloprop-1-yl, 1-aminomethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl;
and to salts (in particular pharmaceutically acceptable salts) of compounds of formula $I_{CE}$.

4) The invention furthermore relates to compounds of formula $I_{CE}$ according to embodiment 3) which are also compounds of formula $I_{CEP}$

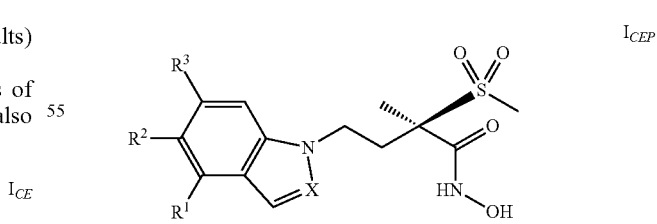

wherein
X represents N or CH;
$R^1$ represents H or halogen;
$R^2$ represents $(C_3-C_4)$alkynyloxy or the group M;
$R^3$ represents H or halogen;

M is one of the groups $M^A$ and $M^B$ represented below

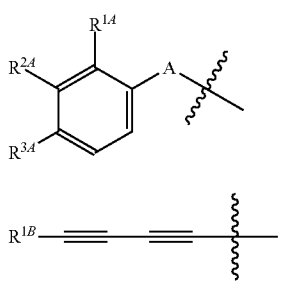

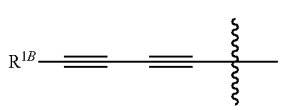

wherein A represents a bond, $CH_2CH_2$, $CH=CH$ or $C\equiv C$;
$R^{1A}$ represents H or halogen;
$R^{2A}$ represents H or $(C_1-C_3)$alkoxy;
$R^{3A}$ represents H, $(C_1-C_3)$alkoxy, hydroxy$(C_1-C_4)$alkoxy, $(C_1-C_3)$thioalkoxy, trifluoromethoxy, amino, hydroxy$(C_1-C_4)$alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-hydroxythietan-3-yl, morpholin-4-yl-$(C_1-C_2)$alkyl or [1,2,3]triazol-2-yl; and
$R^{1B}$ represents 3-hydroxyoxetan-3-yl, 3-hydroxythietan-3-yl, hydroxy$(C_1-C_3)$alkyl, amino$(C_1-C_3)$alkyl, 1-hydroxymethyl-cycloprop-1-yl or trans-2-hydroxymethyl-cycloprop-1-yl;
and to salts (in particular pharmaceutically acceptable salts) of compounds of formula $I_{CEP}$.

5) In particular, the compounds of formula $I_{CEP}$ according to embodiment 4) will be such that $R^2$ represents the group $M^A$ or $M^B$

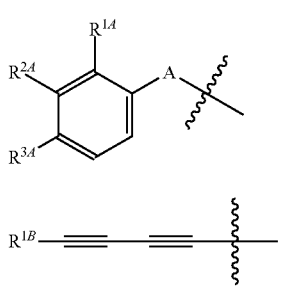

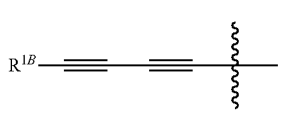

wherein A represents a bond or $C\equiv C$;
$R^{1A}$ represents H or halogen;
$R^{2A}$ represents H;
$R^{3A}$ represents $(C_1-C_3)$alkoxy, hydroxy$(C_1-C_4)$alkoxy, $(C_1-C_3)$thioalkoxy, hydroxy$(C_1-C_4)$alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-hydroxythietan-3-yl or [1,2,3]triazol-2-yl; and $R^{1B}$ represents 3-hydroxyoxetan-3-yl, 3-hydroxythietan-3-yl, hydroxy$(C_1-C_3)$alkyl, amino$(C_1-C_3)$alkyl, 1-hydroxymethyl-cycloprop-1-yl or trans-2-hydroxymethyl-cycloprop-1-yl.

6) In particular, the compounds of formula I according to one of embodiments 1) to 5) will be such that $R^1$ represents H or fluorine, $R^3$ represents H or fluorine, $R^{1A}$, when present, represents H or fluorine and $R^{2A}$, when present, represents H.

7) According to one main embodiment of this invention, the compounds of formula I as defined in one of embodiments 1) to 6) will be such that $R^2$ represents the group $M^A$.

8) One sub-embodiment of embodiment 7) relates to the compounds of formula I as defined in embodiment 7) wherein A represents a bond.

9) Preferably, the compounds of formula I according to embodiment 8) will be such that $R^{1A}$ represents H or halogen, $R^{2A}$ represents H and $R^{3A}$ represents $(C_1-C_3)$alkoxy, $(C_1-C_3)$thioalkoxy or [1,2,3]triazol-2-yl.

10) More preferably, the compounds of formula I according to embodiment 8) will be such that $R^{1A}$ represents H or fluorine, $R^{2A}$ represents H and $R^{3A}$ represents methoxy, methylthio or [1,2,3]triazol-2-yl.

11) Even more preferably, the compounds of formula I according to embodiment 8) will be such that $R^{1A}$ represents fluorine, $R^{2A}$ represents H and $R^{3A}$ represents methoxy.

12) Another sub-embodiment of embodiment 7) relates to the compounds of formula I as defined in embodiment 7) wherein A represents $C\equiv C$.

13) Preferably, the compounds of formula I according to embodiment 12) will be such that $R^{1A}$ represents H or halogen, $R^{2A}$ represents H and $R^{3A}$ represents hydroxy$(C_1-C_4)$alkoxy, hydroxy$(C_1-C_4)$alkyl, 2-hydroxyacetamido, 1-hydroxymethyl-cycloprop-1-yl, 1-((phosphonooxy)methyl)cyclopropyl, 1-(((dimethylglycyl)oxy)methyl)cyclopropyl, trans-2-hydroxymethyl-cycloprop-1-yl, 1,2-dihydroxyethyl, 3-hydroxyoxetan-3-yl, 3-hydroxythietan-3-yl or 3-(hydroxy$(C_1-C_3)$alkyl)oxetan-3-yl (and in particular such that $R^{1A}$ represents H or halogen, $R^{2A}$ represents H and $R^{3A}$ represents hydroxy$(C_1-C_4)$alkoxy, hydroxy$(C_1-C_4)$alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-hydroxythietan-3-yl or 3-(hydroxy$(C_1-C_3)$alkyl)oxetan-3-yl).

14) More preferably, the compounds of formula I according to embodiment 12) will be such that $R^{1A}$ represents H or fluorine, $R^{2A}$ represents H and $R^{3A}$ represents hydroxy$(C_1-C_4)$alkyl, trans-2-hydroxymethyl-cycloprop-1-yl, 1,2-dihydroxyethyl, 3-hydroxyoxetan-3-yl or 3-hydroxythietan-3-yl.

15) Even more preferably, the compounds of formula I according to embodiment 12) will be such that $R^{1A}$ represents H or fluorine, $R^{2A}$ represents H and $R^{3A}$ represents hydroxymethyl, 1-hydroxyethyl, 2-hydroxyethyl, trans-2-hydroxymethyl-cycloprop-1-yl, 1,2-dihydroxyethyl, 3-hydroxyoxetan-3-yl or 3-hydroxythietan-3-yl.

16) According to another main embodiment of this invention, the compounds of formula I as defined in one of embodiments 1) to 6) will be such that $R^2$ represents the group $M^B$.

17) Preferably, the compounds of formula I according to embodiment 16) will be such that $R^{1B}$ represents 3-hydroxyoxetan-3-yl, 3-hydroxythietan-3-yl, hydroxy$(C_1-C_3)$alkyl, 2-aminoprop-2-yl, 1-hydroxymethyl-cycloprop-1-yl or trans-2-hydroxymethyl-cycloprop-1-yl.

18) More preferably, the compounds of formula I according to embodiment 16) will be such that $R^{1B}$ represents 3-hydroxyoxetan-3-yl, 2-aminoprop-2-yl, 1-hydroxymethyl-cycloprop-1-yl or trans-2-hydroxymethyl-cycloprop-1-yl.

19) Even more preferably, the compounds of formula I according to embodiment 16) will be such that $R^{1B}$ represents trans-2-hydroxymethyl-cycloprop-1-yl.

20) According to a further main embodiment of this invention, the compounds of formula I as defined in embodiment 1) or 2) will be such that $R^2$ represents $(C_3-C_4)$alkynyloxy.

21) Preferably, the compounds of formula I according to embodiment 20) will be such that $R^2$ represents but-2-yn-1-yloxy.

22) According to a further main embodiment of this invention, the compounds of formula I as defined in embodiment 1) will be such that $R^2$ represents the group $M^A$ wherein A represents $CH_2CH_2$.

23) According to yet a further main embodiment of this invention, the compounds of formula I as defined in embodiment 1) will be such that $R^2$ represents the group $M^A$ wherein A represents CH=CH.

24) Preferably, the compounds of formula I according to embodiment 23) will be such that $R^{1A}$ represents H, $R^{2A}$ represents H and $R^{3A}$ represents H, hydroxy($C_1$-$C_4$)alkyl, trans-2-hydroxymethyl-cycloprop-1-yl or 3-hydroxyoxetan-3-yl.

25) In particular, the compounds of formula I according to embodiment 23) will be such that $R^{1A}$ represents H, $R^{2A}$ represents H and $R^{3A}$ represents H.

26) According to one variant of this invention, the compounds of formula I according to one of embodiments 1) to 6) will be such that $R^1$ represents H and $R^3$ represents H.

27) According to another variant of this invention, the compounds of formula I according to one of embodiments 1) to 6) will be such that $R^1$ represents fluorine and $R^3$ represents H.

28) According to yet another variant of this invention, the compounds of formula I according to one of embodiments 1) to 6) will be such that $R^1$ represents H and $R^3$ represents fluorine.

29) According to one main variant of this invention, the compounds of formula I according to one of embodiments 1) to 28) will be such that X represents CH.

30) According to the other main variant of this invention, the compounds of formula I according to one of embodiments 1) to 28) will be such that X represents N.

31) In a preferred embodiment, the compounds of formula I according to embodiment 1) will be such that:
X represents CH or N;
$R^1$ represents H or halogen;
$R^2$ represents the group M;
$R^3$ represents H or halogen; and
M is the one of the groups $M^A$ and $M^B$ represented below

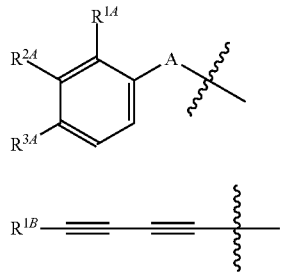

wherein A represents a bond or C≡C;
$R^{1A}$ represents H or halogen;
$R^{2A}$ represents H;
$R^{3A}$ represents ($C_1$-$C_3$)alkoxy, hydroxy($C_1$-$C_4$)alkoxy, ($C_1$-$C_3$)thioalkoxy, hydroxy($C_1$-$C_4$)alkyl, 2-hydroxyacetamido, 1-hydroxymethyl-cycloprop-1-yl, 1-((phosphonooxy)methyl)cyclopropyl, 1-(((dimethylglycyl)oxy)methyl)cyclopropyl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-hydroxythietan-3-yl or [1,2,3]triazol-2-yl (and in particular ($C_1$-$C_3$)alkoxy, hydroxy($C_1$-$C_4$)alkoxy, ($C_1$-$C_3$)thioalkoxy, hydroxy($C_1$-$C_4$)alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy($C_1$-$C_3$)alkyl)oxetan-3-yl, 3-hydroxythietan-3-yl or [1,2,3]triazol-2-yl); and
$R^{1B}$ represents 3-hydroxyoxetan-3-yl, 3-hydroxythietan-3-yl, hydroxy($C_1$-$C_3$)alkyl, amino($C_1$-$C_3$)alkyl, 1-hydroxymethyl-cycloprop-1-yl or trans-2-hydroxymethyl-cycloprop-1-yl.

32) In a more preferred embodiment, the compounds of formula I according to embodiment 1) or 2) will be such that:
X represents CH or N;
$R^1$ represents H or fluorine;
$R^2$ represents the group M;
$R^3$ represents H or fluorine; and
M is the one of the groups $M^A$ and $M^B$ represented below

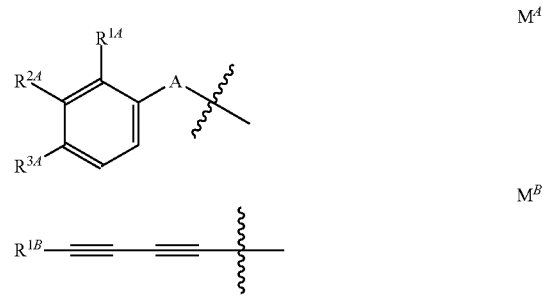

wherein A represents C≡C;
$R^{1A}$ represents H or fluorine;
$R^{2A}$ represents H;
$R^{3A}$ represents ($C_1$-$C_3$)alkoxy, hydroxy($C_1$-$C_3$)alkyl, trans-2-hydroxymethyl-cycloprop-1-yl, 1,2-dihydroxyethyl, 3-hydroxyoxetan-3-yl or 3-hydroxythietan-3-yl; and
$R^{1B}$ represents 3-hydroxyoxetan-3-yl, 2-aminoprop-2-yl, 1-hydroxymethyl-cycloprop-1-yl or trans-2-hydroxymethyl-cycloprop-1-yl.

33) In an even more preferred embodiment, the compounds of formula I according to embodiment 1) or 2) will be such that:
X represents CH or N;
$R^1$ represents H or fluorine;
$R^2$ represents the group M;
$R^3$ represents H or fluorine; and
M is the one of the groups $M^A$ and $M^B$ represented below

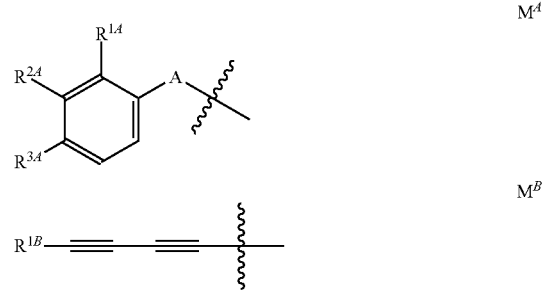

wherein A represents C≡C;
R$^{1A}$ represents H;
R$^{2A}$ represents H;
R$^{3A}$ represents hydroxymethyl, 1-hydroxyethyl, 2-hydroxyethyl, trans-2-hydroxymethyl-cycloprop-1-yl, 1,2-dihydroxyethyl, 3-hydroxyoxetan-3-yl or 3-hydroxythietan-3-yl; and
R$^{1B}$ represents 3-hydroxyoxetan-3-yl, 2-aminoprop-2-yl, 1-hydroxymethyl-cycloprop-1-yl or trans-2-hydroxymethyl-cycloprop-1-yl.

34) According to one variant of embodiment 33), the compounds of formula I according to embodiment 33) will be such that M is the group M$^A$ 35) According to the other variant of embodiment 33), the compounds of formula I according to embodiment 33) will be such that M is the group M$^B$.

36) Another embodiment of this invention relates to compounds of formula I as defined in one of embodiments 1) to 35) as well as to isotopically labelled, especially $^2$H (deuterium) labelled compounds of formula I as defined in one of embodiments 1) to 35), which compounds are identical to the compounds of formula I as defined in one of embodiments 1) to 35) except that one or more atoms has or have each been replaced by an atom having the same atomic number but an atomic mass different from the atomic mass usually found in nature. Isotopically labelled, especially $^2$H (deuterium) labelled compounds of formula I and salts (in particular pharmaceutically acceptable salts) thereof are thus within the scope of the present invention. Substitution of hydrogen with the heavier isotope $^2$H (deuterium) may lead to greater metabolic stability, resulting e.g. in an increased in-vivo half-life, reduced dosage requirements, or an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

37) Particularly preferred are the following compounds of formula I as defined in embodiment 1) or 2):
(R)-4-(5-(2-fluoro-4-(methylthio)phenyl)-1H-indazol-1-yl)-N-hydroxy-2-methyl-2-(methylsulfonyl)butanamide;
(R)-4-(5-(2-fluoro-4-methoxyphenyl)-1H-indol-1-yl)-N-hydroxy-2-methyl-2-(methylsulfonyl)butanamide;
(R)-4-(5-(2-fluoro-4-methoxyphenyl)-1H-indazol-1-yl)-N-hydroxy-2-methyl-2-(methylsulfonyl)butanamide;
(R)—N-hydroxy-4-(5-((4-(hydroxymethyl)phenyl)ethynyl)-1H-indazol-1-yl)-2-methyl-2-(methylsulfonyl)butanamide;
(R)—N-hydroxy-4-(5-((3-hydroxyoxetan-3-yl)buta-1,3-diyn-1-yl)-1H-indazol-1-yl)-2-methyl-2-(methylsulfonyl)butanamide;
(R)-4-(5-(4-(2H-1,2,3-triazol-2-yl)phenyl)-1H-indazol-1-yl)-N-hydroxy-2-methyl-2-(methylsulfonyl)butanamide;
(R)—N-hydroxy-4-(5-(5-hydroxy-5-methylhexa-1,3-diyn-1-yl)-1H-indazol-1-yl)-2-methyl-2-(methylsulfonyl)butanamide;
(R)—N-hydroxy-4-(5-((4-(2-hydroxypropan-2-yl)phenyl)ethynyl)-1H-indazol-1-yl)-2-methyl-2-(methylsulfonyl)butanamide;
(R)—N-hydroxy-4-(5-((4-(hydroxymethyl)phenyl)ethynyl)-1H-indol-1-yl)-2-methyl-2-(methylsulfonyl)butanamide;
(R)—N-hydroxy-4-(5-((4-(3-hydroxyoxetan-3-yl)phenyl)ethynyl)-1H-indol-1-yl)-2-methyl-2-(methylsulfonyl)butanamide;
(R)—N-hydroxy-4-(5-((3-hydroxyoxetan-3-yl)buta-1,3-diyn-1-yl)-1H-indol-1-yl)-2-methyl-2-(methylsulfonyl)butanamide;
(R)—N-hydroxy-4-(5-((4-(3-hydroxyoxetan-3-yl)phenyl)ethynyl)-1H-indazol-1-yl)-2-methyl-2-(methylsulfonyl)butanamide;
(R)—N-hydroxy-4-(5-((3-hydroxythietan-3-yl)buta-1,3-diyn-1-yl)-1H-indazol-1-yl)-2-methyl-2-(methylsulfonyl)butanamide;
(R)—N-hydroxy-4-(5-((4-(2-hydroxyethyl)phenyl)ethynyl)-1H-indazol-1-yl)-2-methyl-2-(methylsulfonyl)butanamide;
(R)-4-(6-fluoro-5-((4-(3-hydroxyoxetan-3-yl)phenyl)ethynyl)-1H-indol-1-yl)-N-hydroxy-2-methyl-2-(methylsulfonyl)butanamide;
(R)—N-hydroxy-4-(5-((4-((R)-1-hydroxyethyl)phenyl)ethynyl)-1H-indazol-1-yl)-2-methyl-2-(methylsulfonyl)butanamide;
(R)—N-hydroxy-4-(5-(((1S,2S)-2-(hydroxymethyl)cyclopropyl)buta-1,3-diyn-1-yl)-1H-indol-1-yl)-2-methyl-2-(methylsulfonyl)butanamide;
(R)—N-hydroxy-4-(5-(((1R,2R)-2-(hydroxymethyl)cyclopropyl)buta-1,3-diyn-1-yl)-1H-indol-1-yl)-2-methyl-2-(methylsulfonyl)butanamide;
(R)—N-hydroxy-4-(5-((4-((1S,2S)-2-(hydroxymethyl)cyclopropyl)phenyl)ethynyl)-1H-indazol-1-yl)-2-methyl-2-(methylsulfonyl)butanamide;
(R)—N-hydroxy-4-(5-((4-((1R,2R)-2-(hydroxymethyl)cyclopropyl)phenyl)ethynyl)-1H-indazol-1-yl)-2-methyl-2-(methylsulfonyl)butanamide;
(R)-4-(5-((4-((R)-1,2-dihydroxyethyl)phenyl)ethynyl)-1H-indazol-1-yl)-N-hydroxy-2-methyl-2-(methylsulfonyl)butanamide;
(R)-4-(5-((4-((S)-1,2-dihydroxyethyl)phenyl)ethynyl)-1H-indazol-1-yl)-N-hydroxy-2-methyl-2-(methylsulfonyl)butanamide;
(R)—N-hydroxy-4-(5-((4-((S)-1-hydroxyethyl)phenyl)ethynyl)-1H-indazol-1-yl)-2-methyl-2-(methylsulfonyl)butanamide;
(R)-4-(5-(5-amino-5-methylhexa-1,3-diyn-1-yl)-1H-indazol-1-yl)-N-hydroxy-2-methyl-2-(methylsulfonyl)butanamide;
(R)—N-hydroxy-4-(5-((4-(1-(hydroxymethyl)cyclopropyl)phenyl)ethynyl)-1H-indol-1-yl)-2-methyl-2-(methylsulfonyl)butanamide;
(R)—N-hydroxy-4-(5-(((1S,2S)-2-(hydroxymethyl)cyclopropyl)buta-1,3-diyn-1-yl)-1H-indazol-1-yl)-2-methyl-2-(methylsulfonyl)butanamide;
(R)—N-hydroxy-4-(5-((4-(2-hydroxyethoxy)phenyl)ethynyl)-1H-indazol-1-yl)-2-methyl-2-methylsulfonyl)butanamide;
(R)—N-hydroxy-4-(5-((4-(2-hydroxyacetamido)phenyl)ethynyl)-1H-indazol-1-yl)-2-methyl-2-(methylsulfonyl)butanamide;
(R)—N-hydroxy-4-(5-((4-(2-hydroxypropan-2-yl)phenyl)ethynyl)-1H-indol-1-yl)-2-methyl-2-(methylsulfonyl)butanamide;
(R)-4-(4-fluoro-5-((4-(3-hydroxyoxetan-3-yl)phenyl)ethynyl)-1H-indazol-1-yl)-N-hydroxy-2-methyl-2-(methylsulfonyl)butanamide;
(R)-4-(4-fluoro-5-(((1S,2S)-2-(hydroxymethyl)cyclopropyl)buta-1,3-diyn-1-yl)-1H-indazol-1-yl)-N-hydroxy-2-methyl-2-(methylsulfonyl)butanamide;
(R)—N-hydroxy-4-(5-((3-hydroxythietan-3-yl)buta-1,3-diyn-1-yl)-1H-indol-1-yl)-2-methyl-2-(methylsulfonyl)butanamide;

(R)—N-hydroxy-4-(5-((4-(((1S,2S)-2-(hydroxymethyl)cyclopropyl)phenyl)ethynyl)-1H-indol-1-yl)-2-methyl-2-(methylsulfonyl)butanamide;
(R)—N-hydroxy-4-(5-((1-(hydroxymethyl)cyclopropyl)buta-1,3-diyn-1-yl)-1H-indazol-1-yl)-2-methyl-2-(methylsulfonyl)butanamide;
(R)—N-hydroxy-4-(5-((4-((S)-1-hydroxyethyl)phenyl)ethynyl)-1H-indol-1-yl)-2-methyl-2-(methylsulfonyl)butanamide;
(R)-4-(4-fluoro-5-((4-(2-hydroxyethyl)phenyl)ethynyl)-1H-indazol-1-yl)-N-hydroxy-2-methyl-2-(methylsulfonyl)butanamide;
(R)-4-(4-fluoro-5-((4-((R)-1-hydroxyethyl)phenyl)ethynyl)-1H-indazol-1-yl)-N-hydroxy-2-methyl-2-(methylsulfonyl)butanamide;
(R)-4-(4-fluoro-5-((3-hydroxyoxetan-3-yl)buta-1,3-diyn-1-yl)-1H-indazol-1-yl)-N-hydroxy-2-methyl-2-(methylsulfonyl)butanamide;
(R)-4-(4-fluoro-5-((1-(hydroxymethyl)cyclopropyl)buta-1,3-diyn-1-yl)-1H-indazol-1-yl)-N-hydroxy-2-methyl-2-(methylsulfonyl)butanamide;
(R)-4-(4-fluoro-5-((4-(3-(hydroxymethyl)oxetan-3-yl)phenyl)ethynyl)-1H-indazol-1-yl)-N-hydroxy-2-methyl-2-(methylsulfonyl)butanamide;
(R)-4-(6-fluoro-5-((2-(hydroxymethyl)cyclopropyl)buta-1,3-diyn-1-yl)-1H-indol-1-yl)-N-hydroxy-2-methyl-2-(methylsulfonyl)butanamide;
(R)—N-hydroxy-4-(5-(((1R,2R)-2-(hydroxymethyl)cyclopropyl)buta-1,3-diyn-1-yl)-1H-indazol-1-yl)-2-methyl-2-(methylsulfonyl)butanamide;
(R)-4-(5-((2-fluoro-4-(hydroxymethyl)phenyl)ethynyl)-1H-indol-1-yl)-N-hydroxy-2-methyl-2-(methylsulfonyl)butanamide;
(R)-4-(5-((4-((R)-1,2-dihydroxyethyl)phenyl)ethynyl)-1H-indol-1-yl)-N-hydroxy-2-methyl-2-(methylsulfonyl)butanamide;
(R)—N-hydroxy-4-(5-((4-(2-hydroxyethyl)phenyl)ethynyl)-1H-indol-1-yl)-2-methyl-2-(methylsulfonyl)butanamide;
(R)-4-(6-fluoro-5-(((1S,2S)-2-(hydroxymethyl)cyclopropyl)buta-1,3-diyn-1-yl)-1H-indazol-1-yl)-N-hydroxy-2-methyl-2-(methylsulfonyl)butanamide;
as well as the salts (in particular the pharmaceutically acceptable salts) thereof.

38) Also preferred are the following compounds of formula I as defined in embodiment 1):
(R)-4-(6-fluoro-5-((4-(2-hydroxyethyl)phenyl)ethynyl)-1H-indazol-1-yl)-N-hydroxy-2-methyl-2-(methylsulfonyl)butanamide;
(R)-(1-(4-((1-(4-(hydroxyamino)-3-methyl-3-(methylsulfonyl)-4-oxobutyl)-1H-indazol-5-yl)ethynyl)phenyl)cyclopropyl)methyl dihydrogen phosphate;
(R)-(1-(4-((1-(4-(hydroxyamino)-3-methyl-3-(methylsulfonyl)-4-oxobutyl)-1H-indazol-5-yl)ethynyl)phenyl)cyclopropyl)methyl dimethylglycinate;
(R)-4-(5-((R)-6,7-dihydroxyhepta-1,3-diyn-1-yl)-1H-indazol-1-yl)-N-hydroxy-2-methyl-2-(methylsulfonyl)butanamide;
(R)-4-(5-(((1s,3R,4S)-3,4-dihydroxycyclopentyl)buta-1,3-diyn-1-yl)-1H-indazol-1-yl)-N-hydroxy-2-methyl-2-(methylsulfonyl)butanamide;
(R)—N-hydroxy-4-(5-((4-(1-(hydroxymethyl)cyclopropyl)phenyl)ethynyl)-1H-indazol-1-yl)-2-methyl-2-(methylsulfonyl)butanamide;
(R)—N-hydroxy-4-(5-((3-(hydroxymethyl)bicyclo[1.1.1]pentan-1-yl)buta-1,3-diyn-1-yl)-1H-indazol-1-yl)-2-methyl-2-(methylsulfonyl)butanamide;
(R)-4-(5-((1-(aminomethyl)cyclopropyl)buta-1,3-diyn-1-yl)-1H-indazol-1-yl)-N-hydroxy-2-methyl-2-(methylsulfonyl)butanamide;
as well as the salts (in particular the pharmaceutically acceptable salts) thereof.

39) Further preferred are the following compounds of formula I as defined in embodiment 1) or 2):
(R)-4-(5-(but-2-yn-1-yloxy)-1H-indol-1-yl)-N-hydroxy-2-methyl-2-(methylsulfonyl)butanamide;
(R)-4-(5-(2-fluoro-3-methoxyphenyl)-1H-indazol-1-yl)-N-hydroxy-2-methyl-2-(methylsulfonyl)butanamide;
(R)-(E)-N-hydroxy-2-methyl-2-(methylsulfonyl)-4-(5-styryl-1H-indazol-1-yl)butanamide;
(R)—N-hydroxy-2-methyl-2-(methylsulfonyl)-4-(5-phenethyl-1H-indazol-1-yl)butanamide;
(R)—N-hydroxy-2-methyl-2-(methylsulfonyl)-4-(5-((4-(morpholinomethyl)phenyl)ethynyl)-1H-indazol-1-yl)butanamide 4-toluenesulfonic acid salt;
(R)-4-(5-((4-aminophenyl)ethynyl)-1H-indazol-1-yl)-N-hydroxy-2-methyl-2-(methylsulfonyl)butanamide;
(R)—N-hydroxy-2-methyl-2-(methylsulfonyl)-4-(5-(4-(trifluoromethoxy)phenyl)-1H-indazol-1-yl)butanamide;
(R)-4-(5-(4-(2H-1,2,3-triazol-2-yl)phenyl)-1H-indol-1-yl)-N-hydroxy-2-methyl-2-(methylsulfonyl)butanamide formate;
(R)—N-hydroxy-2-methyl-2-(methylsulfonyl)-4-(5-(4-(trifluoromethoxy)phenyl)-1H-indol-1-yl)butanamide;
(R)-4-(5-(2-fluoro-4-(methylthio)phenyl)-1H-indol-1-yl)-N-hydroxy-2-methyl-2-(methylsulfonyl)butanamide;
(R)-4-(6-fluoro-5-(2-fluoro-4-methoxyphenyl)-1H-indol-1-yl)-N-hydroxy-2-methyl-2-(methylsulfonyl)butanamide;
(R)-4-(4-fluoro-5-(2-fluoro-4-methoxyphenyl)-1H-indol-1-yl)-N-hydroxy-2-methyl-2-(methylsulfonyl)butanamide; and
(R)-4-(4-fluoro-5-((4-(3-hydroxyoxetan-3-yl)phenyl)ethynyl)-1H-indol-1-yl)-N-hydroxy-2-methyl-2-(methylsulfonyl)butanamide;
as well as the salts (in particular the pharmaceutically acceptable salts) thereof.

39) The invention further relates to the compounds of formula I as defined in embodiment 1) which are selected from the group consisting of the compounds listed in embodiment 37), the compounds listed in embodiment 38) and the compounds listed in embodiment 39). In particular, it also relates to the groups of compounds of formula I selected from the group consisting of the compounds listed in embodiment 37), the compounds listed in embodiment 38) and the compounds listed in embodiment 39), which groups of compounds furthermore correspond to one of embodiments 2) to 35), as well as to the salts (in particular the pharmaceutically acceptable salts) of such compounds. The invention moreover relates to any individual compound of formula I selected from the group consisting of the compounds listed in embodiment 37), the compounds listed in embodiment 38) and the compounds listed in embodiment 39), and to the salts (in particular the pharmaceutically acceptable salts) of such individual compound.

The compounds of formula I according to this invention, i.e. according to one of embodiments 1) to 39) above, exhibit antibacterial activity, especially against Gram-negative organisms and are therefore suitable to treat bacterial infections in mammals, especially humans. Said compounds may also be used for veterinary applications, such as treating infections in livestock and companion animals. They may further constitute substances for preserving inorganic and organic materials in particular all types of organic materials for example polymers, lubricants, paints, fibres, leather, paper and wood.

They may therefore be used for the treatment or prevention of infectious disorders caused by fermentative or non-fermentative gram negative bacteria, especially those caused by susceptible and multi-drug resistant Gram-negative bacteria. Examples of such Gram-negative bacteria include *Acinetobacter* spp. such as *Acinetobacter baumannii* or *Acinetobacter haemolyticus*, *Actinobacillus actinomycetemcomitans*, *Achromobacter* spp. such as *Achromobacter xylosoxidans* or *Achromobacter faecalis*, *Aeromonas* spp. such as *Aeromonas hydrophila*, *Bacteroides* spp. such as *Bacteroides fragilis*, *Bacteroides theataioatamicron*, *Bacteroides distasonis*, *Bacteroides ovatus* or *Bacteroides vulgatus*, *Bartonella hensenae*, *Bordetella* spp. such as *Bordetella pertussis*, *Borrelia* spp. such as *Borrelia Burgdorferi*, *Brucella* spp. such as *Brucella melitensis*, *Burkholderia* spp. such as *Burkholderia cepacia*, *Burkholderia pseudomallei* or *Burkholderia mallei*, *Campylobacter* spp. such as *Campylobacter jejuni*, *Campylobacter fetus* or *Campylobacter coli*, *Cedecea*, *Chlamydia* spp. such as *Chlamydia pneumoniae*, *Chlamydia trachomatis*, *Citrobacter* spp. such as *Citrobacter diversus* (*koseri*) or *Citrobacter freundii*, *Coxiella burnetii*, *Edwardsiella* spp. such as *Edwarsiella tarda*, *Ehrlichia chafeensis*, *Eikenella corrodens*, *Enterobacter* spp. such as *Enterobacter cloacae*, *Enterobacter aerogenes*, *Enterobacter agglomerans*, *Escherichia coli*, *Francisella tularensis*, *Fusobacterium* spp., *Haemophilus* spp. such as *Haemophilus influenzae* (beta-lactamase positive and negative) or *Haemophilus ducreyi*, *Helicobacter pylori*, *Kingella kingae*, *Klebsiella* spp. such as *Klebsiella oxytoca*, *Klebsiella pneumoniae* (including those encoding extended-spectrum beta-lactamases (hereinafter "ESBLs"), carbapenemases (KPCs), cefotaximase-Munich (CTX-M), metallo-beta-lactamases, and AmpC-type beta-lactamases that confer resistance to currently available cephalosporins, cephamycins, carbapenems, beta-lactams, and beta-lactam/beta-lactamase inhibitor combinations), *Klebsiella rhinoscleromatis* or *Klebsiella ozaenae*, *Legionella pneumophila*, *Mannheimia haemolyticus*, *Moraxella catarrhalis* (beta-lactamase positive and negative), *Morganella morganii*, *Neisseria* spp. such as *Neisseria gonorrhoeae* or *Neisseria meningitidis*, *Pasteurella* spp. such as *Pasteurella multocida*, *Plesiomonas shigelloides*, *Porphyromonas* spp. such as *Porphyromonas asaccharolytica*, *Prevotella* spp. such as *Prevotella corporis*, *Prevotella intermedia* or *Prevotella endodontalis*, *Proteus* spp. such as *Proteus mirabilis*, *Proteus vulgaris*, *Proteus penneri* or *Proteus myxofaciens*, *Porphyromonas asaccharolytica*, *Plesiomonas shigelloides*, *Providencia* spp. such as *Providencia stuartii*, *Providencia rettgeri* or *Providencia alcalifaciens*, *Pseudomonas* spp. such as *Pseudomonas aeruginosa* (including ceftazidime-, cefpirome- and cefepime-resistant *P. aeruginosa*, carbapenem-resistant *P. aeruginosa* or quinolone-resistant *P. aeruginosa*) or *Pseudomonas fluorescens*, *Ricketsia prowazekii*, *Salmonella* spp. such as *Salmonella typhi* or *Salmonella paratyphi*, *Serratia marcescens*, *Shigella* spp. such as *Shigella flexneri*, *Shigella boydii*, *Shigella sonnei* or *Shigella dysenteriae*, *Streptobacillus moniliformis*, *Stenotrophomonas maltophilia*, *Treponema* spp., *Vibrio* spp. such as *Vibrio cholerae*, *Vibrio parahaemolyticus*, *Vibrio vulnificus*, *Vibrio alginolyticus*, *Yersinia* spp. such as *Yersinia enterocolitica*, *Yersinia pestis* or *Yersinia pseudotuberculosis*.

The compounds of formula I according to this invention are thus likely to be useful for treating a variety of infections caused by fermentative or non-fermentative Gram-negative bacteria, especially infections such as: nosocomial pneumonia (related to infection by *Legionella pneumophila*, *Haemophilus influenzae*, or *Chlamydia pneumonia*); urinary tract infections; systemic infections (bacteraemia and sepsis); skin and soft tissue infections (including burn patients); surgical infections; intraabdominal infections; lung infections (including those in patients with cystic fibrosis); *Helicobacter pylori* (and relief of associated gastric complications such as peptic ulcer disease, gastric carcinogenesis, etc.); endocarditis; diabetic foot infections; osteomyelitis; otitis media, sinusitus, bronchitis, tonsillitis, and mastoiditis related to infection by *Haemophilus influenzae* or *Moraxella catarrhalis*; pharyngitis, rheumatic fever, and glomerulonephritis related to infection by *Actinobacillus haemolyticum*; sexually transmitted diseases related to infection by *Chlamydia trachormatis*, *Haemophilus ducreyi*, *Treponema pallidum*, *Ureaplasma urealyticum*, or *Neisseria gonorrheae*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis*, *Neisseria gonorrhoeae* or *H. influenzae*; gastroenteritis related to infection by *Campylobacter jejuni*; persistent cough related to infection by *Bordetella pertussis* and gas gangrene related to infection by *Bacteroides* spp. Other bacterial infections and disorders related to such infections that may be treated or prevented in accord with the method of the present invention are referred to in J. P. Sanford et al., "*The Sanford Guide to Antimicrobial Therapy*", 26th Edition, (Antimicrobial Therapy, Inc., 1996).

The preceding lists of infections and pathogens are to be interpreted merely as examples and in no way as limiting.

The compounds of formula I according to this invention, or the pharmaceutically acceptable salts thereof, may therefore be used for the preparation of a medicament, and are likely to be suitable, for the prevention or treatment of a bacterial infection, in particular for the prevention or treatment of a bacterial infection caused by Gram-negative bacteria, especially by multi-drug resistant Gram-negative bacteria.

The compounds of formula I according to this invention, or the pharmaceutically acceptable salts thereof, may thus especially be used for the preparation of a medicament, and likely to be are suitable, for the prevention or treatment of a bacterial infection caused by Gram-negative bacteria selected from the group consisting of *Acinetobacter baumannii*, *Burkholderia* spp. (e.g. *Burkholderia cepacia*), *Citrobacter* spp., *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia* and *Pseudomonas aeruginosa* (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection mediated by quinolone-resistant *Acinetobacter baumannii* bacteria or quinolone-resistant *Klebsiella pneumoniae* bacteria).

The compounds of formula I according to this invention, or the pharmaceutically acceptable salts thereof, may more especially be used for the preparation of a medicament, and are likely to be suitable, for the prevention or treatment of a bacterial infection caused by Gram-negative bacteria selected from the group consisting of *Citrobacter* spp., *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia* and *Pseudomo-* nas aeruginosa bacteria (notably of a bacterial infection caused by Gram-negative bacteria selected from the group consisting of *Klebsiella pneumoniae* and *Pseudomonas aeruginosa* bacteria, and in particular of a bacterial infection caused by *Pseudomonas aeruginosa* bacteria).

The compounds of formula I according to this invention, or the pharmaceutically acceptable salts thereof, may thus especially be used for the preparation of a medicament, and are likely to be suitable, for the prevention or treatment of a bacterial infection selected from urinary tract infections, systemic infections (such as bacteraemia and sepsis), skin and soft tissue infections (including burn patients), surgical infections; intraabdominal infections and lung infections (including those in patients with cystic fibrosis).

The compounds of formula I according to this invention, or the pharmaceutically acceptable salts thereof, may more especially be used for the preparation of a medicament, and are likely to be suitable, for the prevention or treatment of a bacterial infection selected from urinary tract infections, intraabdominal infections and lung infections (including those in patients with cystic fibrosis), and in particular for the prevention or treatment of a bacterial infection selected from urinary tract infections and intraabdominal infections.

Besides, the compounds of formula I according to this invention display intrinsic antibacterial properties and likely to have the ability to improve permeability of the outer membrane of Gram-negative bacteria to other antibacterial agents. Their use in combination with another antibacterial agent might offer some further advantages such as lowered side-effects of drugs due to lower doses used or shorter time of treatment, more rapid cure of infection shortening hospital stays, increasing spectrum of pathogens controlled, and decreasing incidence of development of resistance to antibiotics. The antibacterial agent for use in combination with a compound of formula I according to this invention will be selected from the group consisting of a penicillin antibiotic (such as ampicillin, piperacillin, penicillin G, amoxicillin, or ticarcillin), a cephalosporin antibiotic (such as ceftriaxone, cefatazidime, cefepime, cefotaxime) a carbapenem antibiotic (such as imipenem, or meropenem), a monobactam antibiotic (such as aztreonam), a fluoroquinolone antibiotic (such as ciprofloxacin, moxifloxacin or levofloxacin), a macrolide antibiotic (such as erythromycin or azithromycin), an aminoglycoside antibiotic (such as amikacin, gentamycin or tobramycin), a glycopeptide antibiotic (such as vancomycin or teicoplanin), a tetracycline antibiotic (such as tetracycline, oxytetracycline, doxycycline, minocycline or tigecycline), and linezolid, clindamycin, telavancin, daptomycin, novobiocin, rifampicin and polymyxin. Preferably, the antibacterial agent for use in combination with a compound of formula I according to this invention will be selected from the group consisting of vancomycin, tigecycline and rifampicin.

The compounds of formula I according to this invention, or the pharmaceutically acceptable salt thereof, may moreover be used for the preparation of a medicament, and are likely to be suitable, for the prevention or treatment (and especially the treatment) of infections caused by biothreat Gram negative bacterial pathogens as listed by the US Center for Disease Control (the list of such biothreat bacterial pathogens can be found at the web page http://www.selectagents.gov/Select%20Agents%20and%20Toxins%20List.html), and in particular by Gram negative pathogens selected from the group consisting of *Yersinia pestis*, *Francisella tularensis* (tularemia), *Burkholderia pseudomallei* and *Burkholderia mallei*.

One aspect of this invention therefore relates to the use of a compound of formula I according to one of embodiments 1) to 39), or of a pharmaceutically acceptable salt thereof, for the manufacture of a medicament for the prevention or treatment of a bacterial infection (in particular one of the previously mentioned infections caused by Gram-negative bacteria, especially by multi-drug resistant Gram-negative bacteria). Another aspect of this invention relates to a compound of formula I according to one of embodiments 1) to 39), or a pharmaceutically acceptable salt thereof, for the prevention or treatment of a bacterial infection (in particular for the prevention or treatment of one of the previously mentioned infections caused by Gram-negative bacteria, especially by multi-drug resistant Gram-negative bacteria). Yet another aspect of this invention relates to a compound of formula I according to one of embodiments 1) to 39), or a pharmaceutically acceptable salt thereof, as a medicament. Yet a further aspect of this invention relates to a pharmaceutical composition containing, as active principle, a compound of formula I according to one of embodiments 1) to 39), or a pharmaceutically acceptable salt thereof, and at least one therapeutically inert excipient.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I or $I_{CE}$.

Any reference to a compound of formula I or $I_{CE}$ in this text is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a Gram-negative bacterial infection in a patient, comprising the administration to said patient of a pharmaceutically active amount of a compound of formula I according to one of embodiments 1) to 39) or a pharmaceutically acceptable salt thereof. Accordingly, the invention provides a method for the prevention or the treatment of a bacterial infection caused by Gram-negative bacteria (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection caused by quinolone-resistant *Acinetobacter baumannii* quinolone-resistant bacteria or *Klebsiella pneumoniae* quinolone-resistant bacteria) in a patient, comprising the administration to said patient of a pharmaceutically active amount of a compound of formula I according to one of embodiments 1) to 39) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formula I as defined in embodiment 1), or further limited under consideration of their respective dependencies by the characteristics of any one of embodiments 2) to 39), and to pharmaceutically acceptable salts thereof. It relates furthermore to the use of such compounds as medicaments, especially for the prevention or treatment of a bacterial infection, in particular for the prevention or treatment of a bacterial infection caused by Gram-negative bacteria (notably for the prevention or treatment of a bacterial infection caused by *Acinetobacter baumannii* bacteria, *Escherichia coli* bacteria, *Klebsiella pneumoniae* bacteria or *Pseudomonas aeruginosa* bacteria, and in particular for the prevention or treatment of a bacterial infection caused by quinolone-resistant *Acinetobacter baumannii* quinolone-resistant bacteria or *Klebsiella pneumoniae* quinolone-resistant bacteria). The following embodiments relating to the compounds of formula I according to embodiment 1) are thus possible and intended and herewith specifically disclosed in individualised form:
1, 2+1, 3+1, 4+3+1, 5+4+3+1, 6+1, 6+2+1, 6+3+1, 6+4+3+1, 6+5+4+3+1, 7+1, 7+2+1, 7+3+1, 7+4+3+1, 7+5+4+3+1, 7+6+1, 7+6+2+1, 7+6+3+1, 7+6+4+3+1, 7+6+5+4+3+1, 8+7+1, 8+7+2+1, 8+7+3+1, 8+7+4+3+1,8+7+5+4+3+1,8+7+6+1,8+7+6+2+1,8+7+6+3+1,8+7+6+4+3+1,8+7+6+5+4+3+1,9+8+7+1, 9+8+7+2+1, 9+8+7+3+1, 9+8+7+4+3+1, 9+8+7+5+4+3+1, 9+8+7+6+1, 9+8+7+6+2+1, 9+8+7+6+3+1, 9+8+7+6+4+3+1, 9+8+7+6+5+4+3+1, 10+8+7+1, 10+8+7+2+1, 10+8+7+3+1, 10+8+7+4+3+1, 10+8+7+5+4+3+1, 10+8+7+6+1,10+8+7+6+2+1,10+8+7+6+3+1,10+8+7+6+4+3+1,10+8+7+6+5+4+3+1, 11+8+7+1, 11+8+7+2+1, 11+8+7+3+1, 11+8+7+4+3+1, 11+8+7+5+4+3+1, 11+8+7+6+1, 11+8+7+6+2+1, 11+8+7+6+3+1, 11+8+7+6+4+3+1, 11+8+7+6+5+4+3+1, 12+7+1, 12+7+2+1, 12+7+3+1, 12+7+4+3+1, 12+7+5+4+3+1, 12+7+6+1, 12+7+6+2+1, 12+7+6+3+1, 12+7+6+4+3+1, 12+7+6+5+4+3+1, 13+12+7+1, 13+12+7+2+1, 13+12+7+3+1, 13+12+7+4+3+1, 13+12+7+5+4+3+1, 13+12+7+6+1, 13+12+7+6+2+1, 13+12+7+6+3+1, 13+12+7+6+4+3+1, 13+12+7+6+5+4+3+1, 14+12+7+1, 14+12+7+2+1, 14+12+7+3+1, 14+12+7+4+3+1, 14+12+7+5+4+3+1, 14+12+7+6+1, 14+12+7+6+2+1, 14+12+7+6+3+1, 14+12+7+6+4+3+1, 14+12+7+6+5+4+3+1, 15+12+7+1, 15+12+7+2+1, 15+12+7+3+1, 15+12+7+4+3+1, 15+12+7+5+4+3+1, 15+12+7+6+1, 15+12+7+6+2+1, 15+12+7+6+3+1, 15+12+7+6+4+3+1, 15+12+7+6+5+4+3+1, 16+1, 16+2+1, 16+3+1, 16+4+3+1, 16+5+4+3+1, 16+6+1, 16+6+2+1, 16+6+3+1, 16+6+4+3+1, 16+6+5+4+3+1, 17+16+1, 17+16+2+1, 17+16+3+1, 17+16+4+3+1, 17+16+5+4+3+1, 17+16+6+1, 17+16+6+2+1, 17+16+6+3+1, 17+16+6+4+3+1, 17+16+6+5+4+3+1, 18+16+1, 18+16+2+1, 18+16+3+1, 18+16+4+3+1, 18+16+5+4+3+1, 18+16+6+1, 18+16+6+2+1, 18+16+6+3+1, 18+16+6+4+3+1, 18+16+6+5+4+3+1, 19+16+1, 19+16+2+1, 19+16+3+1, 19+16+4+3+1, 19+16+5+4+3+1, 19+16+6+1, 19+16+6+2+1, 19+16+6+3+1, 19+16+6+4+3+1, 19+16+6+5+4+3+1, 20+1, 20+2+1, 21+20+1, 21+20+2+1, 22+1, 22+2+1, 23+1, 23+2+1, 24+23+1, 24+23+2+1, 25+23+1, 25+23+2+1, 26+1, 26+2+1, 26+3+1, 26+4+3+1, 26+5+4+3+1, 26+6+1, 26+6+2+1, 26+6+3+1, 26+6+4+3+1, 26+6+5+4+3+1, 27+1, 27+2+1, 27+3+1, 27+4+3+1, 27+5+4+3+1, 27+6+1, 27+6+2+1, 27+6+3+1, 27+6+4+3+1, 27+6+5+4+3+1, 28+1, 28+2+1, 28+3+1, 28+4+3+1, 28+5+4+3+1, 28+6+1, 28+6+2+1, 28+6+3+1, 28+6+4+3+1, 28+6+5+4+3+1, 29+1, 29+2+1, 29+3+1, 29+4+3+1, 29+5+4+3+1, 29+6+1, 29+6+2+1, 29+6+3+1, 29+6+4+3+1, 29+6+5+4+3+1, 29+7+1, 29+7+2+1, 29+7+3+1, 29+7+4+3+1, 29+7+5+4+3+1, 29+7+6+1, 29+7+6+2+1, 29+7+6+3+1,29+7+6+4+3+1,29+7+6+5+4+3+1,29+8+7+1,29+8+7+2+1,29+8+7+3+1,29+8+7+4+3+1, 29+8+7+5+4+3+1,29+8+7+6+1,29+8+7+6+2+1,29+8+7+6+3+1,29+8+7+6+4+3+1,29+8+7+6+5+4+3+1, 29+9+8+7+1, 29+9+8+7+2+1, 29+9+8+7+3+1, 29+9+8+7+4+3+1, 29+9+8+7+5+4+3+1, 29+9+8+7+6+1, 29+9+8+7+6+2+1, 29+9+8+7+6+3+1, 29+9+8+7+6+4+3+1, 29+9+8+7+6+5+4+3+1, 29+10+8+7+1, 29+10+8+7+2+1, 29+10+8+7+3+1, 29+10+8+7+4+3+1, 29+10+8+7+5+4+3+1, 29+10+8+7+6+1, 29+10+8+7+6+2+1, 29+10+8+7+6+3+1, 29+10+8+7+6+4+3+1, 29+10+8+7+6+5+4+3+1, 29+11+8+7+1, 29+11+8+7+2+1, 29+11+8+7+3+1, 29+11+8+7+4+3+1, 29+11+8+7+5+4+3+1, 29+11+8+7+6+1, 29+11+8+7+6+2+1, 29+11+8+7+6+3+1, 29+11+8+7+6+4+3+1, 29+11+8+7+6+5+4+3+1, 29+12+7+1, 29+12+7+2+1, 29+12+7+3+1, 29+12+7+4+3+1, 29+12+7+5+4+3+1, 29+12+7+6+1, 29+12+7+6+2+1, 29+12+7+6+3+1, 29+12+7+6+4+3+1, 29+12+7+6+5+4+3+1, 29+13+12+7+1, 29+13+12+7+2+1, 29+13+12+7+3+1, 29+13+12+7+4+3+1, 29+13+12+7+5+4+3+1, 29+13+12+7+6+1, 29+13+12+7+6+2+1, 29+13+12+7+6+3+1, 29+13+12+7+6+4+3+1, 29+13+12+7+6+5+4+3+1, 29+14+12+7+1, 29+14+12+7+2+1, 29+14+12+7+3+1, 29+14+12+7+4+3+1, 29+14+12+7+5+4+3+1, 29+14+12+7+6+1, 29+14+12+7+6+2+1, 29+14+12+7+6+3+1, 29+14+12+7+6+4+3+1, 29+14+12+7+6+5+4+3+1, 29+15+12+7+1, 29+15+12+7+2+1, 29+15+12+7+3+1, 29+15+12+7+4+3+1, 29+15+12+7+5+4+3+1, 29+15+12+7+6+1, 29+15+12+7+6+2+1, 29+15+12+7+6+3+1, 29+15+12+7+6+4+3+1, 29+15+12+7+6+5+4+3+1, 29+16+1, 29+16+2+1, 29+16+3+1, 29+16+4+3+1, 29+16+5+4+3+1, 29+16+6+1, 29+16+6+2+1, 29+16+6+3+1, 29+16+6+4+3+1, 29+16+5+4+3+1, 29+17+16+1, 29+17+16+2+1, 29+17+16+3+1, 29+17+16+4+3+1, 29+17+16+5+4+3+1, 29+17+16+6+1, 29+17+16+6+2+1, 29+17+16+6+3+1, 29+17+16+6+4+3+1, 29+17+16+6+5+4+3+1, 29+18+16+1, 29+18+16+2+1, 29+18+16+3+1, 29+18+16+4+3+1, 29+18+16+5+4+3+1, 29+18+16+6+1, 29+18+16+6+2+1, 29+18+16+6+3+1, 29+18+16+6+4+3+1, 29+18+16+6+5+4+3+1, 29+19+16+1, 29+19+16+2+1, 29+19+16+3+1, 29+19+16+4+3+1, 29+19+16+5+4+3+1, 29+19+16+6+1, 29+19+16+6+2+1,29+19+16+6+3+1, 29+19+16+6+4+3+1,29+19+16+6+5+4+3+1,29+20+1,29+20+2+1, 29+21+20+1,29+21+20+2+1,29+22+1, 29+22+2+1, 29+23+1, 29+23+2+1, 29+24+23+1, 29+24+23+2+1, 29+25+23+1, 29+25+23+2+1, 29+26+1, 29+26+2+1, 29+26+3+1, 29+26+4+3+1, 29+26+5+4+3+1, 29+26+6+1, 29+26+6+2+1, 29+26+6+3+1, 29+26+6+4+3+1, 29+26+6+5+4+3+1, 29+27+1, 29+27+2+1, 29+27+3+1,29+27+4+3+1,29+27+5+4+3+1,29+27+6+1,29+27+6+2+1,29+27+6+3+1,29+27+6+4+3+1, 29+27+6+5+4+3+1, 29+28+1, 29+28+2+1, 29+28+3+1, 29+28+4+3+1, 29+28+5+4+3+1, 29+28+6+1, 29+28+6+2+1, 29+28+6+3+1, 29+28+6+4+3+1, 29+28+6+5+4+3+1, 30+1, 30+2+1, 30+3+1, 30+4+3+1, 30+5+4+3+1, 30+6+1, 30+6+2+1, 30+6+3+1, 30+6+4+3+1, 30+6+5+4+3+1, 30+7+1, 30+7+2+1, 30+7+3+1, 30+7+4+3+1, 30+7+5+4+3+1, 30+7+6+1, 30+7+6+2+1, 30+7+6+3+1, 30+7+6+4+3+1, 30+7+6+5+4+3+1, 30+8+7+1, 30+8+7+

2+1, 30+8+7+3+1, 30+8+7+4+3+1, 30+8+7+5+4+3+1, 30+8+7+6+1, 30+8+7+6+2+1, 30+8+7+6+3+1, 30+8+7+6+4+3+1, 30+8+7+6+5+4+3+1, 30+9+8+7+1, 30+9+8+7+2+1, 30+9+8+7+3+1, 30+9+8+7+4+3+1, 30+9+8+7+5+4+3+1, 30+9+8+7+6+1, 30+9+8+7+6+2+1, 30+9+8+7+6+3+1, 30+9+8+7+6+4+3+1, 30+9+8+7+6+5+4+3+1, 30+10+8+7+1, 30+10+8+7+2+1, 30+10+8+7+3+1, 30+10+8+7+4+3+1, 30+10+8+7+5+4+3+1, 30+10+8+7+6+1, 30+10+8+7+6+2+1, 30+10+8+7+6+3+1, 30+10+8+7+6+4+3+1, 30+10+8+7+6+5+4+3+1, 30+11+8+7+1, 30+11+8+7+2+1, 30+11+8+7+3+1, 30+11+8+7+4+3+1, 30+11+8+7+5+4+3+1, 30+11+8+7+6+1, 30+11+8+7+6+2+1, 30+11+8+7+6+3+1, 30+11+8+7+6+4+3+1, 30+11+8+7+6+5+4+3+1, 30+12+7+1, 30+12+7+2+1, 30+12+7+3+1, 30+12+7+4+3+1, 30+12+7+5+4+3+1, 30+12+7+6+1, 30+12+7+6+2+1, 30+12+7+6+3+1, 30+12+7+6+4+3+1, 30+12+7+6+5+4+3+1, 30+13+12+7+1, 30+13+12+7+2+1, 30+13+12+7+3+1, 30+13+12+7+4+3+1, 30+13+12+7+5+4+3+1, 30+13+12+7+6+1, 30+13+12+7+6+2+1, 30+13+12+7+6+3+1, 30+13+12+7+6+4+3+1, 30+13+12+7+6+5+4+3+1, 30+14+12+7+1, 30+14+12+7+2+1, 30+14+12+7+3+1, 30+14+12+7+4+3+1, 30+14+12+7+5+4+3+1, 30+14+12+7+6+1, 30+14+12+7+6+2+1, 30+14+12+7+6+3+1, 30+14+12+7+6+4+3+1, 30+14+12+7+6+5+4+3+1, 30+15+12+7+1, 30+15+12+7+2+1, 30+15+12+7+3+1, 30+15+12+7+4+3+1, 30+15+12+7+5+4+3+1, 30+15+12+7+6+1, 30+15+12+7+6+2+1, 30+15+12+7+6+3+1, 30+15+12+7+6+4+3+1, 30+15+12+7+6+5+4+3+1, 30+16+1, 30+16+2+1, 30+16+3+1, 30+16+4+3+1, 30+16+5+4+3+1, 30+16+6+1, 30+16+6+2+1, 30+16+6+3+1, 30+16+6+4+3+1, 30+16+6+5+4+3+1, 30+17+16+1, 30+17+16+2+1, 30+17+16+3+1, 30+17+16+4+3+1, 30+17+16+5+4+3+1, 30+17+16+6+1, 30+17+16+6+2+1, 30+17+16+6+3+1, 30+17+16+6+4+3+1, 30+17+16+6+5+4+3+1, 30+18+16+1, 30+18+16+2+1, 30+18+16+3+1, 30+18+16+4+3+1, 30+18+16+5+4+3+1, 30+18+16+6+1, 30+18+16+6+2+1, 30+18+16+6+3+1, 30+18+16+6+4+3+1, 30+18+16+6+5+4+3+1, 30+19+16+1, 30+19+16+2+1, 30+19+16+3+1, 30+19+16+4+3+1, 30+19+16+5+4+3+1, 30+19+16+6+1, 30+19+16+6+2+1,30+19+16+6+3+1,30+19+16+6+4+3+1,30+19+16+6+5+4+3+1,30+20+1,30+20+2+1, 30+21+20+1, 30+21+20+2+1, 30+22+1, 30+22+2+1, 30+23+1, 30+23+2+1, 30+24+23+1, 30+24+23+2+1, 30+25+23+1, 30+25+23+2+1, 30+26+1, 30+26+2+1, 30+26+3+1, 30+26+4+3+1, 30+26+5+4+3+1, 30+26+6+1, 30+26+6+2+1, 30+26+6+3+1, 30+26+6+4+3+1, 30+26+6+5+4+3+1, 30+27+1, 30+27+2+1, 30+27+3+1,30+27+4+3+1,30+27+5+4+3+1,30+27+6+1,30+27+6+2+1,30+27+6+3+1,30+27+6+4+3+1, 30+27+6+5+4+3+1, 30+28+1, 30+28+2+1, 30+28+3+1, 30+28+4+3+1, 30+28+5+4+3+1, 30+28+6+1, 30+28+6+2+1, 30+28+6+3+1, 30+28+6+4+3+1, 30+28+6+5+4+3+1, 31+1, 32+1, 32+2+1, 33+1, 33+2+1, 34+33+1, 34+33+2+1, 35+33+1, 35+33+2+1, 36+1, 36+2+1, 36+3+1, 36+4+3+1, 36+5+4+3+1, 36+6+1, 36+6+2+1, 36+6+3+1, 36+6+4+3+1, 36+6+5+4+3+1, 37+1, 37+2+1, 38+1, 39+1, 39+2+1, 40+1, 40+2+1, 40+3+1, 40+4+3+1, 40+5+4+3+1, 40+6+1, 40+6+2+1, 40+6+3+1, 40+6+4+3+1, 40+6+5+4+3+1, 40+7+1, 40+7+2+1, 40+7+3+1, 40+7+4+3+1, 40+7+5+4+3+1, 40+7+6+1, 40+7+6+2+1, 40+7+6+3+1, 40+7+6+4+3+1, 40+7+6+5+4+3+1, 40+8+7+1, 40+8+7+2+1, 40+8+7+3+1, 40+8+7+4+3+1, 40+8+7+5+4+3+1,40+8+7+6+1,40+8+7+6+2+1,40+8+7+6+3+1,40+8+7+6+4+3+1,40+8+7+6+5+4+3+1, 40+9+8+7+1, 40+9+8+7+2+1, 40+9+8+7+3+1, 40+9+8+7+4+3+1, 40+9+8+7+5+4+3+1, 40+9+8+7+6+1, 40+9+8+7+6+2+1, 40+9+8+7+6+3+1, 40+9+8+7+6+4+3+1, 40+9+8+7+6+5+4+3+1, 40+10+8+7+1, 40+10+8+7+2+1, 40+10+8+7+3+1, 40+10+8+7+4+3+1, 40+10+8+7+5+4+3+1, 40+10+8+7+6+1, 40+10+8+7+6+2+1, 40+10+8+7+6+3+1, 40+10+8+7+6+4+3+1, 40+10+8+7+6+5+4+3+1, 40+11+8+7+1, 40+11+8+7+2+1, 40+11+8+7+3+1, 40+11+8+7+4+3+1, 40+11+8+7+5+4+3+1, 40+11+8+7+6+1, 40+11+8+7+6+2+1, 40+11+8+7+6+3+1, 40+11+8+7+6+4+3+1, 40+11+8+7+6+5+4+3+1, 40+12+7+1, 40+12+7+2+1, 40+12+7+3+1, 40+12+7+4+3+1, 40+12+7+5+4+3+1, 40+12+7+6+1, 40+12+7+6+2+1, 40+12+7+6+3+1, 40+12+7+6+4+3+1, 40+12+7+6+5+4+3+1, 40+13+12+7+1, 40+13+12+7+2+1, 40+13+12+7+3+1, 40+13+12+7+4+3+1, 40+13+12+7+5+4+3+1, 40+13+12+7+6+1, 40+13+12+7+6+2+1, 40+13+12+7+6+3+1, 40+13+12+7+6+4+3+1, 40+13+12+7+6+5+4+3+1, 40+14+12+7+1, 40+14+12+7+2+1, 40+14+12+7+3+1, 40+14+12+7+4+3+1, 40+14+12+7+5+4+3+1, 40+14+12+7+6+1, 40+14+12+7+6+2+1, 40+14+12+7+6+3+1, 40+14+12+7+6+4+3+1, 40+14+12+7+6+5+4+3+1, 40+15+12+7+1, 40+15+12+7+2+1, 40+15+12+7+3+1, 40+15+12+7+4+3+1, 40+15+12+7+5+4+3+1, 40+15+12+7+6+1, 40+15+12+7+6+2+1, 40+15+12+7+6+3+1, 40+15+12+7+6+4+3+1, 40+15+12+7+6+5+4+3+1, 40+16+1, 40+16+2+1, 40+16+3+1, 40+16+4+3+1, 40+16+5+4+3+1, 40+16+6+1, 40+16+6+2+1, 40+16+6+3+1, 40+16+6+4+3+1, 40+16+6+5+4+3+1, 40+17+16+1, 40+17+16+2+1, 40+17+16+3+1, 40+17+16+4+3+1, 40+17+16+5+4+3+1, 40+17+16+6+1, 40+17+16+6+2+1, 40+17+16+6+3+1, 40+17+16+6+4+3+1, 40+17+16+6+5+4+3+1, 40+18+16+1, 40+18+16+2+1, 40+18+16+3+1, 40+18+16+4+3+1, 40+18+16+5+4+3+1, 40+18+16+6+1, 40+18+16+6+2+1, 40+18+16+6+3+1, 40+18+16+6+4+3+1, 40+18+16+6+5+4+3+1, 40+19+16+1, 40+19+16+2+1, 40+19+16+3+1, 40+19+16+4+3+1, 40+19+16+5+4+3+1, 40+19+16+6+1, 40+19+16+6+2+1,40+19+16+6+3+1,40+19+16+6+4+3+1,40+19+16+6+5+4+3+1,40+20+1,40+20+2+1, 40+21+20+1, 40+21+20+2+1, 40+22+1, 40+22+2+1, 40+23+1, 40+23+2+1, 40+24+23+1, 40+24+23+2+1, 40+25+23+1, 40+25+23+2+1, 40+26+1, 40+26+2+1, 40+26+3+1, 40+26+4+3+1, 40+26+5+4+3+1, 40+26+6+1, 40+26+6+2+1, 40+26+6+3+1, 40+26+6+4+3+1, 40+26+6+5+4+3+1, 40+27+1, 40+27+2+1, 40+27+3+1,40+27+4+3+1,40+27+5+4+3+1,40+27+6+1,40+27+6+2+1,40+27+6+3+1,40+27+6+4+3+1, 40+27+6+5+4+3+1, 40+28+1, 40+28+2+1, 40+28+3+1, 40+28+4+3+1, 40+28+5+4+3+1, 40+28+6+1, 40+28+6+2+1, 40+28+6+3+1, 40+28+6+4+3+1, 40+28+6+5+4+3+1, 40+29+1, 40+29+2+1, 40+29+3+1, 40+29+4+3+1, 40+29+5+4+3+1, 40+29+6+1, 40+29+6+2+1, 40+29+6+3+1, 40+29+6+4+3+1, 40+29+6+5+4+3+1, 40+29+7+1, 40+29+7+2+1, 40+29+7+3+1, 40+29+7+4+3+1, 40+29+7+5+4+3+1, 40+29+7+6+1, 40+29+7+6+2+1, 40+29+7+6+3+1, 40+29+7+6+4+3+1, 40+29+7+6+5+4+3+1, 40+29+8+7+1, 40+29+8+7+2+1, 40+29+8+7+3+1, 40+29+8+7+4+3+1, 40+29+8+7+5+4+3+1, 40+29+8+7+6+1,40+29+8+7+6+2+1,40+29+8+7+6+3+1,40+29+8+7+6+4+3+1,40+29+8+7+6+5+4+3+1, 40+29+9+8+7+1,40+29+9+8+7+2+1,40+29+9+8+7+3+1,40+29+9+8+7+4+3+1,40+29+9+8+7+5+4+3+1, 40+29+9+8+7+6+1, 40+29+9+8+7+6+2+1, 40+29+9+8+7+6+3+1, 40+29+9+8+7+6+4+3+1, 40+29+9+8+7+6+5+4+3+1, 40+29+10+8+7+1, 40+29+10+8+7+2+1, 40+29+10+8+7+3+1, 40+29+10+8+7+4+3+1, 40+29+10+8+7+5+4+3+1, 40+29+10+8+7+6+1, 40+29+10+8+7+6+2+1, 40+29+10+8+7+6+3+1, 40+29+10+8+7+6+4+3+1, 40+29+10+8+7+6+5+4+3+1, 40+29+11+8+7+1, 40+29+11+8+7+2+1, 40+29+11+8+7+3+1, 40+29+11+8+7+4+3+1, 40+29+11+8+7+5+4+3+1, 40+29+11+8+7+6+1, 40+29+11+8+7+6+2+1, 40+29+11+8+7+6+3+1, 40+29+11+8+7+6+4+3+1, 40+29+11+8+7+6+5+4+3+1, 40+29+12+7+1, 40+29+12+7+2+1, 40+29+12+7+3+1, 40+29+12+7+4+3+1, 40+29+12+7+5+4+3+1, 40+29+12+7+6+1, 40+29+12+7+6+2+1, 40+29+12+7+6+3+1, 40+29+12+7+

6+4+3+1, 40+29+12+7+6+5+4+3+1, 40+29+13+12+7+1, 40+29+13+12+7+2+1, 40+29+13+12+7+3+1, 40+29+13+12+7+4+3+1, 40+29+13+12+7+5+4+3+1, 40+29+13+12+7+6+1, 40+29+13+12+7+6+2+1, 40+29+13+12+7+6+3+1, 40+29+13+12+7+6+4+3+1, 40+29+13+12+7+6+5+4+3+1, 40+29+14+12+7+1, 40+29+14+12+7+2+1, 40+29+14+12+7+3+1, 40+29+14+12+7+4+3+1, 40+29+14+12+7+5+4+3+1, 40+29+14+12+7+6+1, 40+29+14+12+7+6+2+1, 40+29+14+12+7+6+3+1, 40+29+14+12+7+6+4+3+1, 40+29+14+12+7+6+5+4+3+1, 40+29+15+12+7+1, 40+29+15+12+7+2+1, 40+29+15+12+7+3+1, 40+29+15+12+7+4+3+1, 40+29+15+12+7+5+4+3+1, 40+29+15+12+7+6+1, 40+29+15+12+7+6+2+1, 40+29+15+12+7+6+3+1, 40+29+15+12+7+6+4+3+1, 40+29+15+12+7+6+5+4+3+1, 40+29+16+1, 40+29+16+2+1, 40+29+16+3+1, 40+29+16+4+3+1, 40+29+16+5+4+3+1, 40+29+16+6+1, 40+29+16+6+2+1, 40+29+16+6+3+1, 40+29+16+6+4+3+1, 40+29+16+6+5+4+3+1, 40+29+17+16+1, 40+29+17+16+2+1, 40+29+17+16+3+1, 40+29+17+16+4+3+1, 40+29+17+16+5+4+3+1, 40+29+17+16+6+1, 40+29+17+16+6+2+1, 40+29+17+16+6+3+1, 40+29+17+16+6+4+3+1, 40+29+17+16+6+5+4+3+1, 40+29+18+16+1, 40+29+18+16+2+1, 40+29+18+16+3+1, 40+29+18+16+4+3+1, 40+29+18+16+5+4+3+1, 40+29+18+16+6+1, 40+29+18+16+6+2+1, 40+29+18+16+6+3+1, 40+29+18+16+6+4+3+1, 40+29+18+16+6+5+4+3+1, 40+29+19+16+1, 40+29+19+16+2+1, 40+29+19+16+3+1, 40+29+19+16+4+3+1, 40+29+19+16+5+4+3+1, 40+29+19+16+6+1, 40+29+19+16+6+2+1, 40+29+19+16+6+3+1, 40+29+19+16+6+4+3+1, 40+29+19+16+6+5+4+3+1, 40+29+20+1, 40+29+20+2+1, 40+29+21+20+1, 40+29+21+20+2+1, 40+29+22+1, 40+29+22+2+1, 40+29+23+1, 40+29+23+2+1, 40+29+24+23+1, 40+29+24+23+2+1, 40+29+25+23+1, 40+29+25+23+2+1, 40+29+26+1, 40+29+26+2+1, 40+29+26+3+1, 40+29+26+4+3+1, 40+29+26+5+4+3+1, 40+29+26+6+1, 40+29+26+6+2+1, 40+29+26+6+3+1, 40+29+26+6+4+3+1, 40+29+26+6+5+4+3+1, 40+29+27+1, 40+29+27+2+1, 40+29+27+3+1, 40+29+27+4+3+1, 40+29+27+5+4+3+1, 40+29+27+6+1, 40+29+27+6+2+1, 40+29+27+6+3+1, 40+29+27+6+4+3+1, 40+29+27+6+5+4+3+1, 40+29+28+1, 40+29+28+2+1, 40+29+28+3+1, 40+29+28+4+3+1, 40+29+28+5+4+3+1, 40+29+28+6+1, 40+29+28+6+2+1, 40+29+28+6+3+1, 40+29+28+6+4+3+1, 40+29+28+6+5+4+3+1, 40+30+1, 40+30+2+1, 40+30+3+1, 40+30+4+3+1, 40+30+5+4+3+1, 40+30+6+1, 40+30+6+2+1, 40+30+6+3+1, 40+30+6+4+3+1, 40+30+6+5+4+3+1, 40+30+7+1, 40+30+7+2+1, 40+30+7+3+1, 40+30+7+4+3+1, 40+30+7+5+4+3+1, 40+30+7+6+1, 40+30+7+6+2+1, 40+30+7+6+3+1, 40+30+7+6+4+3+1, 40+30+7+6+5+4+3+1, 40+30+8+7+1, 40+30+8+7+2+1, 40+30+8+7+3+1, 40+30+8+7+4+3+1, 40+30+8+7+5+4+3+1, 40+30+8+7+6+1, 40+30+8+7+6+2+1, 40+30+8+7+6+3+1, 40+30+8+7+6+4+3+1, 40+30+8+7+6+5+4+3+1, 40+30+9+8+7+1, 40+30+9+8+7+2+1, 40+30+9+8+7+3+1, 40+30+9+8+7+4+3+1, 40+30+9+8+7+5+4+3+1, 40+30+9+8+7+6+1, 40+30+9+8+7+6+2+1, 40+30+9+8+7+6+3+1, 40+30+9+8+7+6+4+3+1, 40+30+9+8+7+6+5+4+3+1, 40+30+10+8+7+1, 40+30+10+8+7+2+1, 40+30+10+8+7+3+1, 40+30+10+8+7+4+3+1, 40+30+10+8+7+5+4+3+1, 40+30+10+8+7+6+1, 40+30+10+8+7+6+2+1, 40+30+10+8+7+6+3+1, 40+30+10+8+7+6+4+3+1, 40+30+10+8+7+6+5+4+3+1, 40+30+11+8+7+1, 40+30+11+8+7+2+1, 40+30+11+8+7+3+1, 40+30+11+8+7+4+3+1, 40+30+11+8+7+5+4+3+1, 40+30+11+8+7+6+1, 40+30+11+8+7+6+2+1, 40+30+11+8+7+6+3+1, 40+30+11+8+7+6+4+3+1, 40+30+11+8+7+6+5+4+3+1, 40+30+12+7+1, 40+30+12+7+2+1, 40+30+12+7+3+1, 40+30+12+7+4+3+1, 40+30+12+7+5+4+3+1, 40+30+12+7+6+1, 40+30+12+7+6+2+1, 40+30+12+7+6+3+1, 40+30+12+7+6+4+3+1, 40+30+12+7+6+5+4+3+1, 40+30+13+12+7+1, 40+30+13+12+7+2+1, 40+30+13+12+7+3+1, 40+30+13+12+7+4+3+1, 40+30+13+12+7+5+4+3+1, 40+30+13+12+7+6+1, 40+30+13+12+7+6+2+1, 40+30+13+12+7+6+3+1, 40+30+13+12+7+6+4+3+1, 40+30+13+12+7+6+5+4+3+1, 40+30+14+12+7+1, 40+30+14+12+7+2+1, 40+30+14+12+7+3+1, 40+30+14+12+7+4+3+1, 40+30+14+12+7+5+4+3+1, 40+30+14+12+7+6+1, 40+30+14+12+7+6+2+1, 40+30+14+12+7+6+3+1, 40+30+14+12+7+6+4+3+1, 40+30+14+12+7+6+5+4+3+1, 40+30+15+12+7+1, 40+30+15+12+7+2+1, 40+30+15+12+7+3+1, 40+30+15+12+7+4+3+1, 40+30+15+12+7+5+4+3+1, 40+30+15+12+7+6+1, 40+30+15+12+7+6+2+1, 40+30+15+12+7+6+3+1, 40+30+15+12+7+6+4+3+1, 40+30+15+12+7+6+5+4+3+1, 40+30+16+1, 40+30+16+2+1, 40+30+16+3+1, 40+30+16+4+3+1, 40+30+16+5+4+3+1, 40+30+16+6+1, 40+30+16+6+2+1, 40+30+16+6+3+1, 40+30+16+6+4+3+1, 40+30+16+6+5+4+3+1, 40+30+17+16+1, 40+30+17+16+2+1, 40+30+17+16+3+1, 40+30+17+16+4+3+1, 40+30+17+16+5+4+3+1, 40+30+17+16+6+1, 40+30+17+16+6+2+1, 40+30+17+16+6+3+1, 40+30+17+16+6+4+3+1, 40+30+17+16+6+5+4+3+1, 40+30+18+16+1, 40+30+18+16+2+1, 40+30+18+16+3+1, 40+30+18+16+4+3+1, 40+30+18+16+5+4+3+1, 40+30+18+16+6+1, 40+30+18+16+6+2+1, 40+30+18+16+6+3+1, 40+30+18+16+6+4+3+1, 40+30+18+16+6+5+4+3+1, 40+30+19+16+1, 40+30+19+16+2+1, 40+30+19+16+3+1, 40+30+19+16+4+3+1, 40+30+19+16+5+4+3+1, 40+30+19+16+6+1, 40+30+19+16+6+2+1, 40+30+19+16+6+3+1, 40+30+19+16+6+4+3+1, 40+30+19+16+6+5+4+3+1, 40+30+20+1, 40+30+20+2+1, 40+30+21+20+1, 40+30+21+20+2+1, 40+30+22+1, 40+30+22+2+1, 40+30+23+1, 40+30+23+2+1, 40+30+24+23+1, 40+30+24+23+2+1, 40+30+25+23+1, 40+30+25+23+2+1, 40+30+26+1, 40+30+26+2+1, 40+30+26+3+1, 40+30+26+4+3+1, 40+30+26+5+4+3+1, 40+30+26+6+1, 40+30+26+6+2+1, 40+30+26+6+3+1, 40+30+26+6+4+3+1, 40+30+26+6+5+4+3+1, 40+30+27+1, 40+30+27+2+1, 40+30+27+3+1, 40+30+27+4+3+1, 40+30+27+5+4+3+1, 40+30+27+6+1, 40+30+27+6+2+1, 40+30+27+6+3+1, 40+30+27+6+4+3+1, 40+30+27+6+5+4+3+1, 40+30+28+1, 40+30+28+2+1, 40+30+28+3+1, 40+30+28+4+3+1, 40+30+28+5+4+3+1, 40+30+28+6+1, 40+30+28+6+2+1, 40+30+28+6+3+1, 40+30+28+6+4+3+1, 40+30+28+6+5+4+3+1, 40+31+1, 40+32+1, 40+32+2+1, 40+33+1, 40+33+2+1, 40+34+33+1, 40+34+33+2+1, 40+35+33+1, 40+35+33+2+1.

In the list above, the numbers refer to the embodiments according to their numbering provided hereinabove whereas "+" indicates the dependency from another embodiment. The different individualised embodiments are separated by commas. In other words, "4+3+1" for example refers to embodiment 4) depending on embodiment 3), depending on embodiment 1), i.e. embodiment "4+3+1" corresponds to embodiment 1) further limited by the features of embodiments 3) and 4). Likewise, "13+12+7+1" refers to embodiment 13) depending mutatis mutandis on embodiments 12) and 7), depending on embodiment 1), i.e. embodiment "13+12+7+1" corresponds to embodiment 1) further limited by the features of embodiments 7) and 12), further limited by the features of embodiment 13).

The compounds of formula I can be manufactured in accordance with the present invention using the procedures described hereafter.

Preparation of the Compounds of Formula I

Abbreviations:
The following abbreviations are used throughout the specification and the examples:

| | |
|---|---|
| Ac | acetyl |
| AcOH | acetic acid |
| aq. | aqueous |
| Bs | 4-bromobenzenesulfonyl (brosylate) |
| BuLi | n-butyl lithium |
| CC | column chromatography over silica gel |
| Cipro | ciprofloxacin |
| Cy | cyclohexyl |
| DAD | diode array detection |
| dba | dibenzylideneacetone |
| DCC | dicyclohexylcarbodiimide |
| DCM | dichloromethane |
| DEA | diethylamine |
| DIPEA | diisopropylethylamine |
| DME | 1,2-dimethoxyethane |
| DMF | N,N-dimethylformamide |
| DMSO | dimethylsulfoxide |
| dppf | 1,1'-bis(diphenylphosphino)ferrocene |
| EA | ethyl acetate |
| EDC | N-(3-dimethylaminopropyl)-N'-ethylcarbodiimide hydrochloride |
| e.e. | enantiomeric excess |
| ELSD | evaporative light scattering detector |
| ESI | electron spray ionisation |
| eq. | equivalent |
| Et | ethyl |
| EtOH | ethanol |
| HATU | O-(7-azabenzotriazol-1-yl)-N,N,N',N'-tetramethyluronium hexafluorophosphate |
| Hept | heptane |
| Hex | hexane |
| HOBT | hydroxybenzotriazole |
| HPLC | high pressure liquid chromatography |
| IT | internal temperature |
| LC | liquid chromatography |
| Me | methyl |
| MeCN | acetonitrile |
| MeOH | methanol |
| MS | mass spectroscopy |
| Ms | methylsulfonyl (mesyl) |
| nBu | n-butyl |
| NBS | N-bromosuccinimide |
| Nf | nonafluorobutanesulfonyl |
| NMR | Nuclear Magnetic Resonance |
| Ns | 4-nitrobenzenesulfonyl (nosylate) |
| org. | organic |
| Pd/C | palladium on carbon |
| % w/w | percent by weight |
| PEPPSI™-IPr | [1,3-bis(2,6-diisopropylphenyl)imidazol-2-ylidene](3-chloropyridyl)palladium(II) dichloride |
| Ph | phenyl |
| PPTS | para-toluenesulfonic acid pyridinium salt |
| prep-HPLC | preparative high pressure liquid chromatography |
| Pyr | pyridine |
| quant. | quantitative |
| Q-phos | 1,2,3,4,5-pentaphenyl-1'-(di-tert-butylphosphino)-ferrocene |
| rt | room temperature |
| sat. | saturated |
| SK-CC01-A | 2'-(dimethylamino)-2-biphenylyl-palladium(II) chloride dinorbornylphosphine complex |
| S-Phos | 2-dicyclohexylphosphino-2',6'-dimethoxybiphenyl |
| TBAF | tetra-n-butylammonium fluoride |
| TBDMS | tert-butyldimethylsilyl |
| tBu | tert-butyl |
| TEA | triethylamine |
| Tf | trifluoromethylsulfonyl (triflyl) |
| TFA | trifluoroacetic acid |
| THF | tetrahydrofuran |
| THP | tetrahydropyranyl |
| TLC | thin layer chromatography |
| TMS | trimethylsilyl |
| TMSE | 2-(trimethylsilyl)ethyl |
| $t_R$ | retention time |
| Ts | para-toluenesulfonyl |

General Reaction Techniques:

General Reaction Technique 1 (Hydroxamic Acid Protecting Group Removal):

The protecting groups R of the hydroxamic acid ester derivatives (CONHOR) are removed as follows:

When R is THP, (2-methylpropoxy)ethyl, methoxymethyl, tBu, COOtBu or COtBu: by acidic treatment with e.g. TFA or HCl in an org. solvent such as DCM, dioxane, $Et_2O$ or MeOH between 0° C. and rt or by treatment with pyridinium para-toluenesulfonate in EtOH between rt and 80° C.;

When R is trityl: by treatment with diluted acid such as citric acid or HCl in an org. solvent such as MeOH or DCM;

When R is benzyl: by hydrogenation using general reaction technique 5;

When R is TMSE: by using fluoride anion sources such as $BF_3$.etherate complex in MeCN at 0° C., TBAF in THF between 0° C. and +40° C. or HF in MeCN or water between 0° C. and +40° C., or using acidic conditions such as AcOH in THF/MeOH or HCl in MeOH;

When R is allyl: by treatment with $Pd(PPh_3)_4$ in a solvent such as MeOH in presence of $K_2CO_3$ or a scavenger such as dimedone, morpholine or tributyltin hydride;

When R is COMe: by treatment with diluted NaOH or $Na_2CO_3$ in a solvent such as MeOH.

Further general methods to remove hydroxamic acid protecting groups have been described in T. W. Greene and P. G. M. Wuts, *Protecting Groups in Organic Synthesis,* $3^{rd}$ Ed (1999), 23-147 (Publisher: John Wiley and Sons, Inc., New York, N.Y.).

General Reaction Technique 2 (Amide Coupling):

The carboxylic acid is reacted with the hydroxylamine derivative in the presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and 60° C. (see G. Benz in *Comprehensive Organic Synthesis,* B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and 60° C. Further activating agents can be found in *Comprehensive Organic Transformations. A guide to Functional Group Preparations;* $2^{nd}$ Edition (1999), R. C. Larock, Wiley-VC; New York, Chichester, Weinheim, Brisbane, Singapore, Toronto; Section nitriles, carboxylic acids and derivatives, p. 1941-1949.

General Reaction Technique 3 (Suzuki Coupling):

The aromatic halide (typically a bromide) is reacted with the required boronic acid derivative or its boronate ester equivalent (e.g. pinacol ester) in the presence of a palladium catalyst and a base such as $K_2CO_3$, $Cs_2CO_3$, $K_3PO_4$, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as Pd(PPh₃)₄. These catalysts can also be prepared in situ from a common palladium source such as Pd(OAc)₂ or Pd₂(dba)₃ and a ligand such as trialkylphosphines (e.g. PCy₃ or P(tBu)₃), dialkylphosphinobiphenyls (e.g. S-Phos) or ferrocenylphosphines (e.g. Q-phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in Miyaura and Suzuki, *Chem. Rev.* (1995), 95, 2457-2483, Bellina et al., *Synthesis* (2004), 2419-2440, Mauger and Mignani, *Aldrichimica Acta* (2006), 39, 17-24, Kantchev et al., *Aldrichimica Acta* (2006), 39, 97-111, Fu, *Acc. Chem. Res.* (2008), 41, 1555-1564, and references cited therein.

General Reaction Technique 4 (Alkyne-Alkyne Cross Coupling or Alkyne-Haloalkyne Cross Coupling):

An alkyne derivative is coupled with a second alkyne or a haloalkyne derivative, using a catalytic amount of a palladium salt, an org. base such as TEA and a catalytic amount of a copper derivative (usually copper iodide) in a solvent such as DMF between 20° C. to 100° C. (see Sonogashira, K. in *Metal-Catalyzed Reactions*, Diederich, F., Stang, P. J., Eds.; Wiley-VCH, New York (1998)). Alternatively, the alkyne-haloalkyne cross coupling reaction can be performed using only a catalytic amount of copper derivative in presence of aqueous hydroxylamine and a base such as piperidine or pyrrolidine (see Chodkiewicz and Cadiot, *C. R. Hebd. Seances Acad. Sci.* (1955), 241, 1055-1057).

General Reaction Technique 5 (Hydrogenation of a Double Bond):

The unsaturated derivative dissolved in a solvent such as MeOH, EA or THF is hydrogenated over a noble metal catalyst such as Pd/C or PtO₂, or over Raney Ni. At the end of the reaction the catalyst is filtered off and the filtrate is evaporated under reduced pressure. Alternatively the reduction can be performed by catalytic transfer hydrogenation using Pd/C and ammonium formate as hydrogen source.

General Reaction Technique 6 (Transformation of an Ester into an Acid):

When the ester side chain is a linear alkyl, the hydrolysis is usually performed by treatment with an alkali hydroxide such as LiOH, KOH or NaOH in a water-dioxan or water-THF mixture between 0° C. and 80° C. When the ester side chain is tBu, the release of the corresponding acid can also be performed in neat TFA or diluted TFA or HCl in an org. solvent such as ether or THF. When the ester side chain is the allyl group, the reaction is performed in the presence of tetrakis(triphenylphosphine)palladium(0) in the presence of an allyl cation scavenger such as morpholine, dimedone or tributyltin hydride between 0° C. and 50° C. in a solvent such as THF. When the ester side chain is benzyl, the reaction is performed under hydrogen in the presence of a noble metal catalyst such as Pd/C in a solvent such as MeOH, THF or EA. Further strategies to introduce other acid protecting groups and general methods to remove them have been described in T. W. Greene and P. G. M. Wuts, *Protecting Groups in Organic Synthesis*, 3rd Ed. (1999), 369-441 (Publisher: John Wiley and Sons, Inc., New York, N.Y.).

General Reaction Technique 7 (Alcohol Activation)

The alcohol is reacted with MsCl, TfCl, BsCl, NfCl, NsCl or TsCl in the presence of a base such as TEA in a dry aprotic solvent such as Pyr, THF or DCM between −30° C. and +50° C. In the case of the triflate or mesylate, Tf₂O or Ms₂O can also be used.

General Reaction Technique 8 (Formation of Iodo, Chloro or Bromo Derivatives):

The sulfonates obtained using general reaction technique 7 can be reacted with a sodium halogenide such as NaI or NaBr in MeCN or DMF between 40° C. and 120° C., delivering the corresponding halogenated derivatives. Alternatively, the corresponding bromides or chlorides can also be obtained by reaction of the corresponding alcohol derivatives with PBr₃ or PCl₃ respectively.

General Preparation Methods:
Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

The sections hereafter describe general methods for preparing compounds of formula I. If not indicated otherwise, the generic groups X, R¹, R², M, M^A, M^B, A, R^{1A}, R^{2A}, R^{3A} and R^{1B} are as defined for formula I. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

The compounds of formula I can be obtained by deprotecting a compound of formula II

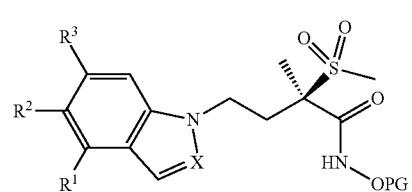

II wherein R¹, R² and R³ have the same meanings as in formula I and PG represents THP, TMSE, benzyl, trityl, (2-methylpropoxy)ethyl, methoxymethyl, allyl, tBu, acetyl, COOtBu or COtBu using general reaction technique 1. The reaction can also be performed with racemic material and the (R) enantiomer can be obtained by chiral HPLC separation.

If desired, the compounds of formula I thus obtained may be converted into their salts, and notably into their pharmaceutically acceptable salts using standard methods.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in the presence or absence of an amine such as TEA or diethylamine) and eluent B (Hex), at a flow rate of 0.8 to 150 mL/min.

Preparation of the Compounds of Formula II:

The compounds of formula II can be obtained by:

a) reacting a compound of formula III

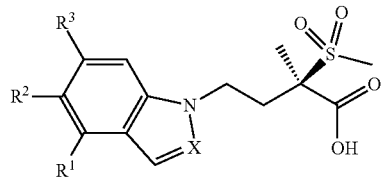

wherein X, $R^1$, $R^2$ and $R^3$ have the same respective meanings as in formula I with a compound of formula IV

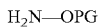

wherein PG has the same meaning as in formula II using general reaction technique 2 (this reaction can also be performed with racemic compound of formula III and the (R)-enantiomer can then be obtained by chiral HPLC separation of the reaction product); or b) reacting a boron derivative of formula V

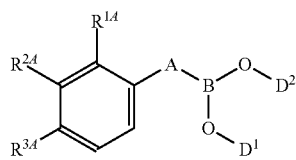

wherein $R^{1A}$, $R^{2A}$ and $R^{3A}$ have the same respective meanings as in formula I, A represents a bond or CH=CH and $D^1$ and $D^2$ represent H, methyl or ethyl or $D^1$ and $D^2$ together represent $CH_2C(Me)_2CH_2$ or $C(Me)_2C(Me)_2$ with a compound of formula VI

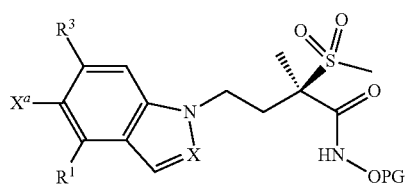

wherein $R^1$ and $R^3$ have the same respective meanings as in formula I, $X^a$ represents a halogen such as bromine or iodine and PG has the same meaning as in formula II, using general reaction technique 3 (this reaction can also be performed with racemic compound of formula VI and the (R)-enantiomer can then be obtained by chiral HPLC separation of the reaction product); or c) reacting a compound of formula VII

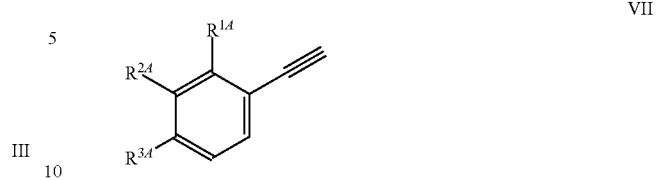

wherein $R^{1A}$, $R^{2A}$ and $R^{3A}$ have the same respective meanings as in formula I, with a compound of formula VI as defined in section b) above wherein $X^a$ represents iodine, using general reaction technique 4 (this reaction can also be performed with racemic compound of formula VI and the (R)-enantiomer can then be obtained by chiral HPLC separation of the reaction product); or d) reacting a compound of formula VIII

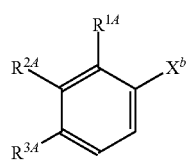

wherein $R^{1A}$, $R^{2A}$ and $R^{3A}$ have the same respective meanings as in formula I and $X^b$ represents iodine or bromine (and preferably iodine), with a compound of formula VIa

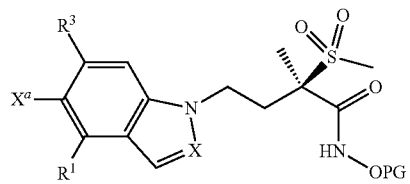

wherein X, $R^1$ and $R^3$ have the same respective meanings as in formula I, $X^a$ represents ethynyl and PG has the same meaning as in formula II, using general reaction technique 4 (this reaction can also be performed with racemic compound of formula VIa and the (R)-enantiomer can then be obtained by chiral HPLC separation of the reaction product); or e) reacting a compound of formula IX

wherein $R^{1B}$ has the same meaning as in formula I and $X^c$ represents iodine or bromine (and preferably iodine), with a compound of formula VIa as defined in section d) above, using general reaction technique 4 (this reaction can also be performed with racemic compound of formula VIa and the (R)-enantiomer can then be obtained by chiral HPLC separation of the reaction product); or f) hydrogenating a compound of formula X

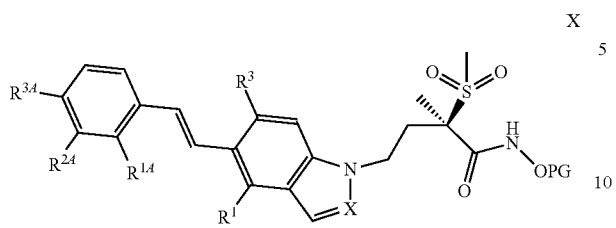

wherein X, $R^1$, $R^3$, $R^{1A}$, $R^{2A}$ and $R^{3A}$ have the same respective meanings as in formula I and PG has the same meaning as in formula II, using general reaction technique 5 (this reaction can also be performed with racemic compound of formula X and the (R)-enantiomer can then be obtained by chiral HPLC separation of the reaction product).

Preparation of the Synthesis Intermediates of Formulae III, IV V, I, VIa VII, VIII, IX and X:

Compounds of Formula III:

The compounds of formula III can be prepared as summarised in Scheme 1 hereafter.

Scheme 1

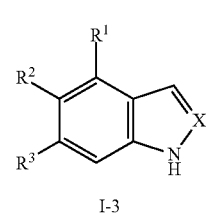

I-3

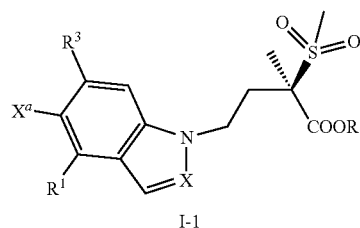

I-1

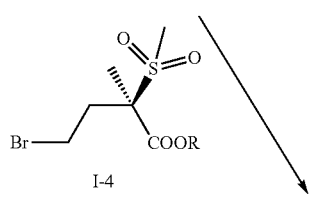

I-4

V, VII

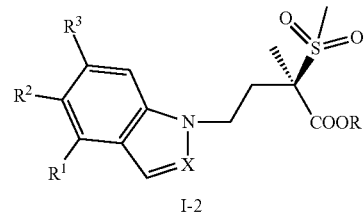

I-2

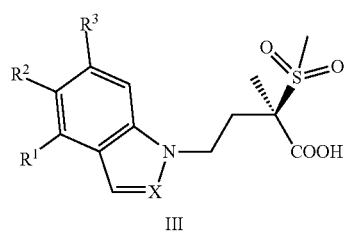

III

In Scheme 1, X, $R^1$, $R^2$ and $R^3$ have the same respective meanings as in formula I, $X^a$ represents a halogen such as iodine or bromine and R represents ($C_1$-$C_5$)alkyl, allyl or benzyl. The reactions can also be performed with racemic material and the (R)-enantiomer can be obtained by chiral HPLC separation at any step when suitable.

The derivatives of formula I-1 can be reacted (Scheme 1) with the boronic acid or ester derivatives of formula V using general reaction technique 3 ($X^a$ represents bromine or iodine) or with the alkyne derivatives of formula VII using general reaction technique 4 ($X^a$ representing iodine), affording the derivatives of formula I-2. Alternatively the latter can also be obtained by reacting the derivatives of formula I-3 with the bromo derivatives of formula I-4 in the presence of a base such as sodium hydride in an aprotic solvent such as DMF, at a temperature ranging between 0° C. and 60° C. The compounds of formula I-2 can be transformed into the carboxylic acid derivatives of formula III using general reaction technique 6.

Compounds of Formula IV:

The compounds of formula IV are commercially available (PG=THP, tBu, COOtBu or allyl) or can be prepared according to WO 2010/060785 (PG=(2-methylpropoxy)ethyl) or Marmer and Maerker, *J. Org. Chem.* (1972), 37, 3520-3523 (PG=COtBu).

Compounds of Formula V:

The compounds of formula V wherein A is a bond and $D^1$ and $D^2$ each represent H or ($C_1$-$C_2$)alkyl are commercially available or can be prepared according to Sleveland et al., *Organic Process Research & Development* (2012), 16, 1121-1130 starting from tri(($C_1$-$C_2$)alkyl)borate and the corresponding commercially available bromo derivatives (optionally followed by acidic hydrolysis). The compounds of formula V wherein A represents a bond and $D^1$ and $D^2$ together represent $CH_2C(Me)_2CH_2$ or $C(Me)_2C(Me)_2$ are commercially available or can be prepared according to WO 2012/093809, starting from bis(pinacolato)diborane or 5,5-dimethyl-1,3,2-dioxaborinane (both commercially available) with the corresponding commercially available bromo derivatives of formula VIII. The compounds of formula V wherein A is CH=CH and $D^1$ and $D^2$ each represent H are commercially available or can be prepared according to Perner et al., *Biorg. Med. Chem. Lett.* (2005), 15, 2803-2807 by reaction of catechol borane on the appropriate alkyne derivatives followed by acidic hydrolysis.

Compounds of Formulae VI and VIa:

The compounds of formulae VI and VIa can be prepared as summarised in Scheme 2 hereafter.

Scheme 2

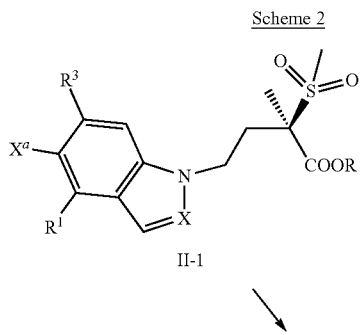

II-1

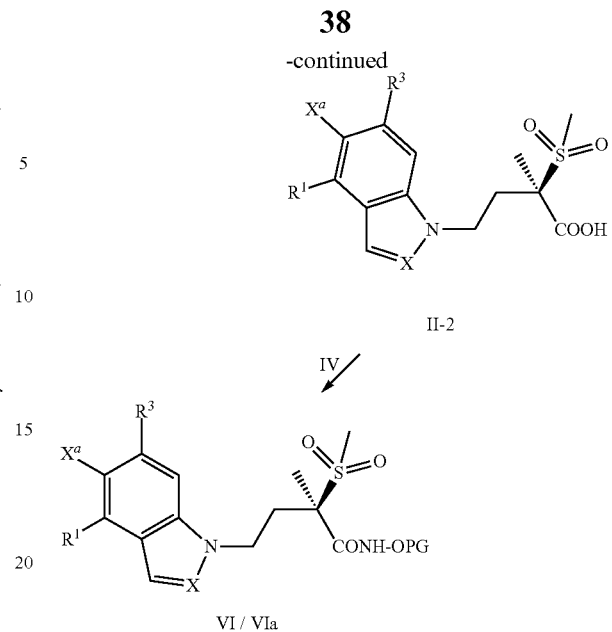

In Scheme 2, X, $R^1$ and $R^3$ have the same respective meanings as in formula I, R represents ($C_1$-$C_5$)alkyl, allyl or benzyl, $X^a$ represents a halogen (such as iodine or bromine) or ethynyl and PG has the same meaning as in formula II. The reactions can also be performed with racemic material and the (R)-enantiomer can be obtained by chiral HPLC separation at any step when suitable.

The derivatives of formula II-1 can be transformed (Scheme 2) into the carboxylic acid derivatives of formula II-2 using general reaction technique 6 and further reacted with the compounds of formula IV using general reaction technique 2, thus affording the compounds of formula VI ($X^a$=halogen) or VIa ($X^a$=ethynyl).

Compounds of Formula VII:

The compounds of formula VII are commercially available or can be prepared as summarised in Scheme 3 hereafter.

Scheme 3

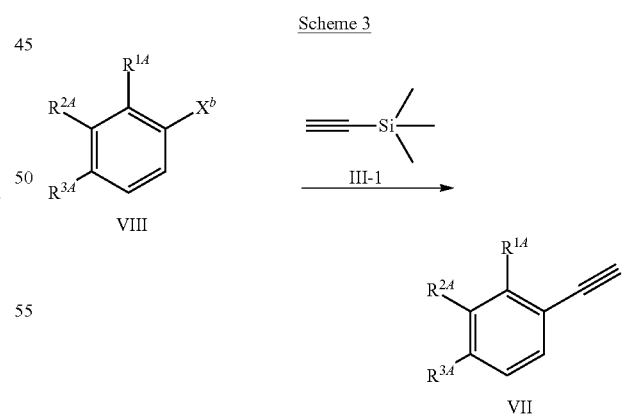

In Scheme 3, $R^{1A}$, $R^{2A}$ and $R^{3A}$ have the same respective meanings as in formula I and $X^b$ represents a halogen such as bromine or iodine.

The derivatives of formula VIII wherein $X^b$ represents bromine can be transformed (Scheme 3) into the corresponding derivatives wherein $X^b$ represents iodine by reaction with NaI in presence CuI and trans-N,N'-dimethylcyclohexanediamine. The resulting compounds of formula VIII wherein $X^b$ represents iodine can be reacted with trimethylsilylacetylene (III-1) in the presence of CuI and PdCl$_2$(PPh$_3$)$_2$ followed by treatment with an inorganic base such as K$_2$CO$_3$ in an appropriate alcoholic solvent such as MeOH, or by treatment with TBAF in THF, affording the derivatives of formula VII.

Compounds of Formula VIII:

The compounds of formula VIII wherein $X^b$ represents bromine are commercially available or can be prepared by standard methods known to one skilled in the art. The compounds of formula VIII wherein $X^b$ represents iodine can be obtained from the corresponding bromine derivatives by reaction with NaI in the presence of a copper (I) salt and a ligand such as trans-N,N'-dimethylcyclohexa-1,2-diamine in a solvent such as dioxane at a temperature ranging between rt and 100° C., or in a microwave oven at 150° C.

Compounds of Formula IX:

The compounds of formula IX wherein $X^c$ represents iodine can be prepared by iodination of the corresponding compounds wherein $X^c$ would be H with iodine in the presence of an inorganic base such as KOH.

Compounds of Formula X:

The compounds of formula X can be prepared by analogy to the method described in sub-section b) of the section entitled "Preparation of the compounds of formula II".

Other Synthesis Intermediates and Starting Materials

The compounds of formula I-1 wherein $X^a$ represents bromine can be prepared as summarised in Scheme 4 hereafter.

The compounds of formula IV-1 can be reacted with 1,3-dioxolan-2-one (IV-2) in the presence of NaH, affording (after separation of the isomeric 2-(2H-indazol-2-yl)ethanol derivatives in case X is N) the compounds of formula IV-3. The compounds of formula IV-5 can be sequentially transformed into the derivatives of formulae IV-4 and IV-5 using general reaction techniques 7 and 8 respectively. The compounds of formula IV-5 can be reacted either with the (C$_1$-C$_3$)alkyl 2-(methylsulfonyl)acetate derivatives of formula IV-6 in the presence of NaH, followed by alkylation with MeI in the presence of NaH, or directly with a 2-(methylsulfonyl)propanoate derivative of formula IV-7 in the presence of NaH, affording the compounds of formula I-1 wherein $X^a$ represents bromine. The (R)-configurated compounds of formula I-1 can also be obtained by direct alkylation of the compounds of formula IV-1 with the chiral bromide of formula IV-8.

The compounds of formula I-1 wherein $X^a$ represents bromine can be transformed into the compounds of formula I-1 wherein $X^a$ represents iodine by reaction with NaI in the presence of CuI and trans-N,N-dimethylcyclohexanediamine.

The compounds of formula II-1 wherein $X^a$ represents an ethynyl group can be prepared from the compounds of formula I-1 wherein $X^a$ represents bromine by reaction with NaI in the presence of CuI and trans-N,N'-dimethylcyclohexanediamine. The resulting compounds of formula I-1 wherein $X^a$ represents iodine can be reacted with trimethylsilylacetylene in the presence of CuI and PdCl$_2$(PPh$_3$)$_2$, followed by treatment with an inorganic base such as K$_2$CO$_3$ in an appropriate alcoholic solvent such as MeOH, or by treatment with TBAF in THF.

The compounds of formulae III-1, IV-2, IV-6 and IV-7 and the compounds of formula IV-1 wherein X is CH are commercially available or can be prepared by standard methods known to one skilled in the art.

The compounds of formula IV-1 wherein X is N are commercially available or can be prepared as summarised in Scheme 5 hereafter.

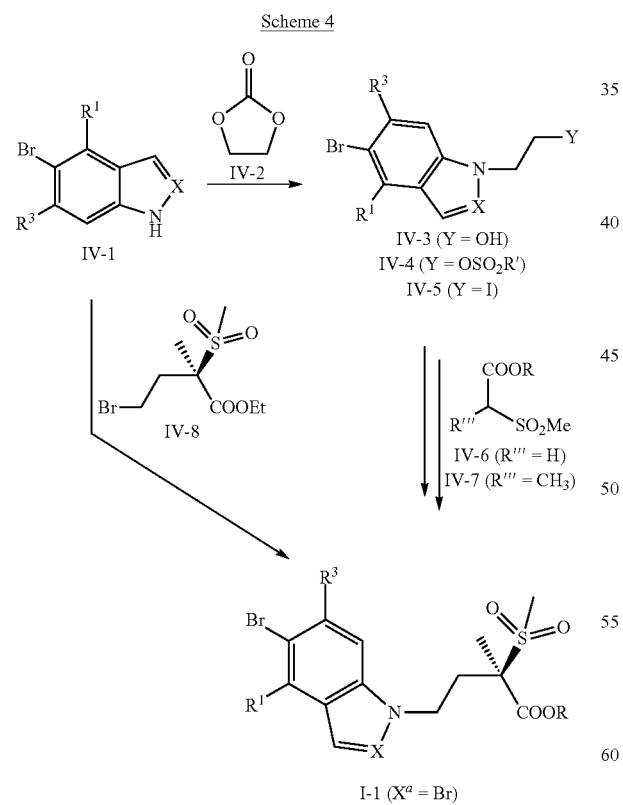

Scheme 4

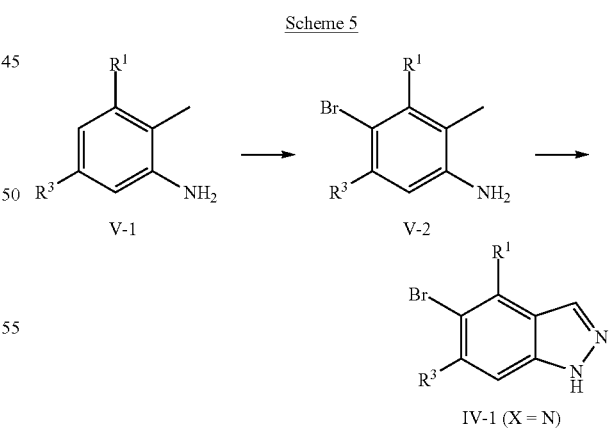

Scheme 5

In Scheme 4, X, R$^1$ and R$^3$ have the same meanings as in formula I, R represents (C$_1$-C$_5$)alkyl, allyl or benzyl and Y represents I, OH or OSO$_2$R' wherein R' represents Me, CF$_3$ or tolyl.

In Scheme 5, R$^1$ and R$^3$ have the same meanings as in formula I.

The compounds of formula V-1 can be reacted (Scheme 5) with NBS, affording the derivatives of formula V-2. The latter can be reacted as described in WO 2012/037410 with NaNO$_2$ in the presence of AcOH, affording the indazole derivatives of formula IV-1 wherein X is N.

The chiral compound of formula IV-8 can be prepared as described in WO 2012/137099.

The compounds of formula V-1 are commercially available or can be prepared by standard methods known to one skilled in the art.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt.

Analytical TLC characterisations were performed with 0.2 mm plates: Merck, Silica gel 60 $F_{254}$. Elution is performed with EA, Hept, DCM, MeOH or mixtures thereof. Detection was done with UV or with a solution of $KMnO_4$ (3 g), $K_2CO_3$ (20 g), 5% NaOH (3 mL) and $H_2O$ (300 mL) with subsequent heating.

CCs were performed using Brunschwig 60A silica gel (0.032-0.63 mm) or using an ISCO CombiFlash system and prepacked $SiO_2$ cartridges, elution being carried out with either Hept-EA or DCM-MeOH mixtures with an appropriate gradient. When the compounds contained an acid function, 1% of AcOH was added to the eluent(s). When the compounds contained a basic function, 25% aq. $NH_4OH$ was added to the eluents.

The compounds were characterized by $^1$H-NMR (300 MHz, Varian Oxford; 400 MHz, Bruker Avance 400 or 500 MHz, Bruker Avance 500 Cryoprobe). Chemical shifts δ are given in ppm relative to the solvent used; multiplicities: s=singlet, d=doublet, t=triplet, q=quartet, p=pentet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point.

The analytical LC-MS data have been obtained using the following respective conditions:
Column: Zorbax SB-Aq, 30.5 μm, 4.6×50 mm;
Injection volume: 1μL;
Column oven temperature: 40° C.;
Detection: UV 210 nm, ELSD and MS;
MS ionization mode: ESI+;
Eluents: A: $H_2O$+0.04% TFA; and B: MeCN;
Flow rate: 40.5 mL/min;
Gradient: 5% B to 95% B (0.0 min-1.0 min), 95% B (1.0 min-1.45 min).

The number of decimals given for the corresponding [M+H$^+$] peak(s) of each tested compound depends upon the accuracy of the LC-MS device actually used.

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following respective conditions:
Method 1:
Column: Waters Atlantis T3 OBD, 10 m, 30×75 mm;
Flow rate: 75 mL/min;
Eluents: A: $H_2O$+0.1% HCOOH; B: MeCN+0.1% HCOOH;
Gradient: 90% A to 5% A (0.0 min-4.0 min), 5% A (4.0 min-6.0 min).

Method 2:
Column: Waters XBridge C18, 10 m, 30×75 mm;
Flow rate: 75 mL/min;
Eluents: A: $H_2O$+0.1% HCOOH; B: MeCN+0.1% HCOOH;
Gradient: 70% A to 5% A (0.0 min-3.5 min), 5% A (3.5 min-6.0 min).

Besides, semi-preparative chiral HPLCs were performed using the conditions hereafter.
Semi-Preparative Chiral HPLC Method A:
The semi-preparative chiral HPLC is performed on a Daicel ChiralPak AS-H column (20×250 mm, 5 μM) using the eluent mixture, flow rate and detection conditions indicated between brackets in the corresponding experimental protocol. The retention times are obtained by elution of analytical samples on a Daicel ChiralPak AS-H column (4.6×250 mm, 5 μM) using the same eluent mixture with the flow rate indicated between brackets in the corresponding experimental protocol.
Semi-Preparative Chiral HPLC Method B:
The semi-preparative chiral HPLC is performed on a Daicel ChiralPak AY-H column (20×250 mm, 5 μM) using the eluent mixture, flow rate and detection conditions indicated between brackets in the corresponding experimental protocol. The retention times are obtained by elution of analytical samples on a Daicel ChiralPak AY-H column (4.6×250 mm, 5 μM) using the same eluent mixture with the flow rate indicated between brackets in the corresponding experimental protocol.
Semi-Preparative Chiral HPLC Method C:
The semi-preparative chiral HPLC is performed on a Daicel ChiralCel OJ-H column (20×250 mm; 5 μM) using the eluent mixture, flow rate and detection conditions indicated between brackets in the corresponding experimental protocol. The retention times are obtained by elution of analytical samples on a Daicel ChiralCel OJ-H column (4.6×250 mm; 5 μM) using the same eluent mixture with the flow rate indicated between brackets in the corresponding experimental protocol.

PREPARATIONS

Preparation A (RS)-4-(5-bromo-1H-indazol-1-yl)-2-yl-2-methylsulfonyl)-N-((tetrahydro-2H-pyran-2-yl)oxy)butanamide A.i. 2-(5-bromo-1H-indazol-1-yl)ethanol A solution of 5-bromo-1H-indazole (10 g; commercial) in DMF (330 mL) was cooled to 0° C. and treated portion wise with NaH (in 60% mineral oil; 2.41 g). The reaction mixture was allowed to reach rt, further stirred at rt for 1 h, treated with ethylene carbonate (17.9 g) and heated for 3 h at 80° C. The reaction mixture was concentrated under reduced pressure, diluted with 10% aq. $NaHSO_4$ solution (150 mL) and extracted with EA (2×50 mL). The combined org. layers were washed with brine, dried over $Na_2SO_4$, concentrated under reduced pressure and purified by CC (Hept-EA) to afford the title compound, contaminated with ethylene carbonate, as a yellow oil (10.71 g).

$^1$H NMR (d6-DMSO) δ: 8.02 (s, 1H); 7.96 (d, J=1.5 Hz, 1H); 7.63 (dd, J=1.8, 8.9 Hz, 1H); 7.46 (dd, J=1.8, 8.9 Hz,

1H); 4.82 (t, J=5.4 Hz, 1H); 4.41 (t, J=5.5 Hz, 2H); 3.77 (q, J=5.4 Hz, 2H).

MS (ESI, m/z): 243.0 [M+H+] for $C_9H_9N_2OBr$; $t_R$=0.68 min.

A.ii. 3-(5-bromo-1H-indazol-1-yl)ethyl methanesulfonate

A solution of intermediate A.i (10.71 g) in DCM (240 mL) and TEA (15 mL) was cooled to 0° C. and treated with MsCl (5.5 mL). The reaction mixture was stirred at 0° C. for 30 min, allowed to reach rt and treated with sat. aq. $Na_2CO_3$ solution (100 mL). The org. layer was washed with a sat. aq. $NaHCO_3$ solution, dried over $Na_2SO_4$ and concentrated under reduced pressure to afford the title compound as a crude yellow oil (21.6 g).

MS (ESI, m/z): 320.9 [M+H$^+$] for $C_{10}H_{11}N_2O_3BrS$; $t_R$=0.78 min.

A.iii. 5-bromo-1-(3-iodoethyl)-1H-indazole

NaI (13.7 g) was added to a solution of intermediate A.ii (21.6 g) in 2-butanone (202 mL). The reaction mixture was stirred at 80° C. for 2 h. The reaction mixture was diluted with water (45 mL) and EA (75 mL). The aq. layer was extracted with EA (4×30 mL). The combined org. layers were washed with a sat. solution of $Na_2SO_3$ (75 mL) and brine (45 mL), dried over $Na_2SO_4$, filtered and concentrated to dryness. The residue was purified by CC (EA-Hept) to afford the title compound as a yellow solid (10.87 g).

$^1$H NMR (d6-DMSO) δ: 8.1 (s, 1H); 7.99 (d, J=1.9 Hz, 1H); 7.73 (dd, J=1.9, 9.1 Hz, 1H); 7.50 (dd, J=1.9, 9.1 Hz, 1H); 4.77 (t, J=6.4 Hz, 2H); 3.64 (t, J=6.4 Hz, 2H).

MS (ESI, m/z): 350.84 [M+H$^+$] for $C_9H_9N_2BrI$; $t_R$=0.90 min.

A.iv. (RS)-ethyl 4-(5-bromo-1H-indazol-1-yl)-2-(methylsulfonyl)butanoate

To a suspension of NaH (0.86 g; 21.5 mmol) in DMF (30 mL) at 0° C. was added slowly ethyl methylsulfonyl acetate (5 mL; 36.8 mmol). The reaction was allowed to warm to rt and stirred for 30 min. A solution of intermediate A.iii (5 g; 14.2 mmol) in DMF (75 mL) was added dropwise and the reaction mixture was stirred at rt overnight. An aq. 20% $NaHSO_4$ solution (25 mL) was added and the mixture was extracted with EA (3×40 mL). The combined org. layers were washed with brine (25 mL), dried over $MgSO_4$ and concentrated to dryness. The crude product was purified by CC (Hept-EA) to afford the title compound (still contaminated with the excess of ethylmethylsulfonyl acetate) as a yellow oil (8.21 g).

$^1$H NMR (d6-DMSO) δ: 8.05 (d, J=0.9 Hz, 1H); 7.99 (dd, J=0.9, 1.9 Hz, 1H); 7.63 (d, J=9.1 Hz, 1H); 7.52 (dd, J=1.9, 9.1 Hz, 1H); 4.53 (t, J=6.7 Hz, 2H); 4.23 (dd, J=5.3, 8.6 Hz, 1H); 3.88-4.06 (m, 2H); 3.09 (s, 3H); 2.55-2.63 (m, 2H); 1.09 (t, J=7.1 Hz, 3H).

MS (ESI, m/z): 391.03 [M+H$^+$] for $C_{14}H_{17}N_2O_4BrS$; $t_R$=0.84 min.

A.v. (RS)-ethyl 4-(5-bromo-1H-indazol-1-yl)-2-methyl-2-(methylsulfonyl)butanoate Variant I:
$Cs_2CO_3$ (8.65 g; 26.5 mmol) was added, at rt, to a solution of intermediate A.iv (8.21 g; 21.1 mmol) in DMF (118 mL) and the mixture was stirred for 15 min. $CH_3I$ (5.5 mL; 88.2 mmol) was added and the mixture was stirred overnight. More $Cs_2CO_3$ (3.56 g) and $CH_3I$ (2 mL) were then added and the reaction mixture was stirred overnight. Water (40 mL) and EA (80 mL) were added. The two layers were separated. The aq. layer was extracted with EA (4×50 mL). The combined org. layers were washed with brine (40 mL), dried over $MgSO_4$, filtered and evaporated under reduced pressure. The crude product was purified by CC (Hept-EA) to afford the title compound as a yellow oil (4.93 g, 58% yield).

Variant II:
To a solution of intermediate A.iii (5 g; 14.3 mmol) and ethyl 2-(methylsulfonyl)propanoate (2.8 g; 15.6 mmol) in DMF (30 mL) was added $Cs_2CO_3$ (9.25 g; 28.4 mmol). The reaction was stirred at 80° C. for 3 h. Water (100 mL) was added and the two layers were diluted with EA (100 mL). The aq. layer was extracted with EA (100 mL). The combined org. layers were washed with brine (50 mL), dried over $Na_2SO_4$, filtered and concentrated to dryness. The crude product was purified by CC (Hept-EA) to afford the title compound as a yellowish solid (4.60 g).

$^1$H NMR (d6-DMSO) δ: 8.03 (d, J=0.9 Hz, 1H); 7.99 (dd, J=0.9, 1.8 Hz, 1H); 7.65 (td, J=0.5, 8.9 Hz, 1H); 7.52 (dd, J=1.8, 8.9 Hz, 1H); 4.41-4.64 (m, 2H); 3.77-3.98 (m, 2H); 3.06 (s, 3H); 2.69-2.83 (m, 1H); 2.23-2.32 (m, 1H); 1.05 (t, J=7.1 Hz, 3H).

MS (ESI, m/z): 402.96 [M+H$^+$] for $C_{15}H_{19}N_2O_4BrS$; $t_R$=0.86 min.

A.vi. (RS)-4-(5-bromo-2H-indazol-2-yl)-2-methyl-2-(methylsulfonyl)-N-((tetrahydro-2H-pyran-2-yl)oxy)butanamide To an ice-chilled solution of intermediate A.v (4.21 g; 7.23 mmol) in a THF-MeOH-$H_2O$ mixture (2-2-1; 105 mL) was added LiOH.$H_2O$ (1.73 g; 23 mmol). The reaction mixture was stirred at rt overnight. Solvents were evaporated in vacuo and the residue was dried to a constant weight. The resulting solid was taken up in DMF (70 mL) and HOBT.$H_2O$ (4.24 g, 31.4 mmol), TEA (4.6 mL; 33 mmol), $NH_2$—OTHP (3.80 g, 31.8 mmol) and EDC.HCl (6.24 g, 32.2 mmol) were successively added. The suspension was then stirred at 60° C. for 2 h. More $NH_2$—OTHP (1.27 g; 10.6 mmol) was added and the reaction mixture was heated at 60° C. overnight. The reaction mixture was concentrated to dryness. Water (50 mL) and EA (70 mL) were added. The org. layer was washed with water (15 mL), sat. $NaHCO_3$ (15 mL) and brine (20 mL). The org. layer was dried over $Na_2SO_4$, filtered and concentrated to dryness. The residue was purified by CC (DCM-MeOH) to afford the title compound as a yellowish oil (3.48 g; 71% yield).

MS (ESI, m/z): 474.1[M+H+] for $C_{18}H_{24}N_3O_5BrS$; $t_R$=0.83 min.

Preparation B

(RS)-ethyl 4-(5-iodo-1H-indazol-1-yl)-2-methyl-2-(methylsulfonyl)butanoate

To a solution of intermediate A.v (0.5 g; 1.24 mmol) in 1,4-dioxane (2 mL) was added trans-N,N'-dimethylcyclohexa-1,2-diamine (0.02 mL; 0.124 mmol), NaI (0.376 g; 2.48 mmol) and then CuI (0.013 g; 0.069 mmol). The reaction mixture was then heated at 180° C. in the microwave for 3×20 min. Further trans-N,N-dimethylcyclohexa-1,2-diamine (0.02 mL; 0.124 mmol), NaI (0.376 g; 2.48 mmol) and CuI (0.013 g, 0.069 mmol) were added. The reaction mixture was then heated at 180° C. in the microwave for 20 min. The mixture was diluted in water (15 mL) and EA (20 mL). The aq. layer was extracted twice with EA (2×15 mL). The combined org. layers were washed with brine, dried over MgSO$_4$, filtered and concentrated to dryness. The crude product was purified by CC using a Hept-EA gradient to afford the title product as a white solid (0.366 g; 66% yield).

$^1$H NMR (d6-DMSO) δ: 8.17 (s, 1H); 8.00 (s, 1H); 7.65 (d, J=8.5 Hz, 1H); 8.01 (d, J=9.1 Hz, 1H); 4.36-4.67 (m, 2H); 3.78-4.00 (m, 2H); 3.07 (s, 3H); 2.68-2.85 (m, 1H); 2.21-2.33 (m, 1H); 1.59 (s, 3H); 1.06 (t, J=7.03 Hz, 3H).

MS (ESI, m/z): 492.04 [M+H$^+$] for C$_{15}$H$_{19}$N$_2$O$_4$IS; $t_R$=0.81 min.

Preparation C 2-(2-fluoro-4-(methylthio)phenyl)-4,4,5,5-tetramethyl-1,3,2-dioxaborolane A mixture of bis(pinacolato)diboron (1.15 g; 4.5 mmol), Pd(dppf)Cl$_2$ (0.248 g; 0.3 mmol) and KOAc (1.27 g; 13 mmol) was flushed with nitrogen for 15 min and treated with a solution of 4-bromo-3-fluorothioanisole (1 g; 4.3 mmol; commercial) in dioxane (17 mL). The reaction mixture was heated to reflux for 3 h. After cooling, the reaction mixture was filtered and the filtrate was concentrated to dryness. The residue was purified by CC (Hept-EA) to afford the title compound as a yellow oil (0.84 g; 73% yield).

$^1$H NMR (CDCl$_3$) δ: 7.61 (dd, J=6.5, 7.9 Hz, 1H); 6.98 (dd, J=1.7, 7.9 Hz, 1H); 6.87 (dd, J=1.7, 10.2 Hz, 1H); 2.47 (s, 3H); 1.34 (s, 12H).

MS (ESI, m/z): 269.2 [M+H$^+$] for C$_{13}$H$_{18}$O$_2$BFS; $t_R$=0.96 min.

Preparation D rac-4-(5-bromo-1H-indol-1-yl)-2-methyl-2-(methylsulfonyl)-N-((tetrahydro-2H-pyran-2-yl)oxy)butanamide Starting from 5-bromo-1H-indole (5 g; 25.5 mmol), and proceeding in analogy to Preparation A, steps A.i to A.iii and steps A.v to A.vi (1$^{st}$ alkylation: 98% yield; mesylate formation: 100% yield; iodide formation 66% yield; 2$^{nd}$ alkylation: 56% yield; saponification and coupling with THPO-NH$_2$: 90% yield), the title product was obtained as a white foam (1.66 g).

MS (ESI, m/z): 473.11 [M+H$^+$] for C$_{19}$H$_{25}$N$_2$O$_5$BrS; $t_R$=0.89 min.

Preparation E (2R)-4-(5-ethynyl-6-fluoro-1H-indol-1-yl)-2-methyl-2-(methylsulfonyl)-N-((tetrahydro-2H-pyran-2-yl)oxy)butanamide E.i. (RS)-ethyl 4-(5-bromo-6-fluoro-1H-indol-1-yl)-2-methyl-2-(methylsulfonyl)butanoate Starting from 5-bromo-6-fluoro-1H-indole (5.1 g; 23.8 mmol; commercial), and proceeding in analogy to Preparation A, steps A.i to A.v (1$^{st}$ alkylation: 98% yield; mesylate formation: 100% yield; iodide formation 90% yield; 2$^{nd}$ alkylation: 63% yield; alkylation with MeI: 74% yield), the title product was obtained as a yellowish solid (2.44 g).

$^1$H NMR (d6-DMSO) δ: 7.86 (d, J=7.0 Hz, 1H); 7.55 (d, J=10.3 Hz, 1H); 7.44 (d, J=3.2 Hz, 1H); 6.45 (d, J=2.6 Hz, 1H); 4.40-4.29 (m, 1H); 4.24-4.12 (m, 1H); 4.09-3.90 (m, 2H); 3.10 (s, 3H); 2.74-2.58 (m, 1H); 2.28-2.18 (m, 1H); 1.61 (s, 3H); 1.13 (t, J=7.0 Hz, 3H).

MS (ESI, m/z): 421.97 [M+H+] for C$_{16}$H$_{19}$NO$_4$BrFS; $t_R$=0.93 min.

E.ii. Ethyl (R)-4-(5-bromo-6-fluoro-1H-indol-1-yl)-2-methyl-2-(methylsulfonyl)butanoate The racemic intermediate E.i (2.4 g) was separated by semi preparative chiral HPLC Method A (Hept-EtOH 7-3; flow rate: 16 mL/min, UV detection at 223 nm), the respective retention times (flow rate: 0.8 mL/min) were 9.4 and 11.3 min. The title enantiomer, which was the second eluting enantiomer, was obtained as a brown oil (1.1 g).

$^1$H NMR (d6-DMSO) δ: 7.86 (d, J=7.0 Hz, 1H); 7.55 (d, J=10.3 Hz, 1H); 7.44 (d, J=3.2 Hz, 1H); 6.45 (d, J=2.6 Hz, 1H); 4.40-4.29 (m, 1H); 4.24-4.12 (m, 1H); 4.09-3.90 (m, 2H); 3.10 (s, 3H); 2.74-2.58 (m, 1H); 2.28-2.18 (m, 1H); 1.61 (s, 3H); 1.13 (t, J=7.0 Hz, 3H).

MS (ESI, m/z): 421.97 [M+H+] for C$_{16}$H$_{19}$NO$_4$BrFS; $t_R$=0.93 min.

E.iii. Rac-(2R)-4-(5-bromo-6-fluoro-1H-indol-1-yl)-2-methyl-2-(methylsulfonyl)-N-((tetrahydro-2H-pyran-2-yl)oxy)butanamide Starting from intermediate E.ii (1.1 g, 2.59 mmol) and proceeding in analogy to Preparation A, step A.v, the title product was obtained as a yellowish foam (1.19 g; 90% yield).

$^1$H NMR (d6-DMSO) a (mixture of diastereomers): 7.86 (d, J=7.0 Hz, 1H); 7.55 (m, 1H); 7.45 (d, J=3.2 Hz, 1H); 6.47 (d, J=3.2 Hz, 1H); 5.04 (m, 0.5H); 5.00 (m, 0.5H); 4.37-4.23 (m, 1H); 4.22-3.95 (m, 2H); 3.60-3.46 (m, 1H); 3.03 (s, 1.5H); 3.02 (s, 1.5H); 2.69-2.56 (m, 1H); 2.22-2.08 (m, 1H); 1.71 (m, 3H); 1.57 (s, 3H); 1.56 (s, 3H).

MS (ESI, m/z): 492.92 [M+H$^+$] for C$_{19}$H$_{24}$N$_2$O$_5$BrFS; $t_R$=0.91 min.

E.iv. (2R)-4-(5-ethynyl-6-fluoro-1H-indol-1-yl)-2-methyl-2-(methylsulfonyl)-N-((tetrahydro-2H-pyran-2-yl)oxy)butanamide Intermediate E.iii (0.475 g, 0.967 mmol), bis(tri-tert-butylphosphine) palladium (0.0421 g, 0.0824 mmol), CsF (0.293 g, 1.93 mmol), dioxane (5 mL) and ethynyltri-n-butyltin (0.42 mL, 1.45 mmol) were introduced into a sealed vial. The reaction mixture was stirred at 80° C. for 2 h. The mixture was cooled to rt and concentrated to dryness. The residue was purified by CC (Hept-EA) to afford the title compound as an orange foam (0.093 g, 22% yield).

$^1$H NMR (d6-DMSO) δ (mixture of diastereomers): 11.42 (m, 1H); 7.73 (d, J=6.7 Hz, 1H); 7.45 (d, J=3.2 Hz, 1H); 7.42 (d, J=3.5 Hz, 1H); 6.49 (d, J=2.9 Hz, 1H); 5.03 (m, 1H); 4.36-4.24 (m, 1H); 4.21 (s, 1H); 4.13-3.98 (m, 2H); 3.59-3.47 (m, 1H); 3.03 (s, 1.5H); 3.02 (s, 1.5H); 2.75-2.56 (m, 1H); 2.24-2.07 (m, 1H); 1.71 (m, 3H); 1.57 (m, 6H).

MS (ESI, m/z): 436.99 [M+H$^+$] for C$_{21}$H$_{25}$N$_2$O$_5$FS; t$_R$=0.87 min.

Preparation F

((1S*,2S*)-2-(bromoethynyl)cyclopropyl)methyl acetate

F.i.a. ((1S*,2S*)-2-(2,2-dibromovinyl)cyclopropyl)methyl acetate AND

F.i.b. rac-[(1S*,2S*)-2-(2,2-dibromo-vinyl)-cyclopropyl]-methanol

To a solution of CBr$_4$ (30.0 g, 88.9 mmol) in DCM (60 mL) cooled at −20° C., was added dropwise over 45 min a solution of PPh$_3$ (45.8 g, 175 mmol) in DCM (100 mL). The mixture was kept stirred at this temperature for 30 min and then cooled to −78° C. A solution of ((1S*,2S*)-2-formyl-cyclopropyl)methyl acetate (6.18 g, 43.5 mmol, prepared as described in WO 2012/154204) in DCM (80 mL) was added dropwise over 45 min, keeping the internal temperature below −70° C. The mixture was stirred at this temperature for 30 min and allowed to warm to rt over 1 h. The solvent was removed in vacuo and the residue was purified by CC (EA-Hept) to afford the title acetate as a clear oil (4.84 g, 37% yield), and then the title alcohol as a clear oil (2.2 g, 20% yield).

For intermediate F.i.a:
$^1$H NMR (CDCl$_3$) δ: 5.84 (d, J=9.0 Hz, 1H); 3.97 (m, 2H); 2.07 (s, 3H); 1.61 (m, 1H); 1.33 (m, 1H); 0.78-0.92 (m, 2H).
MS (ESI, m/z): 295.0 [M+H$^+$] for C$_8$H$_{10}$O$_2$Br$_2$; t$_R$=0.87 min.

For intermediate F.i.b:
$^1$H NMR (CDCl$_3$) δ: 5.86 (d, J=9.0 Hz, 1H); 3.47-3.61 (m, 2H); 1.61-1.53 (m, 1H); 1.43 (m, 1H); 1.22-1.34 (m, 1H); 0.74-0.89 (m, 2H).

F.ii. ((1S*,2S*)-2-(bromoethynyl)cyclopropyl)methyl acetate

To a solution of intermediate F.i.a (0.5 g; 1.68 mmol) in THF (9.5 mL) was added TBAF trihydrate (2.98 g; 9.35 mmol). The reaction mixture was heated at 60° C. for 4 h. The reaction mixture was cooled to rt and diluted with diethyl ether (50 mL). The org. phase was washed with water (20 mL) and brine (20 mL), dried over MgSO$_4$ and concentrated to dryness. The residue was purified by CC (EA-Hept) to afford the title compound as a yellow oil (0.24 g, 68% yield).
$^1$H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

Preparation G rac-tert-butyl-((1R*,2R*)-2-iodoethynyl-cyclopropylmethoxy)-dimethyl-silane

G.i. Rac-tert-butyl-[(1S*,2S*)-2-(2,2-dibromo-vinyl)-cyclopropylmethoxy]-dimethyl-silane To a mixture of intermediate F.i.b (1.52 g, 5.96 mmol) in THF (14 mL) were added imidazole (0.823 g, 12.1 mmol) and TBDMS-Cl (1.4 g, 9.3 mmol). The mixture was stirred at rt for 1 h. Water (50 mL) and EA (40 mL) were added and the two layers were decanted. The org. layer was extracted with EA (2×30 mL), washed with aq. sat. NaHCO$_3$ (50 mL), brine (50 mL), dried over MgSO$_4$, filtered and concentrated to dryness to afford the crude product. The crude was purified by CC (Hept-EA gradient) to afford the title compound as a colourless oil (1.56 g, 71% yield).
$^1$H NMR (CDCl$_3$) δ: 5.83 (d, J=9.2 Hz, 1H); 3.58 (d, J=5.5 Hz, 3H); 1.55 (m, 1H); 1.19 (m, 1H); 0.87 (s, 9H); 0.87 (overlapped m, 1H); 0.69 (m, 1H); 0.04 (s, 6H).

G.ii. Rac-tert-butyl-((1R*,2R*)-2-iodoethynyl-cyclopropylmethoxy)-dimethyl-silane To a solution of intermediate G.i (1.56 g, 4.22 mmol) in THF (20 mL) cooled at −74° C. was added, dropwise over 25 min, BuLi (1.97M in hexanes; 4.29 mL; 8.45 mmol), keeping the internal temperature below −70° C. After stirring for 1 h, the solution was warmed to 0° C. and iodine (1.76 g, 6.97 mmol) in solution in THF (14.2 mL) was added dropwise over 47 min. The reaction mixture was stirred at rt for 18 h. The reaction mixture was quenched with a sat. Na$_2$S$_2$O$_3$ solution (50 mL). The two phases were separated. The aq. layer was extracted with DCM (2×150 mL). The combined org. layers were dried over MgSO$_4$ and concentrated to dryness to give the desired compound as a yellow oil (1.61 g, quant.).
$^1$H NMR (CDCl$_3$) δ: 3.58 (d, J=4.7 Hz, 2H); 1.24-1.44 (m, 2H); 0.86 (s, 9H); 0.86 (overlapped, 1H); 0.78 (overlapped, 1H); 0.04 (s, 6H).

Preparation H rac-(2RS)-4-(4-fluoro-5-iodo-1H-indol-1-yl)-2-methyl-2-(methylsulfonyl)-N-((tetrahydro-2H-pyran-2-yl)oxy)butanamide Starting from 4-fluoro-5-iodo-1H-indole (6.51 g, 24.9 mmol) and proceeding in analogy to Preparation A, steps A.i to A.vi (1$^{st}$ alkylation: 44% yield; mesylate formation: 85% yield; iodide formation 64% yield; 2$^{nd}$ alkylation: 82% yield; alkylation with MeI: 89% yield; saponification and coupling with THPO-NH$_2$: 93% yield), the title product was obtained as a yellowish oil (2.08 g).
MS (ESI, m/z): 538.89 [M+H$^+$] for C$_{19}$H$_{24}$N$_2$O$_5$FIS; t$_R$=0.91 min.

Preparation I rac-(2R)-4-(5-iodo-1H-indazol-1-yl)-2-methyl-2-(methylsulfonyl)-N-((tetrahydro-2H-pyran-2-yl)oxy)butanamide

I.i. Ethyl (R)-4-(5-bromo-1H-indazol-1-yl)-2-methyl-2-(methylsulfonyl)butanoate To an ice-chilled suspension of NaH (60% in mineral oil, 1.22 g, 30.4 mmol) in DMF (16 mL) was slowly added a solution of 5-bromo-1H-indazole (5.45 g; 27.7 mmol) in DMF (19 mL), keeping the internal temperature below 6° C. The reaction mixture was stirred for 1 h at 0° C.; then (R)-ethyl 4-bromo-2-methyl-2-(methylsulfonyl)butanoate (9.93 g; 34.6 mmol; prepared as described in WO 2012/137099) in solution in DMF (9 mL) was added, keeping the internal temperature below 3° C. The mixture was warmed to rt and stirred for 3 h. The reaction mixture was diluted with aq. NaHSO$_4$ (15%, 15 mL), water (250 mL) and EA (100 mL). The two phases were separated and the aq. layer was extracted with EA (2×100 mL). The combined org. layers were dried over MgSO$_4$ and filtered and concentrated to dryness. The residue was purified by CC (Hept-EA gradient) to afford the title compound (7.33 g, 66% yield) as a yellowish gum.

$^1$H NMR (d6-DMSO) δ: 8.03 (d, J=0.5 Hz, 1H); 7.99 (m, 1H); 7.65 (m, 1H); 7.52 (dd, J=1.8, 8.9 Hz, 1H); 4.54-4.65 (m, 1H); 4.52-4.40 (m, 1H); 3.77-4.04 (m, 2H); 3.06 (s, 3H); 2.69-2.82 (m, 1H); 2.03-2.22 (m, 1H); 1.59 (s, 3H); 1.05 (t, J=7.1 Hz, 3H).

MS (ESI, m/z): 405.00 [M+H+] for C$_{15}$H$_{19}$N$_2$O$_4$BrS; $t_R$=0.86 min.

I.ii. Ethyl (R)-4-(5-iodo-1H-indazol-1-yl)-2-methyl-2-(methylsulfonyl)butanoate

Starting from intermediate I.i (7.18 g; 17.8 mmol) and proceeding in analogy to Preparation B, the title iodide was obtained, after purification by CC (Hept-EA), as a yellowish oil (6.02 g, 75% yield).

$^1$H NMR (d6-DMSO) δ: 8.16 (d, J=0.9 Hz, 1H); 8.00 (s, 1H); 7.64 (dd, J=1.5, 8.8 Hz, 1H); 7.52 (dd, J=8.9 Hz, 1H); 4.52-4.63 (m, 1H); 4.39-4.51 (m, 1H); 3.77-4.04 (m, 2H); 3.06 (s, 3H); 2.69-2.81 (m, 1H); 2.22-2.32 (m, 1H); 1.58 (s, 3H); 1.05 (t, J=7.1 Hz, 3H).

MS (ESI, m/z): 450.8 [M+H+] for C$_{15}$H$_{19}$N$_2$O$_4$IS; $t_R$=0.88 min.

I.iii. Rac-(2R)-4-(5-iodo-1H-indazol-1-yl)-2-methyl-2-(methylsulfonyl)-N-((tetrahydro-2H-pyran-2-yl)oxy)butanamide Starting from intermediate I.ii (6.02 g; 13.4 mmol), and proceeding in analogy to Preparation A, step A.vi (saponification and coupling with THPO-NH$_2$: 90% yield), the title compound was obtained as a white foam (6.69 g).

MS (ESI, m/z): 450.8 [M+H+] for C$_{18}$H$_{24}$N$_3$O$_5$IS; $t_R$=0.88 min.

Preparation J rac-(2R)-4-(5-ethynyl-1H-indazol-1-yl)-2-methyl-2-(methylsulfonyl)-N-((tetrahydro-2H-pyran-2-yl)oxy)butanamide J.i. (2R)-2-methyl-2-(methylsulfonyl)-N-((tetrahydro-2H-pyran-2-yl)oxy)-4-(5-((trimethylsilyl)ethynyl)-1H-indazol-1-yl)butanamide CuI (0.443 g, 2.33 mmol) and PdCl$_2$(PPh$_3$)$_2$ (0.829 g, 1.18 mmol) were introduced in a two-necked round flask. A solution of the compound of Preparation I (6.03 g, 11.6 mmol) in THF (86 mL), trimethylsilylacetylene (1.81 mL, 12.7 mmol) and TEA (4.04 mL, 28.9 mmol) were added. The reaction proceeded at rt for 2 h. After concentration in vacuo, the residue was purified by CC (Hept-EA gradient) to afford the title compound as a brown foam (4.53 g, 80% yield).

$^1$H NMR (d6-DMSO) δ: 11.4 (s, 0.5H); 11.3 (s, 0.5H); 8.08 (s, 1H); 7.91 (s, 1H); 7.62 (d, J=8.6 Hz, 1H); 7.43 (d, J=8.7 Hz, 1H); 4.92-4.98 (m, 1H); 4.40-4.56 (m, 1H); 4.24-4.39 (m, 1H); 3.02 (s, 1.5H); 3.00 (s, 1.5H); 2.63-2.80 (m, 1H); 2.14-2.31 (m, 1H); 1.62-1.73 (m, 4H); 1.47-1.57 (m, 7H); 0.21 (s, 9H).

MS (ESI, m/z): 492.0 [M+H+] for C$_{23}$H$_{33}$N$_3$O$_5$SSi; $t_R$=0.95 min.

J.ii. Rac-(2R)-4-(5-ethynyl-1H-indazol-1-yl)-2-methyl-2-(methylsulfonyl)-N-((tetrahydro-2H-pyran-2-yl)oxy)butanamide A solution of intermediate J.i (4.53 g, 9.21 mmol) in MeOH (34 mL) was treated by K$_2$CO$_3$ (2.29 g, 16.6 mmol). The mixture was stirred at rt for 40 min. The product was diluted in DCM (40 mL). Water was added (20 mL). The two layers were separated. The aq. layer was extracted 3 times with DCM-MeOH (9-1; 6×20 mL). The combined org. layers were washed with brine, dried over MgSO$_4$, filtered and concentrated down. The residue was purified by CC (DCM-MeOH) to afford the title product as a light brown foam (3.52 g: 91% yield).

$^1$H NMR (d6-DMSO) δ: 11.3-11.4 (m, 1H); 8.09 (s, 1H); 7.92 (s, 1H); 7.63 (d, J=8.8 Hz, 1H); 7.45 (d, J=8.8 Hz, 1H); 4.90-4.97 (m, 1H); 4.40-4.56 (m, 1H); 4.26-4.39 (m, 1H); 3.02 (s, 1.5H); 3.00 (s, 1.5 Hz); 2.62-2.80 (m, 1H); 2.13-2.29 (m, 1H); 1.62-1.72 (m, 4H); 1.42-1.57 (m, 8H).

MS (ESI, m/z): 419.9 [M+H+] for C$_{20}$H$_{25}$N$_3$O$_5$S; $t_R$=0.80 min.

Preparation K 3-(iodoethynyl)oxetan-3-ol

To a solution of 3-ethynyloxetan-3-ol (1.097 g; 11.2 mmol; commercial) in MeOH (50 mL) and 1M aq. KOH (28 mL) was added iodine (3.549 g; 14 mmol). The reaction mixture was stirred for 2 h at rt. Water (150 mL) and DCM (500 mL) were added. The aq. layer was extracted with EA (500 mL). The org. layer were washed with brine, dried over MgSO$_4$, filtered and concentrated down to afford the desired compound as a light yellow solid (2.21 g, 88% yield).

$^1$H NMR (d6-DMSO) δ: 4.60 (d, J=6.5 Hz, 2H); 4.45 (d, J=6.5 Hz, 2H).

Preparation L rac-(2R)-4-(5-iodo-1H-indol-1-yl)-2-methyl-2-(methylsulfonyl)-N-((tetrahydro-2H-pyran-2-yl)oxy)butanamide Starting from 5-iodo-1H-indole (0.65 g, 2.67 mmol) and proceeding in analogy to Preparation I, step I.i (67% yield) and Preparation A, step A.vi (42% yield), the title compound was obtained as a colorless oil (0.2 g).

$^1$H NMR (d6-DMSO) δ: 11.4 (m, 1H); 7.93 (m, 2H); 7.40 (m, 2H); 6.42 (d, J=2.9 Hz, 1H); 5.04 (m, 1H); 4.36-4.13 (m, 2H); 4.12-3.98 (m, 1H); 3.58-3.46 (m, 1H); 3.02 (m, 3H); 2.63-2.56 (m, 1H); 2.22-2.04 (m, 1H); 1.72 (m, 3H); 1.56 (m, 6H).

MS (ESI, m/z): 521.0 [M+H$^+$] for C$_{19}$H$_{25}$N$_2$O$_5$IS; $t_R$=0.91 min.

Preparation M rac-(2R)-4-(5-ethynyl-1H-indol-1-yl)-2-methyl-2-(methylsulfonyl)-N-((tetrahydro-2H-pyran-2-yl)oxy)butanamide Starting from the compound of Preparation L (0.964 g, 1.85 mmol), and proceeding in analogy to Preparation J, steps J.i and J.ii (Sonogashira coupling: 100%; TMS cleavage: 43% yield), the title product was obtained, after purification by CC (Hept-EA), as an orange oil (0.33 g).

¹H NMR (d6-DMSO) δ: 11.43 (m, 1H); 7.71 (m, 1H); 7.46 (m, 2H); 7.24 (m, 1H); 6.47 (d, J=2.9 Hz, 1H); 5.03 (m, 1H); 4.38-4.24 (m, 1H); 4.13-4.04 (m, 2H); 3.91 (s, 1H); 3.59-3.47 (m, 1H); 3.02 (m, 3H); 2.72-2.57 (m, 1H); 2.20-2.07 (m, 1H); 1.72 (m, 3H); 1.57 (m, 6H).

MS (ESI, m/z): 419.1 [M+H$^+$] for $C_{21}H_{26}N_2O_5S$; $t_R$=0.85 min.

Preparation N 3-(iodoethynyl)thietan-3-ol

N.i. 3-((trimethylsilyl)ethynyl)thietan-3-ol

To a solution of TMS-acetylene (2.1 mL; 14.8 mmol) in THF (33 mL), cooled at −78° C., was added dropwise BuLi (1.97M; 8.5 mL; 16.7 mmol) over 20 min, keeping the internal temperature below −68° C. The reaction mixture was stirred at the same temperature for 5 min, then allowed to warm to −20° C. and cooled again at −76° C. A solution of 3-thietanone (1.02 g; 11.3 mmol, commercial) in THF (4.2 mL) was then added dropwise over 10 min (internal temperature below −69° C.) and the reaction mixture was stirred for 80 min before warming to rt. The reaction mixture was quenched by addition of brine (30 mL) and extracted twice with EA (2×40 mL). The combined org. layers were dried over MgSO$_4$, filtered and evaporated under reduced pressure to give a brown solid (1.91 g, 91% yield).

¹H NMR (CDCl$_3$) δ: 3.50 (s, 4H); 2.67 (br. s, 1H); 0.19 (s, 9H).

N.ii. 3-ethynylthietan-3-ol

To a solution of intermediate N.i (1.91 g, 10.3 mmol) in THF (114 mL), cooled at 0° C., was added TBAF (1M in THF; 13 mL). The reaction mixture was stirred at the same temperature for 20 min. The solvent was removed in vacuo. The residue was purified by CC (Hept-EA) to afford the title compound as a yellow oil (1.07 g, 91% yield).

¹H NMR (CDCl$_3$) δ: 3.44-3.58 (m, 4H); 2.71 (br. s, 1H); 2.64 (s, 1H).

N.iii. 3-(iodoethynyl)thietan-3-ol

Starting from intermediate N.ii (1.07 g; 9.38 mmol) and proceeding in analogy to Preparation K, the title compound was obtained as a brown solid (1.83 g; 81% yield).

¹H NMR (CDCl$_3$) δ: 3.43-3.57 (m, 4H), 2.71 (br. s, 1H).

Preparation O ethyl (R)-4-(5-ethynyl-6-fluoro-1H-indol-1-yl)-2-methyl-2-(methylsulfonyl)butanoate Starting from intermediate E.i (0.506 g, 1.2 mmol), and proceeding in analogy to Preparation E, step E.iv, the title compound was obtained as a brown gum (0.32 g; 73% yield).

¹H NMR (d6-DMSO) δ: 7.73 (d, J=6.7 Hz, 1H); 7.47-7.40 (m, 2H); 6.47 (d, J=3.2 Hz, 1H); 4.40-4.29 (m, 1H); 4.21 (overlapped, s, 1H); 4.24-4.11 (m, 1H); 4.09-3.92 (m, 2H); 3.11 (s, 3H); 2.74-2.58 (m, 1H); 2.30-2.17 (m, 1H); 1.61 (s, 3H); 1.13 (t, J=7.0 Hz, 3H).

MS (ESI, m/z): 366.0 [M+H$^+$] for $C_{18}H_{20}NO_4FS$; $t_R$=0.90 min.

Preparation P ((1S,2S)-2-(bromoethynyl)cyclopropyl)methyl acetate AND ((1R,2R)-2-(bromoethynyl)cyclopropyl)methyl acetate P.i. ((1S*,2S*)-2-(2,2-dibromovinyl)cyclopropyl)methyl acetate To a solution of CBr$_4$ (30.0 g; 88.9 mmol) in DCM (60 mL) cooled at −20° C., was added dropwise over 45 min a solution of PPh$_3$ (45.8 g, 175 mmol) in DCM (100 mL). The mixture was kept stirred at this temperature for 30 min and then cooled to −78° C. A solution of ((1S*,2S*)-2-formylcyclopropyl)methyl acetate (6.18 g, 43.5 mmol, prepared as described in WO 2012/154204) in DCM (80 mL) was added dropwise over 45 min, keeping the internal temperature below −70° C. The mixture was stirred at this temperature for 30 min and allowed to warm to rt over 1 h. The solvent was removed in vacuo and the residue was purified by CC (EA-Hept) to afford the title acetate as a clear oil (4.84 g, 37% yield).

¹H NMR (CDCl$_3$) δ: 5.84 (d, J=9.0 Hz, 1H); 3.97 (m, 2H); 2.07 (s, 3H); 1.61 (m, 1H); 1.33 (m, 1H); 0.78-0.92 (m, 2H).

MS (ESI, m/z): 295.0 [M+H$^+$] for $C_8H_{10}O_2Br_2$; $t_R$=0.87 min.

P.ii. ((1S,2S)-2-(bromoethynyl)cyclopropyl)methyl acetate AND ((1R,2R)-2-(bromoethynyl)cyclopropyl)methyl acetate To a solution of intermediate P.i (3.94 g; 13.2 mmol) in THF (75 mL) was added TBAF trihydrate (23.2 g; 72.8 mmol). The reaction mixture was heated at 60° C. for 4 h. The reaction mixture was cooled to rt and diluted with diethyl ether (150 mL). The org. phase was washed with water (60 mL) and brine (60 mL), dried over MgSO$_4$ and concentrated to dryness. The residue was purified by CC (EA-Hept) to afford the title compound as a yellow oil (1.76 g, 61% yield). The racemic product was separated by semi-preparative chiral HPLC Method B (Hept-EtOH 9-1; flow rate: 20 mL/min, UV detection at 223 nm), the respective retention times (flow rate: 0.8 mL/min) were 5.9 and 8.7 min. The title enantiomers were obtained as clear oils (0.64 g each).

First-Eluting Enantiomer, (1S,2S)-Configurated:

¹H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

[α]$_D$=+96° (c=1.03; MeOH).

Second-Eluting Enantiomer, (1R,2R)-Configurated:

¹H NMR (CDCl$_3$) δ: 3.97 (dd, J=6.5, 11.7 Hz, 1H); 3.84 (dd, J=7.5, 11.7 Hz, 1H); 2.06 (s, 3H); 1.50 (m, 1H); 1.25 (m, 1H); 0.97 (m, 1H); 0.76 (m, 1H).

[α]$_D$=−94° (c=1.01; MeOH).

The respective absolute configurations of these compounds have been determined though transformation of the second-eluting enantiomer into the corresponding (S) and (R) α-methoxy-α-trifluoromethylphenylacetyl esters and the subsequent analysis of their NMR spectra as described by Tsuda et al. in *Chem. Pharm. Bull.* (2003), 51, 448-451.

Preparation Q ((1R,2R)-2-(4-iodophenyl)cyclopropyl)methanol AND ((1S,2S)-2-(4-iodophenyl)cyclopropyl)methanol Rac-(trans-2-(4-iodophenyl)cyclopropyl)methanol (0.956 g; prepared as described in WO 2005/103032) was separated by semi preparative chiral HPLC Method A (Hept-EtOH 3-1; flow rate: 16 mL/min, UV detection at 210 nm), the respective retention times (flow rate: 0.8 mL/min) were 5.7 and 7.1 min. The title enantiomers were obtained as white powders (0.45 g each).

First-Eluting Enantiomer, (1R,2R)-Configurated:

$^1$H NMR (CDCl$_3$) δ: 7.54 (d, J=8.0 Hz, 2H); 6.86 (d, J=8.0 Hz, 2H); 4.56 (br. s, 1H); 3.43 (m, 1H); 3.32 (m, 1H); 1.73 (m, 1H); 1.23 (m, 1H); 0.75-0.90 (m, 2H). [α]$_D$=−61° (c=1.04; MeOH).

Second-Eluting Enantiomer, (1S,2S)-Configurated:

$^1$H NMR (CDCl$_3$) δ: 7.54 (d, J=8.0 Hz, 2H); 6.86 (d, J=8.0 Hz, 2H); 4.56 (br. s, 1H); 3.43 (m, 1H); 3.32 (m, 1H); 1.73 (m, 1H); 1.23 (m, 1H); 0.75-0.90 (m, 2H). [α]$_D$=+62° (c=1.04; MeOH).

The respective absolute configurations of these compounds have been determined though transformation of the second-eluting enantiomer into the corresponding (S) and (R) α-methoxy-α-trifluoromethylphenylacetyl esters and the subsequent analysis of their NMR spectra as described by Tsuda et al. in *Chem. Pharm. Bull.* (2003), 51, 448-451.

Preparation R 4-iodo-2-methylbut-3-yn-2-amine

Starting from 2-methylbut-3-yn-2-amine (0.5 g; 6 mmol) and proceeding in analogy to Preparation K, the title compound was obtained as a yellow solid (0.98 g; 78% yield).

$^1$H NMR (d6-DMSO) δ: 2.01 (s, 2H); 1.24 (s, 6H).

MS (ESI, m/z): 210.01 [M+H$^+$] for C$_5$H$_8$NI; t$_R$=0.33 min.

Preparation S (1-(4-ethynylphenyl)cyclopropyl)methanol

Starting from (1-(4-bromophenyl)cyclopropyl)methanol (1 g; 4.4 mmol; commercial) and proceeding in analogy to Preparation E, step E.iv, the title compound was obtained as a brownish solid (0.62 g; 82% yield).

$^1$H NMR (d6-DMSO) δ: 7.36-7.39 (m, 2H); 7.27-7.31 (m, 2H); 4.71 (t, J=5.6 Hz, 1H); 4.11 (s, 1H); 3.53 (d, J=5.6 Hz, 2H); 0.84-0.88 (m, 2H); 0.74-0.77 (m, 2H).

Preparation T (2R)-4-(5-ethynyl-4-fluoro-1H-indazol-1-yl)-2-methyl-2-(methylsulfonyl)-N-((tetrahydro-2H-pyran-2-yl)oxy)butanamide T.i. Ethyl (R)-4-(5-bromo-4-fluoro-2H-indazol-2-yl)-2-methyl-2-(methylsulfonyl)butanoate To an ice-chilled suspension of NaH (60% dispersion in mineral oil; 0.736 g; 18.4 mmol) in DMF (11 mL) was slowly added a solution of 5-bromo-4-fluoro-1H-indazole (3 g; 14 mmol) in DMF (11 mL), keeping the internal temperature below 6° C. The reaction mixture was stirred for 1 h at 0° C.; then (R)-ethyl 4-bromo-2-methyl-2-(methylsulfonyl)butanoate (4.63 g, 16.1 mmol) in solution in DMF (5.4 mL) was added, keeping the internal temperature below 3° C. The mixture was warmed to rt and stirred for 3 h. The reaction mixture was diluted with aq. NaHSO$_4$ (15%, 15 mL), water (50 mL) and EA (50 mL). The two phases were separated and the aq. layer was extracted with EA (2×50 mL). The combined org. layers were dried over MgSO$_4$ and filtered and concentrated to dryness. The residue was purified by CC (Hept-EA gradient) to afford the 1-indazole regioisomer as a yellow gum (2.09 g, 36% yield).

$^1$H NMR (d6-DMSO) δ: 8.22 (s, 1H); 7.63 (dd, J=6.4, 8.9 Hz, 1H); 7.49-7.56 (m, 1H); 4.57-4.70 (m, 1H); 4.42-4.56 (m, 1H); 3.80-4.05 (m, 2H); 3.07 (s, 3H); 2.67-2.91 (m, 1H); 2.23-2.35 (m, 1H); 1.60 (s, 3H); 1.07 (t, J=7.1 Hz, 3H).

MS (ESI, m/z): 422.81 [M+H$^+$] for C$_{15}$H$_{18}$N$_2$O$_4$BrFS; t$_R$=0.89 min.

T.ii. (2R)-4-(4-fluoro-5-iodo-1H-indazol-1-yl)-2-methyl-2-(methylsulfonyl)-N-((tetrahydro-2H-pyran-2-yl)oxy)butanamide Starting from intermediate T.i (4.0 g, 9.66 mmol) and proceeding sequentially in analogy to Preparation B and Preparation A, step A.vi, the title compound was obtained as a yellow gum (2.4 g).

$^1$H NMR (d6-DMSO) a (mixture of isomers): 11.46 (br. s, 0.5H); 11.41 (br. s, 0.5H); 8.19-8.21 (m, 1H); 7.70-7.75 (m, 1H); 7.36-7.41 (m, 1H); 4.94-4.97 (m, 0.5H); 4.90-4.92 (m, 0.5H); 4.50-4.58 (m, 1H); 4.31-4.43 (m, 1H); 4-4.07 (m, 1H); 3.48-3.55 (m, 1H); 3.04 (s, 1.5H); 3.02 (s, 1.5H); 2.47-2.54 (overlapped m, 1H); 2.19-2.27 (m, 1H); 1.65-1.71 (m, 3H); 1.54 (s, 1.5H); 1.53 (s, 1.5H); 1.51-1.58 (overlapped m, 3H).

MS (ESI, m/z): 540.83 [M+H$^+$] for C$_{18}$H$_{23}$N$_3$O$_5$FIS; t$_R$=0.86 min.

T.iii. (2R)-4-(5-ethynyl-4-fluoro-1H-indazol-1-yl)-2-methyl-2-(methylsulfonyl)-N-((tetrahydro-2H-pyran-2-yl)oxy)butanamide Starting from intermediate T.ii (2.4 g, 4.44 mmol), and proceeding in analogy to Preparation J, the title compound was obtained as a yellow gum (0.84 g; 58% yield).

$^1$H NMR (d6-DMSO) δ (mixture of stereoisomers): 11.47 (s, 0.5H); 11.41 (s, 0.5H); 8.27-8.29 (m, 1H); 7.48-7.54 (m, 2H); 4.90-4.99 (m, 1H); 4.51-4.59 (m, 1H); 4.42 (s, 1H); 4.31-4.43 (overlapped m, 1H); 3.99-4.17 (m, 1H); 3.49-3.55 (m, 1H); 3.04 (s, 1.5H); 3.02 (s, 1.5H); 2.70-2.81 (m, 1H); 2.20-2.27 (m, 1H); 1.65-1.72 (m, 3H); 1.55 (s, 1.5H); 1.54 (s, 1.5H); 1.50-1.58 (overlapped m, 3H).

MS (ESI, m/z): 438.0 [M+H$^+$] for C$_{20}$H$_{24}$N$_3$O$_5$FS; t$_R$=0.82 min.

Preparation U ((1-(bromoethynyl)cyclopropyl)methoxy)(tert-butyl)diphenylsilane

To a mixture of (dibromomethyl)triphenylphosphonium bromide (8.527 g, 16.6 mmol) and THF (40 mL) was added a solution of tBuOK (1M in THF) (16.6 mL, 16.6 mmol). The resulting dark brown solution was stirred for 3 min at rt, then cooled to 0° C. A solution of 1-(((tert-butyldiphenylsilyl)oxy)methyl)cyclopropanecarbaldehyde (2.2 g; 6.62 mmol; prepared as described in WO 2010/135536) in THF (23 mL) was added dropwise. The reaction was stirred at 0° C. for 40 min. The reaction mixture was cooled to −78° C. and tBuOK (1M in THF, 29.1 mL, 29.1 mmol) was added rapidly and stirred at −78° C. for 30 min. The reaction mixture was quenched with brine (150 mL). The aq. layer was separated and extracted with Et$_2$O (3×150 mL). The combined org. phases were washed with brine, dried over MgSO$_4$, filtered, and concentrated to dryness. The residue was purified by CC (Hept-EA) to afford the title compound as a colourless oil (2.052 g, 75% yield).

¹H NMR (d6-DMSO) δ: 7.60-7.66 (m, 4H); 7.42-7.48 (m, 6H); 3.57 (s, 2H); 1.02 (s, 9H); 0.84-0.88 (m, 2H); 0.72-0.76 (m, 2H).

Preparation V (3-(4-iodophenyl)oxetan-3-yl)methanol

Starting from (3-(4-bromophenyl)oxetan-3-yl)methanol (0.24 g; 0.98 mmol; commercial) and proceeding in analogy to Preparation B, the title iodide was obtained, after purification by CC (Hept-EA), as an off-white solid (0.27 g, 94% yield).
¹H NMR (d6-DMSO) δ: 7.69 (d, J=7.1 Hz, 2H); 6.96 (d, J=7.1 Hz, 2H); 5.10 (t, J=5.6 Hz, 1H); 4.60-4.73 (m, 4H); 3.69 (d, J=5.3 Hz, 2H).

Preparation W (2R)-4-(5-ethynyl-6-fluoro-1H-indazol-1-yl)-2-methyl-2-(methylsulfonyl)-N-((tetrahydro-2H-pyran-2-yl)oxy)butanamide W.i. Ethyl (R)-4-(5-bromo-6-fluoro-2H-indazol-2-yl)-2-methyl-2-(methylsulfonyl)butanoate Starting from 5-bromo-6-fluoro-1H-indazole (1.12 g; 5.21 mmol, prepared as described in WO 2006/044860) and (R)-ethyl 4-bromo-2-methyl-2-(methylsulfonyl)butanoate (1.25 g, 6.22 mmol) and proceeding as described in Preparation T, step T.i. (alkylation), the title compound was obtained, after purification by CC (Hept-EA gradient), as a yellowish oil (1.25 g, 57% yield).
¹H NMR (d6-DMSO) δ: 8.17 (d, J=5.6 Hz, 1H); 8.08 (s, 1H); 7.83 (d, J=9.4 Hz, 1H); 4.55-4.62 (m, 1H); 4.42-4.51 (m, 1H); 3.89-3.95 (m, 1H); 3.78-3.85 (m, 1H); 3.09 (s, 3H); 2.77-2.83 (m, 1H); 2.25-2.32 (m, 1H); 1.61 (s, 3H); 1.12 (t, J=7.1 Hz, 3H).
MS (ESI, m/z): 422.8 [M+H+] for $C_{15}H_{18}N_2O_4BrFS$; $t_R$=0.87 min.

W.ii. (2R)-4-(6-fluoro-5-iodo-1H-indazol-1-yl)-2-methyl-2-(methylsulfonyl)-N-((tetrahydro-2H-pyran-2-yl)oxy)butanamide Starting from intermediate W.i (1.25 g, 2.98 mmol) and proceeding sequentially in analogy to Preparation B and Preparation A, step A.vi, the title compound was obtained as a yellow gum (0.46 g).
¹H NMR (d6-DMSO) δ (mixture of isomers): 11.48 (s, 0.5H); 11.40 (s, 0.5H); 8.28-8.31 (m, 1H); 8.07 (s, 0.5H); 8.06 (s, 0.5H); 7.62-7.67 (m, 1H); 4.95-4.99 (m, 0.5H); 4.91-4.93 (m, 0.5H); 4.43-4.51 (m, 1H); 4.24-4.35 (m, 1H); 4.11-4.19 (m, 0.5H); 4.00-4.09 (m, 0.5H); 3.49-3.57 (m, 1H); 3.04 (s, 1.5H); 3.02 (s, 1.5H); 2.67-2.79 (m, 1H); 2.18-2.26 (m, 1H); 1.65-1.73 (m, 3H); 1.54 (s, 1.5H); 1.52 (s, 1.5H); 1.50-1.59 (overlapped m, 3H).
MS (ESI, m/z): 539.83 [M+H+] for $C_{18}H_{23}N_3O_5FIS$; $t_R$=0.85 min.

W.iii. (2R)-4-(5-ethynyl-6-fluoro-1H-indazol-1-yl)-2-methyl-2-(methylsulfonyl)-N-((tetrahydro-2H-pyran-2-yl)oxy)butanamide Starting from intermediate W.ii (0.46 g, 0.86 mmol), and proceeding in analogy to Preparation J, the title compound was obtained as a white foam (0.22 g; 58% yield).

¹H NMR (d6-DMSO) (mixture of stereoisomers) δ: 11.49 (s, 0.5H); 11.41 (s, 0.5H); 8.12-8.14 (m, 1H); 8.02-8.05 (m, 1H); 7.60-7.65 (m, 1H); 4.93-4.99 (m, 1H); 4.43-4.52 (m, 1H); 4.37 (s, 1H); 4.25-4.39 (overlapped m, 1H); 4.12-4.18 (m, 0.5H); 4.00-4.08 (m, 0.5H); 3.49-3.57 (m, 1H); 3.04 (s, 1.5H); 3.02 (s, 1.5H); 2.67-2.79 (m, 1H); 2.19-2.26 (m, 1H); 1.65-1.73 (m, 3H); 1.50-1.59 (m, 6H).
MS (ESI, m/z): 438.0 [M+H+] for $C_{20}H_{24}N_3O_5FS$; $t_R$=0.81 min.

Preparation X 3-(4-iodophenyl)oxetan-3-ol

A solution of 1,4-diiodobenzene (0.800 g; 2.43 mmol) in THF (8 mL) was treated at −78° C. with BuLi (1.68M in Hex; 2.23 mL; 1.33 mmol). After stirring at this temperature for 30 min, the solution was treated with a suspension of 3-oxetanone (0.24 g; 3.34 mmol) in THF (3 mL). The reaction mixture was allowed to reach rt and was further stirred overnight. The reaction mixture was treated with a 10% aq. NaHSO₄ solution (4 mL) and diluted water and EA. The aq. layer was extracted with EA. The combined org. layers were washed with brine, dried over MgSO₄, filtered and concentrated under reduced pressure. The residue was purified by CC (Hept-EA) to afford the title alcohol as a white solid (0.2 g, 55% yield).
¹H NMR (300 MHz, d₆-DMSO) δ: 7.73 (d, J=8.5 Hz, 2H); 7.39 (d, J=8.5 Hz, 2H); 6.39 (s, 1H); 4.73 (d, J=6.8 Hz, 2H); 4.60 (d, J=6.8 Hz, 2H).

Preparation Y (RS)-4-(5-ethynyl-4-fluoro-1H-indol-1-yl)-2-methyl-2-(methylsulfonyl)-N—(((RS)-tetrahydro-2H-pyran-2-yl)oxy)butanamide Starting from the compound of Preparation H (1.68 g; 3.11 mmol) and proceeding in analogy to Preparation J, steps J.i and J.ii (96% yield for the Sonogashira coupling and 52% yield for the silyl removal), the title compound was obtained, after purification by CC (Hept-EA), as a yellow gum (0.67 g).
MS (ESI, m/z): 437.02 [M+H+] for $C_{21}H_{25}N_2O_5FS$; $t_R$=0.87 min.

Preparation Z 3-(4-ethynylphenyl)oxetan-3-ol

Starting from the compound of Preparation X and proceeding in analogy to Preparation J, steps J.i and J.ii (97% yield for the Sonogashira coupling, 99% yield for the deprotection), the title compound was obtained, after purification by CC (Hept-EA), as a light beige solid (0.605 g).
¹H NMR (300 MHz, d₆-DMSO) δ: 7.62 (d, J=8.5 Hz, 2H); 7.50 (d, J=8.5 Hz, 2H); 6.43 (s, 1H); 4.77 (d, J=6.7 Hz, 2H); 4.65 (d, J=6.7 Hz, 2H); 4.16 (s, 1H).

Preparation AA di-tert-butyl ((1-(4-ethynylphenyl)cyclopropyl)methyl) phosphate

To a solution of the compound of Preparation S (0.051 g; 0.3 mmol) in THF (1.8 mL) at 0° C. were added tetrazole (0.45M in MeCN; 0.12 mL; 1.38 mmol) and di-tert-butyl diisopropylphosphoramidite (0.36 mL; 1.14 mmol; commercial). The reaction was stirred at 0° C. overnight. Tetrazole (0.45M in MeCN; 0.12 mL; 1.38 mmol) and di-tert-butyl diisopropylphosphoramidite (0.36 mL; 1.14 mmol) were added at 0° C. The reaction proceeded 2 days at rt. More tetrazole (0.45M in MeCN; 0.04 mL; 0.46 mmol) and di-tert-butyl diisopropylphosphoramidite (0.12 mL; 0.38 mmol) were added and the reaction mixture was stirred at 40° C. for 3 more days before being cooled to 0° C. $H_2O_2$ (35%; 3.2 mL) was then added slowly over 30 min. The reaction mixture was stirred for 30 min at 0° C. Water (5 mL) was added. The aq. layer was extracted with EA (2×15 mL). The combined org. layers were washed with brine (10 mL), dried over $MgSO_4$ and filtered. The filtrate was concentrated to dryness. The residue was purified by CC (Hept-EA) to afford the title compound as a white solid (0.067 g; 62% yield).

$^1$H NMR (500 MHz, CDCl$_3$) δ: 7.39-7.43 (m, 2H); 7.29-7.32 (m, 2H); 4.02 (d, J=5.5 Hz, 2H); 3.04 (s, 1H); 1.40 (s, 18H); 0.98-1.01 (m, 2H); 0.91-0.94 (m, 2H).

Preparation AB (1-(4-ethynylphenyl)cyclopropyl)methyl dimethylglycinate

To a solution of the compound of Preparation S (0.20 g; 1.18 mmol) in DCM (13 mL) were added N,N-dimethylglycine (0.13 g; 1.18 mmol), EDC (0.31 g; 1.6 mmol) and DMAP (0.19 g; 1.53 mmol). The reaction was stirred at rt for 27 h. An aq. solution of NaHCO$_3$ (5%; 5 mL) was added to the reaction mixture and the aq. layer was extracted with DCM (2×20 mL). The combined org. layers were dried over MgSO$_4$, filtered and concentrated to dryness. The residue was purified by CC (DCM-MeOH) to afford the title compound as a yellow oil (0.23 g, 76% yield).

$^1$H NMR (500 MHz, d$_6$-DMSO) δ: 7.37-7.41 (m, 2H); 7.26-7.30 (m, 2H); 4.21 (s, 2H); 4.13 (s, 1H); 3.10 (s, 2H); 2.17 (s, 6H); 0.97-1.01 (m, 2H); 0.90-0.94 (m, 2H).

MS (ESI, m/z): 258.07 [M+H$^+$] for $C_{16}H_{19}NO_2$; $t_R$=0.63 min.

Preparation AC (R)-5-bromopent-4-yne-1,2-diol

To a solution of (R)-but-3-yne-1,2-diol (0.106 g; 1.06 mmol; prepared as described in WO 2013/170030) in acetone (4 mL) was added NBS (0.23 g; 1.28 mmol) followed by AgNO$_3$ (0.015 g; 0.085 mmol). The reaction mixture was stirred at rt for 2 h. Hept (5 mL) and water (6 mL) were added. The phases were separated and the aq. layer was extracted with EA (3×10 mL). The combined org. layers were dried over MgSO$_4$, filtered and evaporated under reduced pressure. The residue was purified by CC (Hept-EA) to afford the title compound as an off-white solid (0.119 g, 63% yield).

$^1$H NMR (500 MHz, CDCl$_3$) δ: 3.86-3.92 (m, 1H); 3.72-3.77 (m, 1H); 3.56-3.62 (m, 1H); 2.46-2.48 (m, 2H); 2.34-2.39 (m, 1H); 1.90-1.97 (m, 1H).

Preparation AD (3aR,5S,6aS)-5-(bromoethynyl)-2,2-dimethyltetrahydro-4H-cyclopenta[d][1,3]dioxole A solution of (3aR,5S,6aS)-5-(2,2-dibromovinyl)-2,2-dimethyltetrahydro-4H-cyclopenta[d][1,3]dioxole (2.06 g; 6.32 mmol; prepared as described in WO 2013/170030) in dry THF (15 mL), cooled at −78° C., was treated dropwise with a solution of tBuOK (1M in THF, 28 mL), keeping IT below −67° C. The reaction mixture was stirred for 30 min at −78° C., then was diluted with brine (20 mL) and was allowed to reach rt. Et$_2$O (25 mL) was added. The aq. layer was separated and extracted with Et$_2$O (15 mL). The combined org. layers were washed with brine (10 mL), dried over MgSO$_4$, filtered and concentrated to afford the title compound as a yellow oil (1.37 g; 88% yield).

$^1$H NMR (500 MHz, CDCl$_3$) δ: 4.60-4.63 (m, 2H); 2.85-2.93 (m, 1H); 2.12-2.17 (m, 2H); 1.51-1.60 (overlapped m, 2H); 1.41 (s, 3H); 1.26 (s, 3H).

Preparation AE (1-(4-iodophenyl)cyclopropyl)methanol

Starting from (1-(4-bromophenyl)cyclopropyl)methanol (0.45 g; 1.98 mmol; commercial) and proceeding in analogy to Preparation B, the title compound was obtained as a white solid (0.51 g; 95% yield).

$^1$H NMR (500 MHz, d$_6$-DMSO) δ: 7.59-7.62 (m, 2H); 7.08-7.12 (m, 2H); 4.69 (t, J=5.7 Hz, 1H); 3.49 (d, J=5.7 Hz, 2H); 0.81-0.84 (m, 2H); 0.69-0.72 (m, 2H).

Preparation AF ((3-(bromoethynyl)bicyclo[1.1.1]pentan-1-yl)methoxy)(tert-butyl)diphenylsilane AF.i. Bicyclo[1.1.1]pentane-1, 3-diyldimethanol To a solution of dimethyl bicyclo[1.1.1]pentane-1,3-dicarboxylate (1.74 g; 9.45 mmol; commercial) in THF (12 mL), cooled at 0° C. was added dropwise LiAlH$_4$ (2.4M in THF; 5.29 mL; 12.7 mmol) over 45 min, keeping IT below 15° C. The suspension was stirred at rt for 3 h. The crude mixture was cooled to 0° C. and carefully quenched by water (0.48 mL), 15% aq. NaOH (0.48 mL) and water (1.44 mL). The mixture was stirred at rt for 35 min then THF (17 mL) and MgSO$_4$ were added. The mixture was stirred at rt for 10 min. The mixture was filtered and concentrated to dryness. The residue was purified by CC (Hept-EA) to afford the title compound as a colourless oil (1.2 g; 99% yield).

$^1$H NMR (500 MHz, d$_6$-DMSO) δ: 4.40 (t, J=5.5 Hz, 2H); 3.35 (d, J=5.6 Hz, 4H); 1.46 (s, 6H).

AF.ii. (3-(((tert-butyldiphenylsilyl)oxy)methyl)bicyclo[0.1.1]pentan-1-yl)methanol To a suspension of NaH (60% in mineral oil; 0.23 g; 5.67 mmol) in THF (4.5 mL) was added slowly at rt a solution of intermediate AF.i (0.66 g; 5.16 mmol) in THF (3.3 mL), keeping IT below 27° C. After 1 h stirring, a solution of TBDPS-Cl (1.36 mL; 5.16 mmol) in THF (2.8 mL) was added dropwise over 15 min. The solution was stirred for 4 h, then diluted in Et$_2$O (20 mL). The org. phase was washed with brine (2×20 mL), dried over Na$_2$SO$_4$, filtered and concentrated to dryness. The residue was purified by CC (Hept-EA) to afford the title compound as a colourless oil (0.49 g; 26% yield).

$^1$H NMR (500 MHz, d$_6$-DMSO) δ: 7.56-7.64 (m, 4H); 7.39-7.50 (m, 6H); 4.43 (t, J=5.6 Hz, 1H); 3.64 (s, 2H); 3.36 (d, J=5.5 Hz, 2H); 1.49 (s, 6H); 1.01 (s, 9H).

AF.iii. 3-(((tert-butyldiphenylsilyl)oxy)methyl)bicyclo[0.1.1]pentane-1-carbaldehyde To a solution of intermediate AF.ii (1.09 g; 2.98 mmol) in DCM (6.9 mL), cooled to −10° C., was added DIPEA (1.59 mL; 9.31 mmol) over 15 min. A solution of Pyr.SO$_3$ complex (45%; 1.44 g; 4.07 mmol) in DMSO (4.03 mL) was then added dropwise over 10 min. The reaction mixture was stirred for 1.5 h at 0° C. and 1 h at rt. The reaction mixture was partitioned between water (35 mL) and DCM (20 mL). The aq. layer was extracted with DCM (15 mL). The combined org. layers were dried over Na$_2$SO$_4$, filtered and concentrated to dryness. The residue was co-evaporated with toluene (2×10 mL) and then purified by CC (Hept-EA) to afford the title compound as a colourless oil (0.94 g; 87% yield).

$^1$H NMR (500 MHz, d$_6$-DMSO) δ: 9.53 (s, 1H); 7.57-7.62 (m, 4H); 7.41-7.49 (m, 6H); 3.68 (s, 2H); 1.86 (s, 6H); 1.01 (s, 9H).

AF.iv. ((3-(bromoethynyl)bicyclo[. 0.1.1]pentan-1-yl)methoxy) (tert-butyl)diphenylsilane Starting from intermediate AF.iii (0.45 g; 0.86 mmol) and proceeding successively in analogy to Preparation F, step F.i (89% yield) and Preparation AD (97% yield), the title compound was obtained as a yellow oil (0.37 g).

$^1$H NMR (500 MHz, d$_6$-DMSO) δ: 7.55-7.60 (m, 4H); 7.41-7.49 (m, 6H); 3.60 (s, 2H); 1.91 (s, 6H); 1.00 (s, 9H).

Preparation AG tert-butyl ((1-(bromoethynyl)cyclopropyl)methyl)carbamate

Starting from tert-butyl ((1-formylcyclopropyl)methyl) carbamate (0.5 g; 2.51 mmol; commercial) and proceeding in analogy to Preparation U, the title compound was obtained, after purification by CC (Hept-EA), as a yellow oil (0.61 g; 88% yield).

$^1$H NMR (500 MHz, d$_6$-DMSO) δ: 6.73 (s, 1H); 2.96-3.03 (m, 2H); 1.39 (s, 9H); 0.64-0.79 (m, 4H).

REFERENCE EXAMPLES

Reference Example 1

(RS)-4-(5-(but-2-yn-1-yloxy)-1H-indol-1-yl)-N-hydroxy-2-methyl-2-(methylsulfonyl)butanamide

RE1.i. 5-(but-2-yn-1-yloxy)-1H-indole

A mixture of 5-hydroxyindole (2.0 g; 14.8 mmol; commercial), K$_2$CO$_3$ (2.5 g; 18.2 mmol), acetone (12 mL) and 1-bromo-but-2-yne (1.3 mL, 14.8 mmol) was heated to reflux overnight. The reaction mixture was filtered and the solids were washed with acetone. The filtrate was evaporated to dryness. The crude residue was purified by CC (DCM-MeOH) to afford the title compound (1.9 g).

$^1$H NMR (d6-DMSO) δ: 10.8 (br. s, 1H); 7.20-7.28 (m, 2H); 7.06 (d, J=2.3 Hz, 1H); 6.72 (dd, J=2.3, 8.7 Hz, 1H); 6.31 (s, 1H); 4.66 (s, 2H); 1.80 (s, 3H).

MS (ESI, m/z): 186.2 [M+H$^+$] for C$_{12}$H$_{11}$NO; t$_R$=0.81 min.

RE1.ii. 2-(5-(but-2-yn-1-yloxy)-1H-indol-1-yl)ethanol

A solution of intermediate RE1.i (0.8 g; 4.3 mmol) in DMF (29 mL), cooled to 0° C., was treated with NaH (60% in oil dispersion, 0.189 g, 4.72 mmol). The reaction mixture was stirred at rt for 30 min. Ethylene carbonate (1.53 g, 17.4 mmol) was added and the reaction mixture was heated at 80° C. for 1 h. After cooling to rt, water (45 mL) was added and the mixture was extracted with EA (4×25 mL). The combined org. layers were washed with brine (30 mL), dried over MgSO$_4$, filtered and concentrated to dryness. The crude residue was purified by CC (EA-Hept) to afford the title compound (still contaminated with some remaining ethylene carbonate) as a yellow oil (1.13 g).

$^1$H NMR (d6-DMSO) δ: 7.34 (d, J=8.9 Hz, 1H); 7.28 (d, J=3.0 Hz, 1H); 7.06 (d, J=2.4 Hz, 1H); 6.76 (dd, J=2.4, 8.9 Hz, 1H); 6.30 (d, J=0.4, 3.0 Hz, 1H); 4.82 (t, J=5.3 Hz, 1H); 4.67 (q, J=2.3 Hz, 2H); 4.14 (t, J=5.7 Hz, 2H); 3.66 (q, J=5.5 Hz, 2H); 1.80 (t, J=2.3 Hz, 3H).

MS (ESI, m/z): 230.2 [M+H$^+$] for C$_{14}$H$_{15}$NO$_2$; t$_R$=0.76 min.

RE1.iii. 2-(5-(but-2-yn-1-yloxy)-1H-indol-1-yl)ethyl methanesulfonate

To an ice-chilled solution of intermediate RE1.ii (1.13 g; 4.94 mmol) in DCM (27 mL) were added Et$_3$N (1.5 mL, 10.8 mmol) and MsCl (0.48 mL, 6.2 mmol). The reaction was stirred at 0° C. for 1 h, then for 30 min at rt. The reaction mixture was poured on to sat. NaHCO$_3$ (35 mL). The two layers were separated and the org. layer was dried over MgSO$_4$, filtered and concentrated to dryness. The residue was purified by CC (EA-Hept) to afford the title compound as a yellow oil (1.01 g).

MS (ESI, m/z): 308.1 [M+H+] for C$_{15}$H$_{17}$NO$_4$S; t$_R$=0.85 min.

RE1.iv. 5-(but-2-yn-1-yloxy)-1-(2-iodoethyl)-1H-indole

To a solution of intermediate RE1.iii (1.01 g; 3.31 mmol) in 2-butanone (15 mL) was added NaI (0.9 g, 6.06 mmol). The mixture was heated to 90° C. for 1.5 h. The reaction mixture was partitioned between EA (35 mL) and water (25 mL). The aq. layer was extracted with EA (2×25 mL). The combined org. layers were washed with sat. NaHSO$_3$ (50 mL) and brine (50 mL), dried over Na$_2$SO$_4$, filtered and concentrated to dryness to afford the title product as a yellow oil (0.96 g).

MS (ESI, m/z): 340.0 [M+H$^+$] for C$_{14}$H$_{14}$NOI; t$_R$=0.76 min.

RE1.v. Ethyl 4-(5-(but-2-yn-1-yloxy)-H-indol-1-yl)-2-methyl-2-(methylsulfonyl)butanoate To a solution of intermediate RE1.iv (0.408 g; 1.2 mmol) and ethyl 2-(methylsulfonyl)propanoate (0.268 g, 1.49 mmol) in DMF (2.6 mL) was added Cs$_2$CO$_3$ (0.9 g, 2.67 mmol). The reaction was stirred at 80° C. for 1 h. The solvent was removed under reduced pressure. Water (25 mL) was added, then the two layers were diluted with EA (35 mL). The aq. layer was extracted with EA (3×20 mL). The combined org. layers were washed with brine (40 mL), dried over MgSO$_4$, filtered and concentrated to dryness. The crude product was purified by CC (EA-Hept) to afford the title compound as a white gum (0.31 g).

MS (ESI, m/z): 392.0 [M+H$^+$] for C$_{20}$H$_{25}$NO$_5$S; t$_R$=0.91 min.

RE1.vi. 4-(5-(but-2-yn-1-yloxy)-1H-indol-1-yl)-2-methyl-2-(methylsulfonyl)butanoic acid To an ice-chilled solution of intermediate RE1.v (0.311 g; 0.794 mmol) in THF (7.5 mL), MeOH (1.8 mL) and water (2.2 mL) was added LiOH.H$_2$O (0.129 g, 1.72 mmol). The mixture was stirred at rt overnight. The volatiles were removed in vacuo. The pH was brought to 2 by adding 20% aq. NaHSO$_4$. The aq. layer was extracted with EA (4×20 mL). The combined org. layers were dried over MgSO$_4$ and concentrated to give a brown oil (0.349 g).

MS (ESI, m/z): 364.0 [M+H$^+$] for C$_{18}$H$_{21}$NO$_5$S; t$_R$=0.80 min.

RE1.vii. (RS)-4-(5-(but-2-yn-1-yloxy)-1H-indol-1-yl)-2-methyl-2-(methylsulfonyl)-N-((tetrahydro-2H-pyran-2-yl)oxy)butanamide To a solution of intermediate RE1.vi (0.289 g; 0.794 mmol) in DMF (2.6 mL) were added TEA (0.23 mL, 1.65 mmol), HOBT (0.219 g, 1.62 mmol), O-tetrahydro-2H-pyran-2-yl-hydroxylamine (0.161 g, 1.38 mmol) and EDC (0.229 g, 1.19 mmol). The mixture was stirred at rt overnight. The reaction mixture was concentrated to dryness and the residue was partitioned between water (20 mL) and EA (30 mL). The org. layer was washed with 20% NaHSO$_4$ (20 mL), sat. NaHCO$_3$ (20 mL) and brine (20 mL). The org. layer was dried over MgSO$_4$, filtered and concentrated to dryness to afford the title compound as a brown gum (0.323 g).

MS (ESI, m/z): 463.1 [M+H$^+$] for C$_{23}$H$_{30}$N$_2$O$_6$S; t$_R$=0.87 min.

RE.viii. (RS)-4-(5-(but-2-yn-1-yloxy)-1H-indol-1-yl)-N-hydroxy-2-methyl-2-(methylsulfonyl)butanamide To a suspension of intermediate RE1.vii (0.323 g, 0.698 mmol) in ethanol (6 mL) was added PPTS (0.092 g, 0.366 mmol). The mixture was heated at 80° C. for 90 min. After cooling to rt, water (13 mL) was added. The solvent was evaporated and the residue was purified by prep-HPLC (Method 2) to afford the title compound as a yellow gum (0.077 g).

$^1$H NMR (d6-DMSO) δ: 7.37 (d, J=9.0 Hz, 1H); 7.31 (d, J=3.0 Hz, 1H); 7.08 (d, J=2.3 Hz, 1H); 6.81 (dd, J=2.3, 9.0 Hz, 1H); 6.33 (d, J=3.0 Hz, 1H); 4.67 (d, J=2.3 Hz, 2H); 4.17-4.29 (m, 1H); 3.89-4.01 (m, 1H); 3.00 (s, 3H); 2.56-2.68 (m, 1H); 2.00-2.12 (m, 1H); 1.80 (t, J=2.3 Hz, 3H); 1.53 (s, 3H).

MS (ESI, m/z): 463.1 [M+H$^+$] for C$_{18}$H$_{22}$N$_2$O$_5$S; t$_R$=0.74 min.

Reference Example 2

(RS)-4-(5-(2-fluoro-3-methoxyphenyl)-1H-indazol-1-yl)-N-hydroxy-2-methyl-2-(methylsulfonyl)butanamide

RE2.i. (2RS)-4-(5-(2-fluoro-3-methoxyphenyl)-1H-indazol-1-yl)-2-methyl-2-(methylsulfonyl)-N-((tetrahydro-2H-pyran-2-yl)oxy)butanamide To a solution of the compound of Preparation A (0.188 g; 0.396 mmol) in DME (2 mL) were added (2-fluoro-3-methoxyphenyl)boronic acid (0.094 g; 0.607 mmol), water (1 mL), Na$_2$CO$_3$ (0.178 g; 1.68 mmol; 4.23 eq.) and Pd(PPh$_3$)$_4$ (0.024 g; 0.0203 mmol; 5 mol %). The mixture was stirred at 90° C. for 2 h. Water (10 mL) and EA (20 mL) were added. The two layers were separated and the aq. layer was extracted 3 times with EA (3×20 mL). The combined org. layers were washed with brine, dried over Na$_2$SO$_4$ and concentrated to dryness. The crude product was purified by CC (DCM-MeOH) to afford the desired product as a colourless oil (0.16 g; 78% yield).

MS (ESI, m/z): 520.2 [M+H$^+$] for C$_{25}$H$_{30}$N$_3$O$_6$FS; t$_R$=0.89 min.

RE2.ii. (RS)-4-(5-(2-fluoro-3-methoxyphenyl)-1H-indazol-1-yl)-N-hydroxy-2-methyl-2-(methylsulfonyl)butanamide Starting from intermediate RE2.i (0.161 g; 0.3 mmol) and proceeding in analogy to Reference Example 1, step RE1.viii, the title compound was obtained, after prep-HPLC (Method 2), as a white solid (0.01 g; 7% yield).

$^1$H NMR (d6-DMSO) δ: 10.9 (s, 1H); 9.22 (s, 1H); 8.11 (s, 1H); 7.75-7.88 (m, 2H); 7.03-7.30 (m, 4H); 4.44-4.63 (m, 1H); 4.26-4.37 (m, 1H); 3.87 (s, 3H); 3.00 (s, 3H); 2.68-2.81 (m, 1H); 2.15-2.26 (m, 1H); 1.53 (s, 3H).

MS (ESI, m/z): 435.9 [M+H$^+$] for C$_{18}$H$_{22}$N$_2$O$_5$S; t$_R$=0.76 min.

Reference Example 3

(RS)-(E)-N-hydroxy-2-methyl-2-(methylsulfonyl)-4-(5-styryl-1H-indazol-1-yl)butanamide

RE3.i. (2RS)-2-methyl-2-(methylsulfonyl)-4-(5-((E)-styryl)-1H-indazol-1-yl)-N-((tetrahydro-2H-pyran-2-yl)oxy)butanamide Starting from the compound of Preparation A (0.308 g; 0.65 mmol) and (E)-2-phenylvinylboronic acid (0.105 g; 0.71 mmol; commercial), and proceeding in analogy to Reference Example 2, step RE2.i (78% yield), the title compound was obtained, after purification by CC (EA-Hept), as a yellowish oil (0.252 g).

MS (ESI, m/z): 498.2 [M+H$^+$] for C$_{26}$H$_{31}$N$_3$O$_5$S; t$_R$=0.92 min.

RE3.ii. (RS)-(E)-N-hydroxy-2-methyl-2-(methylsulfonyl)-4-(5-styryl-1H-indazol-1-yl)butanamide Starting from intermediate RE3.i (0.252 g, 0.5 mmol) and proceeding in analogy to Reference Example 1, step RE1.viii, the title compound was obtained, after prep-HPLC (Method 2), as a white solid (0.01 g; 52% yield).

$^1$H NMR (d6-DMSO) δ: 8.07 (s, 1H); 7.88 (s, 1H); 7.73-7.80 (m, 1H); 7.55-7.65 (m, 3H); 7.30-7.40 (m, 3H); 7.17-7.27 (m, 2H); 4.43-4.57 (m, 1H); 4.21-4.36 (m, 1H); 3.01 (s, 3H); 2.66-2.80 (m, 1H); 2.13-2.27 (m, 1H); 1.52 (s, 1H).

MS (ESI, m/z): 414.19 [M+H$^+$] for C$_{20}$H$_{21}$N$_3$O$_4$S; t$_R$=0.80 min.

Reference Example 4

(RS)—N-hydroxy-2-methyl-2-(methylsulfonyl)-4-(5-phenethyl-1H-indazol-1-yl)butanamide

RE4.i. (2RS)-2-methyl-2-(methylsulfonyl)-4-(5-phenethyl-1H-indazol-1-yl)-N-((tetrahydro-2H-pyran-2-yl)oxy)butanamide A solution of intermediate RE3.i (0.295 g, 0.593 mmol) and 10% Pd/C (0.16 g) in EtOH (2 mL), THF (3 mL) and DMF (2 drops) was stirred under hydrogen atmosphere for 2 h at rt. The catalyst was filtered off and thoroughly washed with EA (2×6 mL). The filtrate was evaporated under reduced pressure to give the title product as a colourless oil (0.267 g).

MS (ESI, m/z): 500.1 [M+H$^+$] for $C_{26}H_{33}N_3O_5S$; $t_R$=0.93 min.

RE4.ii. (RS)—N-hydroxy-2-methyl-2-(methylsulfonyl)-4-(5-phenethyl-1H-indazol-1-yl)butanamide Starting from intermediate RE4.i. (0.267 g; 0.53 mmol) and proceeding in analogy to Reference Example 1, step RE1.viii, the title compound was obtained, after prep-HPLC (Method 2) as a white solid (0.035 g; 16% yield).

$^1$H NMR (d6-DMSO) δ: 10.9 (br. s, 1H); 9.23 (br. s, 1H); 7.95 (s, 1H); 7.52 (s, 1H); 7.08-7.33 (m, 7H); 4.37-4.52 (m, 1H); 4.17-4.31 (m, 1H); 3.00 (s, 3H); 2.83-3.03 (m, 4H); 2.62-2.75 (m, 1H); 2.10-2.26 (m, 1H); 1.50 (s, 3H).

MS (ESI, m/z): 416.18 [M+H$^+$] for $C_{26}H_{35}N_3O_5S$; $t_R$=0.80 min.

Reference Example 5

(RS)—N-hydroxy-2-methyl-2-(methylsulfonyl)-4-(5-((4-(morpholinomethyl)phenyl)ethynyl)-1H-indazol-1-yl)butanamide 4-toluenesulfonic acid salt RE5.i. Ethyl (RS) 2-methyl-2-(methylsulfonyl)-4-(5-((4-(morpholinomethyl)phenyl)ethynyl)-1H-indazol-1-yl)butanoate CuI (0.032 g, 0.167 mmol), PdCl$_2$(PPh$_3$)$_2$ (0.061 g; 0.087 mmol), the compound of Preparation B (0.3 g; 0.666 mmol) and 4-(4-ethynylbenzyl)morpholine (0.161 g; 0.799 mmol; prepared as described in WO 2008/154642) were introduced in a two necked round flask. The atmosphere was flushed with nitrogen during 30 min; then degassed THF (4 mL) and degassed TEA (0.325 mL, 2.33 mmol) were added. The suspension was stirred under nitrogen atmosphere at 50° C. for 4 h. Water (15 mL) and EA (30 mL) were added. The aq. layer was extracted once with EA (20 mL). The combined org. layers were washed with brine, dried over MgSO$_4$, and filtered. After concentration to dryness, the residue was filtered (EA) to afford the contaminated title compound (0.565 g; >100% yield).

$^1$H NMR (d6-DMSO) δ: 8.10 (s, 1H); 7.99 (s, 1H); 7.71 (d, J=8.5 Hz, 1H); 7.47-7.58 (m, 4H); 7.34 (d, J=8.2 Hz, 1H); 4.41-4.70 (m, 2H); 3.80-4.05 (overlapped m, 4H); 3.52-3.60 (m, 4H); 3.08 (s, 3H); 2.69-2.87 (m, 1H); 2.30-2.38 (m, 4H); 2.22-2.38 (overlapped m, 1H); 1.61 (s, 3H); 1.06 (t, J=7.3 Hz, 3H).

MS (ESI, m/z): 524.28 [M+H$^+$] for $C_{28}H_{33}N_3O_5S$; $t_R$=0.70 min.

RE5.ii. (RS)—N-hydroxy-2-methyl-2-(methylsulfonyl)-4-(5-((4-(morpholinomethyl)phenyl)ethynyl)-1H-indazol-1-yl)butanamide 4-toluenesulfonic acid salt Starting from intermediate RE5.i (0.565 g) and proceeding in analogy to Reference Example 1, steps RE1.vi to RE1.viii (saponification, THP-ONH$_2$ coupling and deprotection: 15% overall yield), the title compound was obtained, after prep-HPLC (Method 2) as a white solid (0.110 g).

$^1$H NMR (d6-DMSO) δ: 11.0 (s, 1H); 9.77 (br. s, 1H); 9.24 (s, 1H); 8.14 (s, 1H); 8.03 (s, 1H); 7.54-7.73 (m, 6H); 7.46 (d, J=8.0 Hz, 2H); 7.10 (d, J=8.0 Hz, 2H); 4.47-4.60 (m, 1H); 4.25-4.43 (m, 3H); 3.89-4.02 (m, 2H); 3.80-4.05 (overlapped m, 2H); 3.52-3.60 (m, 4H); 3.03 (s, 3H); 2.68-2.81 (m, 1H); 2.27 (s, 3H); 2.22-2.38 (overlapped m, 1H); 1.54 (s, 3H).

MS (ESI, m/z): 511.25 [M+H+] for $C_{26}H_{35}N_3O_5S$; $t_R$=0.48 min.

Reference Example 6

(RS)-4-(5-((4-aminophenyl)ethynyl)-1H-indazol-1-yl)-N-hydroxy-2-methyl-2-(methylsulfonyl)butanamide RE6.i. (R)-4-(5-((4-aminophenyl)ethynyl)-1H-indazol-1-yl)-2-methyl-2-(methylsulfonyl)-N-(2-(trimethylsilyl)ethoxy)butanamide Starting from the compound of Preparation B (0.153 g; 0.34 mmol) and 4-ethynylaniline (0.047 g; 0.4 mmol; commercial), and proceeding in analogy to Reference Example 5, step RE5.i (100% yield) and Reference Example 1, steps RE1.vi to RE1.vii (saponification and TMS-(CH$_2$)$_2$—ONH$_2$ coupling: overall 58% yield), the title compound was obtained, after purification by CC (DCM-MeOH), as a brown oil (0.114 g).

MS (ESI, m/z): 527.25 [M+H+] for $C_{26}H_{34}N_4O_4SSi$; $t_R$=0.90 min.

RE6.ii. (RS)-4-(5-((4-aminophenyl)ethynyl)-1H-indazol-1-yl)-N-hydroxy-2-methyl-2-(methylsulfonyl)butanamide To an ice-chilled solution of intermediate RE6.i (0.115 g, 0.218 mmol) in MeCN (4 mL) was added boron trifluoride etherate (0.248 mL, 1.96 mmol). The mixture stirred at 0° C. for 30 min. The solvent was evaporated under reduced pressure. The residue was purified by prep-HPLC (Method 2) to afford the title product as a yellow foam (0.021 g; 23% yield).

$^1$H NMR (d6-DMSO) δ: 8.37 (br. s, 2H); 8.06 (s, 1H); 7.87 (d, J=1.5 Hz, 1H); 7.62 (d, J=8.7 Hz, 1H); 7.45 (dd, J=1.5, 8.7 Hz, 1H); 7.18 (d, J=8.6 Hz, 1H); 6.54 (br. s, 2H); 4.43-4.55 (m, 1H); 4.23-4.34 (m, 1H); 3.03 (s, 3H); 2.66-2.76 (m, 1H); 2.13-2.24 (overlapped m, 1H); 1.54 (s, 3H).

MS (ESI, m/z): 427.03 [M+H$^+$] for $C_{21}H_{22}N_4O_4S$; $t_R$=0.55 min.

Reference Example 7

(RS)—N-hydroxy-2-methyl-2-(methylsulfonyl)-4-(5-(4-(trifluoromethoxy)phenyl)-1H-indazol-1-yl)butanamide Starting from the compound of Preparation A (0.189 g, 0.40 mmol) and (4-(trifluoromethoxy)phenyl)boronic acid (0.091 g; 0.44 mmol; commercial), and proceeding successively in analogy to Reference Example 2, step RE2.i (100% yield) and Reference Example 1, step RE1.viii (50% yield), the title compound was obtained as a white solid (0.095 g).

$^1$H NMR (d6-DMSO) δ: 11.02 (s, 1H); 9.25 (s, 1H); 8.13 (s, 1H); 8.04 (s, 1H); 7.81 (d, J=8.8 Hz, 2H); 7.73 (s, 2H); 7.44 (d, J=8.1 Hz, 2H); 4.47-4.58 (m, 1H); 4.26-4.38 (m, 1H); 3.01 (s, 3H); 2.68-2.80 (m, 1H); 2.14-2.27 (m, 1H); 1.54 (s, 3H).

MS (ESI, m/z): 472.1 [M+H$^+$] for $C_{20}H_{20}N_3O_5F_3S$; $t_R$=0.80 min.

Reference Example 8

(RS)-4-(5-(4-(2H-1,2,3-triazol-2-yl)phenyl)-1H-indol-1-yl)-N-hydroxy-2-methyl-2-(methylsulfonyl) butanamide formate Starting from the compound of Preparation D (0.407 g; 0.861 mmol) and 2-[4-(4,4,5,5-tetramethyl-1,3,2 dioxaborolan-2-yl)phenyl]-2H-1,2,3-triazole (0.26 g; 0.95 mmol; commercial), and proceeding successively in analogy to Reference Example 2, step RE2.i (33% yield) and Reference Example 1, step RE1.viii (3% yield), the title compound was obtained as a white solid (0.004 g).

$^1$H NMR (d6-DMSO) δ: 11.0 (s, 1H); 9.28 (s, 1H); 8.03-8.14 (m, 4H); 7.82-7.92 (m, 3H); 7.52-7.62 (m, 2H); 7.40-7.46 (m, 2H); 6.53 (br. s, 1H); 4.24-4.42 (m, 1H); 3.97-4.12 (m, 1H); 3.02 (s, 3H); 2.63-2.75 (m, 1H); 2.07-2.16 (m, 1H); 1.54 (s, 3H).

MS (ESI, m/z): 454.2 [M+H+] for $C_{21}H_{22}N_6O_4S$; $t_R$=0.82 min.

Reference Example 9

(RS)—N-hydroxy-2-methyl-2-(methylsulfonyl)-4-(5-(4-(trifluoromethoxy)phenyl)-1H-indol-1-yl)butanamide Starting from the compound of Preparation D (0.19 g; 0.40 mmol) and (4-(trifluoromethoxy)phenyl)boronic acid (0.119 g; 0.59 mmol; commercial), and proceeding successively in analogy to Reference Example 2, step RE2.i (74% yield) and Reference Example 1, step RE1.viii (34% yield), the title compound was obtained as a beige foam (0.047 g).

$^1$H NMR (d6-DMSO) δ: 11.0 (s, 1H); 9.27 (s, 1H); 7.74-7.85 (m, 3H); 7.54-7.59 (m, 1H); 7.37-7.49 (m, 4H); 6.51 (d, J=2.8 Hz, 1H); 4.26-4.40 (m, 1H); 3.96-4.10 (m, 1H); 3.01 (s, 3H); 2.61-2.71 (m, 1H); 2.06-2.20 (m, 1H); 1.59 (s, 3H).

MS (ESI, m/z): 471.1 [M+H$^+$] for $C_{21}H_{21}N_2O_5F_3S$; $t_R$=0.88 min.

Reference Example 10

(RS)-4-(5-(2-fluoro-4-(methylthio)phenyl)-1H-indol-1-yl)-N-hydroxy-2-methyl-2-(methylsulfonyl)butanamide Starting from the compound of Preparation D (0.176 g; 0.37 mmol) and the compound of Preparation C (0.12 g; 0.44 mmol), and proceeding successively in analogy to Reference Example 2, step RE2.i (68% yield) and Reference Example 1, step RE1.viii (45% yield), the title compound was obtained as an off-white solid (0.052 g).

$^1$H NMR (d6-DMSO) δ: 11.0 (s, 1H); 9.27 (s, 1H); 7.68 (s, 1H); 7.55 (d, J=8.6 Hz, 1H); 7.40-7.49 (m, 2H); 7.31 (d, J=8.6 Hz, 1H); 7.13-7.22 (m, 2H); 6.50 (d, J=2.8 Hz, 1H); 4.26-4.39 (m, 1H); 3.97-4.09 (m, 1H); 3.01 (s, 3H); 2.61-2.71 (m, 1H); 2.52 (s, 3H); 2.06-2.20 (m, 1H); 1.58 (s, 3H).

MS (ESI, m/z): 471.1 [M+H$^+$] for $C_{21}H_{23}N_2O_4FS_2$; $t_R$=0.86 min.

Reference Example 11

(RS)-4-(6-fluoro-5-(2-fluoro-4-methoxyphenyl)-1H-indol-1-yl)-N-hydroxy-2-methyl-2-(methylsulfonyl) butanamide Starting from intermediate E.i (0.318 g; 0.757 mmol) and (2-fluoro-4-methoxyphenyl)boronic acid (0.12 g; 0.44 mmol), and proceeding successively in analogy to Reference Example 2, step RE2.i (97% yield), Preparation A, step A.vi (53% yield) and Reference Example 1, step RE1.viii (45% yield), the title compound was obtained, after purification by CC (DCM-MeOH), as an off-white foam (0.148 g).

$^1$H NMR (d6-DMSO) δ: 11.07 (br. s, 1H); 9.30 (br. s, 1H); 7.52 (d, J=7.3 Hz, 1H); 7.46-7.40 (m, 2H); 7.35 (t, J=8.5 Hz, 1H); 6.96-6.83 (m, 2H); 6.50 (d, J=3.1 Hz, 1H); 4.38-4.21 (m, 1H); 4.07-3.88 (m, 1H); 3.82 (s, 3H); 3.03 (s, 3H); 2.75-2.56 (m, 1H); 2.22-2.04 (m, 1H); 1.60 (s, 3H).

MS (ESI, m/z): 453.01 [M+H$^+$] for $C_{21}H_{22}N_2O_5F_2S$; $t_R$=0.83 min.

Reference Example 12

(RS)-4-(4-fluoro-5-(2-fluoro-4-methoxyphenyl)-1H-indol-1-yl)-N-hydroxy-2-methyl-2-(methylsulfonyl) butanamide Starting from the compound of Preparation H (0.104 g, 0.192 mmol) and (2-fluoro-4-methoxyphenyl)boronic acid (0.041 g; 0.24 mmol), and proceeding successively in analogy to Reference Example 2, step RE2.i and Reference Example 1, step RE1.viii, the title compound was obtained, after precipitation from water as an off-white solid (0.020 g; Suzuki coupling: 42% yield; deprotection using PPTS: 56% yield).

$^1$H NMR (d6-DMSO) δ: 11.06 (br. s, 1H); 9.29 (br. s, 1H); 7.48 (d, J=3.2 Hz, 1H); 7.43-7.32 (m, 2H); 7.13 (t, J=7.3 Hz, 1H); 6.97-6.86 (m, 2H); 6.56 (d, J=2.9 Hz, 1H); 4.44-4.30 (m, 1H); 4.10-3.98 (m, 1H); 3.82 (s, 3H); 3.03 (s, 3H); 2.76-2.60 (m, 1H); 2.23-2.11 (m, 1H); 1.60 (s, 3H).

MS (ESI, m/z): 452.99 [M+H$^+$] for $C_{21}H_{22}N_2O_5F_2S$; $t_R$=0.83 min.

Reference Example 13

(RS)-4-(4-fluoro-5-((4-(3-hydroxyoxetan-3-yl)phenyl)ethynyl)-1H-indol-1-yl)-N-hydroxy-2-methyl-2-(methylsulfonyl)butanamide RE13.i. 3-(4-iodophenyl)oxetan-3-ol A solution of 1,4-diiodobenzene (0.800 g, 2.43 mmol) in THF (8 mL) was treated at −78° C. with BuLi (1.68M in Hex; 2.23 mL). After stirring at this temperature for 30 min, the solution was treated with a suspension of 3-oxetanone (0.24 g, 3.34 mmol) in THF (3 mL). The reaction mixture was allowed to reach rt and was further stirred overnight. The reaction mixture was treated with a 10% aq. NaHSO$_4$ solution (4 mL) and diluted water and EA. The aq. layer was extracted with EA. The combined org. layers were washed with brine, dried over MgSO$_4$, filtered and concentrated under reduced pressure. The residue was purified by CC (Hept-EA) to afford the title alcohol as a colourless solid (0.2 g; 55% yield).

$^1$H NMR (d6-DMSO) δ: 7.73 (d, J=8.5 Hz, 2H); 7.39 (d, J=8.5 Hz, 2H); 6.39 (s, 1H); 4.73 (d, J=6.8 Hz, 2H); 4.60 (d, J=6.8 Hz, 2H).

RE13.ii. 3-(4-((trimethylsilyl)ethynyl)phenyl)oxetan-3-ol

Intermediate RE13.i (1 g; 3.63 mmol), CuI (0.14 g; 0.73 mmol), PdCl$_2$(PPh$_3$)$_2$ (0.26 g; 0.37 mmol), THF (26 mL), trimethylsilylacetylene (0.57 mL; 3.99 mmol) and TEA (1.27 mL, 9.07 mmol) were successively introduced in a flask. The suspension was stirred at 50° C. for 1.5 h. After cooling and concentration to dryness, the residue was purified by CC (Hept-EA) to afford the title compound (0.9 g, 100% yield).

$^1$H NMR (d6-DMSO) δ: 7.61 (d, J=8.3 Hz, 2H); 7.48 (d, J=8.3 Hz, 2H); 6.43 (s, 1H); 4.77 (d, J=6.7 Hz, 2H); 4.64 (d, J=6.7 Hz, 2H); 0.23 (s, 9H).

RE13.iii. 3-(4-ethynylphenyl)oxetan-3-ol

Intermediate RE13.ii (0.9 g, 3.65 mmol) was dissolved in MeOH (15 mL), treated with $K_2CO_3$ (0.9 g) and further stirred at rt for 90 min. The reaction mixture was diluted with DCM and washed with water. The aq. layer was extracted with DCM. The combined org. layers were washed with brine, dried over $MgSO_4$, filtered and concentrated under reduced pressure to afford the terminal alkyne as a brown oil (0.55 g; 86% yield).

$^1$H NMR (d6-DMSO) δ: 7.56-7.61 (m, 2H); 7.45-7.51 (m, 2H); 6.40 (s, 1H); 4.75 (d, J=6.8 Hz, 2H); 4.63 (d, J=6.8 Hz, 2H); 4.13 (s, 1H).

RE13.iv. (RS)-4-(4-fluoro-5-((4-(3-hydroxyoxetan-3-yl)phenyl)ethynyl)-1H-indol-1-yl)-N-hydroxy-2-methyl-2-(methylsulfonyl)butanamide Starting from the compound of Preparation H (0.276 g, 0.63 mmol) and intermediate RE13.iii (0.203 g; 0.73 mmol), and proceeding successively in analogy to Reference Example 2, step RE2.i (51% yield) and Reference Example 1, step RE1.viii (26% yield), the title compound was obtained, after purification by prep-HPLC (Method 2), as a brownish solid (0.042 g).

$^1$H NMR (d6-DMSO) δ: 7.73-7.51 (m, 5H); 7.44-7.28 (m, 2H); 6.60 (m, 1H); 6.45 (m, 1H); 4.79 (d, J=6.1 Hz, 2H); 4.68 (d, J=6.1 Hz, 2H); 4.45-4.28 (m, 1H); 4.13-3.96 (m, 1H); 3.03 (s, 3H); 2.76-2.59 (m, 1H); 2.23-2.08 (m, 1H); 1.59 (s, 3H).

MS (ESI, m/z): 501.01 [M+H$^+$] for $C_{25}H_{25}N_2O_6FS$; $t_R$=0.75 min.

EXAMPLES OF COMPOUNDS ACCORDING TO THE INVENTION

Example 1

(R)-4-(5-(2-fluoro-4-(methylthio)phenyl)-1H-indazol-1-yl)-N-hydroxy-2-methyl-2-(methylsulfonyl)butanamide Starting from the compound of Preparation I (0.106 g, 0.2 mmol) and the compound of Preparation C (0.07 g; 0.26 mmol), and proceeding successively in analogy to Reference Example 2, step RE2.i (100% yield) and Reference Example 1, step RE1.viii (31% yield), the title compound was obtained, after purification by prep-HPLC (Method 2), as a white solid (0.029 g).

$^1$H NMR (d6-DMSO) δ: 8.12 (s, 1H); 7.88 (s, 1H); 7.65-7.72 (m, 1H); 7.43-7.58 (m, 2H); 7.12-7.25 (m, 2H); 4.42-4.59 (m, 1H); 4.25-4.39 (m, 1H); 3.01 (s, 3H); 2.67-2.80 (m, 1H); 2.51 (overlapped s, 3H); 2.14-2.28 (m, 1H); 1.53 (s, 3H).

MS (ESI, m/z): 452.1 [M+H+] for $C_{20}H_{22}N_3O_4FS_2$; $t_R$=0.83 min.

Example 2

(R)-4-(5-(2-fluoro-4-methoxyphenyl)-1H-indol-1-yl)-N-hydroxy-2-methyl-2-(methylsulfonyl)butanamide 2.i. (RS)-4-(5-(2-fluoro-4-methoxyphenyl)-1H-indol-1-yl)-N-hydroxy-2-methyl-2-(methylsulfonyl)butanamide Starting from the compound of Preparation D (0.204 g, 0.43 mmol) and (2-fluoro-4-methoxyphenyl)boronic acid (0.151 g; 0.89 mmol; commercial), and proceeding successively in analogy to Reference Example 2, step RE2.i (87% yield) and Reference Example 1, step RE1.viii (67% yield), the title compound was obtained as a beige solid (0.095 g).

$^1$H NMR (d6-DMSO) δ: 11.0 (br. s, 1H); 9.27 (br. s, 1H); 7.64 (br. s, 1H); 7.53 (d, J=8.6 Hz, 1H); 7.38-7.46 (m, 2H); 7.27 (d, J=8.6 Hz, 1H); 6.82-6.92 (m, 2H); 6.48 (d, J=3.1 Hz, 1H); 4.25-4.38 (m, 1H); 3.96-4.08 (m, 1H); 3.16 (s, 3H); 3.14 (s, 3H); 2.61-2.73 (m, 1H); 2.07-2.20 (m, 1H); 1.58 (s, 3H).

MS (ESI, m/z): 435.1 [M+H$^+$] for $C_{21}H_{23}N_2O_5FS$; $t_R$=0.82 min.

2.ii. (R)-4-(5-(2-fluoro-4-methoxyphenyl)-1H-indol-1-yl)-N-hydroxy-2-methyl-2-(methylsulfonyl)butanamide Intermediate 2.i (0.05 g) was separated by semi-preparative chiral HPLC Method C (MeCN-MeOH-EtOH-TFA 8-1-1-0.002; flow rate: 24 mL/min; UV detection at 210 nm), the respective retention times of analytical samples (flow rate: 1.2 mL/min) were 6.3 and 10.4 min. The title (R)-enantiomer, identified as the second eluting compound, was obtained as a beige solid (0.014 g).

MS (ESI, m/z): 435.1 [M+H$^+$] for $C_{21}H_{23}N_2O_5FS$; $t_R$=0.82 min.

Example 3

(R)-4-(5-(2-fluoro-4-methoxyphenyl)-1H-indazol-1-yl)-N-hydroxy-2-methyl-2-(methylsulfonyl)butanamide 3.i. 5-(2-fluoro-4-methoxyphenyl)-1H-indazole Starting from 5-bromo-1H-indazole (9.1 g, 46.2 mmol; commercial) and (2-fluoro-4-methoxyphenyl)boronic acid (8.24 g; 48.5 mmol) and proceeding in analogy to Reference Example 2, step RE2.i, the title compound was obtained, after purification by CC (Hept-EA) as a white solid (7.74 g; 69% yield).

$^1$H NMR (d6-DMSO) δ: 13.12 (br. s, 1H); 8.13 (s, 1H); 7.86 (s, 1H); 7.57-7.63 (m, 1H); 7.41-7.52 (m, 2H); 6.84-6.98 (m, 2H); 3.82 (s, 3H).

MS (ESI, m/z): 243.2 [M+H$^+$] for $C_{14}H_{11}N_2OF$; $t_R$=0.84 min.

3.ii. (R)-4-(5-(2-fluoro-4-methoxyphenyl)-1H-indazol-1-yl)-N-hydroxy-2-methyl-2-(methylsulfonyl)butanamide Starting from intermediate 3.i (4.07 g, 15.1 mmol) and proceeding in analogy to Preparation I, step I.1 (alkylation:

69% yield), Preparation A, step A.vi (saponification and coupling with THPO-NH$_2$: 33% yield) and Reference Example 1, step RE1.viii (deprotection with PPTS: 88% yield), the title compound was obtained, after precipitation from water, as a white solid (3.04 g).

$^1$H NMR (d6-DMSO) δ: 11.0 (br. s, 1H); 9.24 (br. s, 1H); 8.11 (d, J=0.4 Hz, 1H); 7.84 (s, 1H); 7.68 (m, 1H); 7.42-7.54 (m, 2H); 6.84-6.97 (m, 2H); 4.45-4.59 (m, 1H); 4.24-4.37 (m, 1H); 3.01 (s, 3H); 2.67-2.79 (m, 1H); 2.15-2.27 (m, 1H); 1.53 (s, 3H).

MS (ESI, m/z): 436.1 [M+H$^+$] for C$_{21}$H$_{23}$N$_2$O$_5$FS; $t_R$=0.77 min.

Example 4

(R)—N-hydroxy-4-(5-((4-(hydroxymethyl)phenyl)ethynyl)-1H-indazol-1-yl)-2-methyl-2-(methylsulfonyl)butanamide Starting from the compound of Preparation J (0.143 g; 0.34 mmol) and 4-iodobenzyl alcohol (0.091 g, 0.39 mmol; commercial), and proceeding in analogy to Reference Example 5, step RE5.i (86% yield) and Reference Example 1, step RE1.viii (49% yield), the title compound was obtained, after purification by prep-HPLC (Method 2), as a yellowish foam (0.062 g).

$^1$H NMR (d6-DMSO) δ: 11.01 (s, 1H); 9.24 (s, 1H); 8.11 (s, 1H); 7.99 (s, 1H); 7.68 (d, J=8.6 Hz, 1H); 7.46-7.57 (m, 3H); 7.31-7.38 (m, 2H); 5.24 (t, J=5.9 Hz, 1H); 4.46-4.58 (m, 3H); 4.23-4.36 (m, 1H); 3.02 (s, 1H); 2.66-2.81 (m, 1H); 2.13-2.28 (m, 1H); 1.53 (s, 3H).

MS (ESI, m/z): 441.97 [M+H$^+$] for C$_{22}$H$_{23}$N$_3$O$_5$S; $t_R$=0.70 min.

Example 5

(R)—N-hydroxy-4-(5-((3-hydroxyoxetan-3-yl)buta-1,3-diyn-1-yl)-1H-indazol-1-yl)-2-methyl-2-(methylsulfonyl)butanamide Starting from the compound of Preparation J (0.136 g; 0.32 mmol) and the compound of Preparation K (0.083 g; 0.37 mmol), and proceeding in analogy to Reference Example 5, step RE5.i (93% yield) and Reference Example 1, step RE1.viii (39% yield), the title compound was obtained, after purification by prep-HPLC (Method 2), as a brownish foam (0.051 g).

$^1$H NMR (d6-DMSO) δ: 8.13 (s, 1H); 8.08 (s, 1H); 7.68 (d, J=8.5 Hz, 1H); 7.54 (d, J=8.5 Hz, 1H); 6.72 (s, 1H); 4.70 (d, J=6.7 Hz, 2H); 4.45-4.58 (m, 3H); 4.23-4.36 (m, 1H); 3.98-4.12 (m, 1H); 3.00 (s, 3H); 2.64-2.80 (m, 1H); 2.13-2.28 (m, 1H); 1.52 (s, 3H).

MS (ESI, m/z): 431.93 [M+H$^+$] for C$_{20}$H$_{21}$N$_3$O$_6$S; $t_R$=0.64 min.

Example 6

(R)-4-(5-(4-(2H-1,2,3-triazol-2-yl)phenyl)-1H-indazol-1-yl)-N-hydroxy-2-methyl-2-(methylsulfonyl)butanamide Starting from the compound of Preparation I (0.109 g; 0.21 mmol) and 2-[4-(4,4,5,5-tetramethyl-1,3,2-dioxaborolan-2-yl)phenyl]-2H-1,2,3-triazole (0.044 g; 0.31 mmol; commercial), and proceeding successively in analogy to Reference Example 2, step RE2.i (100% yield) and Reference Example 1, step RE1.viii (9% yield), the title compound was obtained as a white solid (0.019 g).

$^1$H NMR (d6-DMSO) δ: 11.0 (s, 1H); 9.25 (s, 1H); 8.06-8.16 (m, 6H); 7.91 (d, J=8.6 Hz, 2H); 7.79 (m, 1H); 7.74 (m, 1H); 7.85-7.89 (m, 2H); 7.67-7.71 (m, 1H); 7.58-7.63 (m, 1H); 4.48-4.60 (m, 1H); 4.26-4.38 (m, 1H); 3.01 (s, 3H); 2.68-2.80 (m, 1H); 2.16-2.28 (m, 1H); 1.54 (s, 3H).

MS (ESI, m/z): 455.2 [M+H$^+$] for C$_{21}$H$_{22}$N$_6$O$_4$S; $t_R$=0.73 min.

Example 7

(R)—N-hydroxy-4-(5-(5-hydroxy-5-methylhexa-1,3-diyn-1-yl)-1H-indazol-1-yl)-2-methyl-2-(methylsulfonyl)butanamide Starting from the compound of Preparation J (0.159 g; 0.38 mmol) and 4-iodo-2-methylbut-3-yn-2-ol (0.091 g; 0.43 mmol; prepared as reported by Rajender Reddy et al. in *Tetrahedron Lett.* (2010), 51, 2170-2173), and proceeding in analogy to Reference Example 5, step RE5.i (100% yield) and Reference Example 1, step RE1.viii (13% yield), the title compound was obtained, after purification by prep-HPLC (Method 2), as a yellow solid (0.024 g).

$^1$H NMR (d6-DMSO) δ: 10.9 (s, 1H); 9.22 (s, 1H); 8.12 (s, 1H); 8.03 (s, 1H); 7.66 (d, J=8.8 Hz, 1H); 7.52 (d, J=8.8 Hz, 1H); 4.44-4.58 (m, 1H); 4.22-4.38 (m, 1H); 3.00 (s, 3H); 2.63-2.76 (m, 1H); 2.11-2.26 (m, 1H); 1.51 (s, 3H); 1.41 (s, 6H).

MS (ESI, m/z): 417.9 [M+H$^+$] for C$_{20}$H$_{23}$N$_3$O$_5$S; $t_R$=0.70 min.

Example 8

(R)—N-hydroxy-4-(5-((4-(2-hydroxypropan-2-yl)phenyl)ethynyl)-1H-indazol-1-yl)-2-methyl-2-(methylsulfonyl)butanamide Starting from the compound of Preparation I (0.16 g; 0.38 mmol) and 2-(4-ethynylphenyl)propan-2-ol (0.114 g; 0.435 mmol; prepared as described in WO 2006/099972), and proceeding in analogy to Reference Example 5, step RE5.i (100% yield) and Reference Example 1, step RE1.viii (40% yield), the title compound was obtained, after purification by prep-HPLC (Method 1), as a yellow solid (0.073 g).

$^1$H NMR (d6-DMSO) δ: 11.0 (s, 1H); 9.23 (s, 1H); 8.11 (s, 1H); 7.98 (s, 1H); 7.67 (d, J=9.1 Hz, 1H); 7.41-7.57 (overlapped m, 5H); 4.43-4.57 (m, 1H); 4.22-4.36 (m, 1H); 3.01 (s, 3H); 2.66-2.79 (m, 1H); 2.12-2.27 (m, 1H); 1.52 (s, 3H); 1.41 (m, 6H).

MS (ESI, m/z): 469.9 [M+H$^+$] for C$_{24}$H$_{27}$N$_3$O$_5$S; $t_R$=0.74 min.

Example 9

(R)—N-hydroxy-4-(5-((4-(hydroxymethyl)phenyl)ethynyl)-1H-indol-1-yl)-2-methyl-2-(methylsulfonyl)butanamide Starting from the compound of Preparation L (0.2 g; 0.4 mmol) and (4-ethynylphenyl)methanol (0.064 g, 0.48 mmol; commercial), and proceeding in analogy to Reference Example 5, step RE5.i (93% yield) and Reference Example 1, step RE1.viii (35% yield), the title compound was obtained, after purification by prep-HPLC (Method 2), as a beige solid (0.058 g).

¹H NMR (d6-DMSO) δ: 11.0 (m, 1H); 9.27 (m, 1H); 7.76 (m, 1H); 7.57-7.39 (m, 4H); 7.57-7.39 (m, 3H); 6.47 (m, 1H); 5.23 (t, J=5.8 Hz, 1H); 4.50 (d, 2H); 4.37-4.25 (m, 1H); 4.07-3.95 (m, 1H); 3.01 (m, 3H); 2.72-2.60 (m, 1H); 2.19-2.06 (m, 1H); 1.57 (m, 3H).
MS (ESI, m/z): 441.2 [M+H$^+$] for $C_{23}H_{24}N_2O_5S$; $t_R$=0.74 min.

Example 10

(R)—N-hydroxy-4-(5-((4-(3-hydroxyoxetan-3-yl)phenyl)ethynyl)-1H-indol-1-yl)-2-methyl-2-(methylsulfonyl)butanamide Starting from the compound of Preparation L (0.189 g; 0.365 mmol) and intermediate RE13.iii (0.078 g; 0.4 mmol), and proceeding in analogy to Reference Example 5, step RE5.i (100% yield) and Reference Example 1, step RE1.viii (53% yield), the title compound was obtained, after purification by prep-HPLC (Method 2), as a off-white solid (0.104 g).
¹H NMR (d6-DMSO) δ: 11.05 (m, 1H); 9.29 (m, 1H); 7.80 (m, 1H); 7.64 (m, 2H); 7.56 (m, 3H); 7.48 (m, 1H); 7.34 (d, J=8.3 Hz, 1H); 6.50 (d, J=3.1 Hz, 1H); 6.46 (s, 1H); 4.79 (d, J=6.4 Hz, 2H); 4.68 (d, J=6.4 Hz, 2H); 4.39-4.28 (m, 1H); 4.07-3.97 (m, 1H); 3.03 (s, 3H); 2.74-2.62 (m, 1H); 2.18-2.08 (m, 1H); 1.59 (s, 3H).
MS (ESI, m/z): 483.1 [M+H$^+$] for $C_{25}H_{26}N_2O_6S$; $t_R$=0.73 min.

Example 11

(R)—N-hydroxy-4-(5-((3-hydroxyoxetan-3-yl)buta-1,3-diyn-1-yl)-1H-indol-1-yl)-2-methyl-2-(methylsulfonyl)butanamide Starting from the compound of Preparation M (0.141 g, 0.36 mmol) and the compound of Preparation K (0.087 g; 0.39 mmol), and proceeding in analogy to Reference Example 5, step RE5.i (45% yield) and Reference Example 1, step RE1.viii (46% yield), the title compound was obtained, after purification by prep-HPLC (Method 2), as a brownish foam (0.030 g).
¹H NMR (d6-DMSO) δ: 11.05 (br. s, 1H); 9.28 (br. s, 1H); 7.84 (s, 1H); 7.58-7.47 (m, 2H); 7.35 (d, J=8.8 Hz, 1H); 6.74 (s, 1H); 6.50 (d, J=2.3 Hz, 1H); 4.72 (d, J=6.3 Hz, 2H); 4.56 (d, J=6.3 Hz, 2H); 4.39-4.28 (m, 1H); 4.07-3.95 (m, 1H); 3.02 (s, 3H); 2.71-2.60 (m, 1H); 2.17-2.06 (m, 1H); 1.57 (s, 3H).
MS (ESI, m/z): 431.1 [M+H$^+$] for $C_{21}H_{22}N_2O_6S$; $t_R$=0.70 min.

Example 12

(R)—N-hydroxy-4-(5-((4-(3-hydroxyoxetan-3-yl)phenyl)ethynyl)-1H-indazol-1-yl)-2-methyl-2-(methylsulfonyl)butanamide Starting from the compound of Preparation J (0.151 g; 0.36 mmol) and intermediate RE13.i (0.113 g; 0.41 mmol), and proceeding in analogy to Reference Example 5, step RE5.i (90% yield) and Reference Example 1, step RE1.viii (53% yield), the title compound was obtained, after purification by prep-HPLC (Method 2), as a white solid (0.058 g).
¹H NMR (d6-DMSO) δ: 8.12 (s, 1H); 8.01 (s, 1H); 7.51-7.73 (m, 6H); 6.42 (s, 1H); 4.77 (d, J=6.4 Hz, 2H); 4.66 (d, J=6.4 Hz, 2H); 4.43-4.58 (m, 1H); 4.20-4.39 (m, 1H); 3.02 (s, 3H); 2.67-2.84 (m, 1H); 2.14-2.27 (m, 1H); 1.53 (s, 3H).
MS (ESI, m/z): 483.9 [M+H$^+$] for $C_{25}H_{26}N_2O_6S$; $t_R$=0.69 min.

Example 13

(R)—N-hydroxy-4-(5-((3-hydroxythietan-3-yl)buta-1,3-diyn-1-yl)-1H-indazol-1-yl)-2-methyl-2-(methylsulfonyl)butanamide Starting from the compound of Preparation J (0.154 g; 0.36 mmol) and the compound of Preparation N (0.113 g; 0.41 mmol), and proceeding in analogy to Reference Example 5, step RE5.i (94% yield) and Reference Example 1, step RE1.viii (38% yield), the title compound was obtained, after purification by prep-HPLC (Method 2), as a white solid (0.058 g).
¹H NMR (d6-DMSO) δ: 10.9 (s, 1H); 9.21 (s, 1H); 8.13 (s, 1H); 8.08 (s, 1H); 7.68 (d, J=8.8 Hz, 1H); 7.56 (d, J=8.8 Hz, 1H); 6.78 (s, 1H); 4.43-4.59 (m, 1H); 4.21-4.36 (m, 1H); 3.48 (d, J=10.0 Hz, 2H); 3.36 (d, J=10.0 Hz, 2H); 3.00 (s, 3H); 2.64-2.78 (m, 1H); 2.06-2.27 (m, 1H); 1.52 (s, 3H).
MS (ESI, m/z): 447.9 [M+H$^+$] for $C_{20}H_{21}N_3O_5S_2$; $t_R$=0.72 min.

Example 14

(R)—N-hydroxy-4-(5-((4-(2-hydroxyethyl)phenyl)ethynyl)-1H-indazol-1-yl)-2-methyl-2-(methylsulfonyl)butanamide Starting from the compound of Preparation J (0.154 g; 0.36 mmol) and 2-(4-iodophenyl)ethanol (0.103 g; 0.41 mmol; commercial), and proceeding in analogy to Reference Example 5, step RE5.i (85% yield) and Reference Example 1, step RE1.viii (48% yield), the title compound was obtained, after purification by prep-HPLC (Method 2), as a yellow solid (0.068 g).
¹H NMR (d6-DMSO) δ: 11.0 (s, 1H); 9.23 (s, 1H); 8.10 (s, 1H); 7.98 (s, 1H); 7.67 (d, J=8.6 Hz, 1H); 7.53 (d, J=8.6 Hz, 1H); 7.44 (d, J=7.9 Hz, 2H); 7.25 (d, J=7.9 Hz, 2H); 4.41-4.59 (m, 1H); 4.22-4.35 (m, 1H); 3.60 (t, J=6.8 Hz, 2H); 3.01 (s, 3H); 2.64-2.80 (overlapped m, 3H); 2.10-2.27 (m, 1H); 1.52 (s, 3H).
MS (ESI, m/z): 456.0 [M+H$^+$] for $C_{23}H_{25}N_3O_5S$; $t_R$=0.71 min.

Example 15

(R)-4-(6-fluoro-5-((4-(3-hydroxyoxetan-3-yl)phenyl)ethynyl)-1H-indol-1-yl)-N-hydroxy-2-methyl-2-(methylsulfonyl)butanamide 15.i. (RS)-4-(6-fluoro-5-((4-(3-hydroxyoxetan-3-yl)phenyl)ethynyl)-1H-indol-1-yl)-N-hydroxy-2-methyl-2-(methylsulfonyl)butanamide Starting from the compound of Preparation O (0.306 g, 0.84 mmol) and intermediate RE13.i (0.264 g; 0.95 mmol), and proceeding in analogy to Reference Example 5, step RE5.i (88% yield) and Example 1, steps RE1.vi to RE1.viii (saponification, THP-ONH$_2$ coupling, deprotection: overall 41% yield), the title compound was obtained, after prep-HPLC (Method 2), as a white solid (0.151 g).

¹H NMR (d6-DMSO) δ: 11.05 (br. s, 1H); 9.27 (br. s, 1H); 7.80 (d, J=7.0 Hz, 1H); 7.64 (d, J=8.2 Hz, 2H); 7.56 (d, J=8.2 Hz, 2H); 7.50-7.43 (m, 2H); 6.49 (m, 1H); 6.42 (m, 1H); 4.77 (d, J=6.7 Hz, 2H); 4.67 (d, J=6.7 Hz, 2H); 4.37-4.18 (m, 1H); 4.03-3.86 (m, 1H). 3.01 (s, 3H); 2.75-2.55 (m, 1H); 2.18-2.00 (m, 1H); 1.57 (s, 3H).

MS (ESI, m/z): 501.1 [M+H⁺] for $C_{25}H_{25}N_2O_6FS$; $t_R$=0.75 min.

15.ii. (R)-4-(6-fluoro-5-((4-(3-hydroxyoxetan-3-yl) phenyl)ethynyl)-1H-indol-1-yl)-N-hydroxy-2-methyl-2-(methylsulfonyl)butanamide Intermediate 15.i (0.150 g) was separated by semi-preparative chiral HPLC Method A (Hept-EtOH-TFA-DEA 1-1-0.01-0.05; flow rate: 20 mL/min; UV detection at 276 nm), the respective retention times (flow rate: 1.0 mL/min) were 10.1 and 12.9 min. The title (R)-enantiomer, identified as the second eluting compound, was collected as a beige solid (0.052 g; 41% yield).

¹H NMR (d6-DMSO) δ: 11.05 (br. s, 1H); 9.27 (br. s, 1H); 7.80 (d, J=7.0 Hz, 1H); 7.64 (d, J=8.2 Hz, 2H); 7.56 (d, J=8.2 Hz, 2H); 7.50-7.43 (m, 2H); 6.49 (m, 1H); 6.42 (m, 1H); 4.77 (d, J=6.7 Hz, 2H); 4.67 (d, J=6.7 Hz, 2H); 4.37-4.18 (m, 1H); 4.03-3.86 (m, 1H). 3.01 (s, 3H); 2.75-2.55 (m, 1H); 2.18-2.00 (m, 1H); 1.57 (s, 3H).

MS (ESI, m/z): 501.1 [M+H+] for $C_{25}H_{25}N_2O_6FS$; $t_R$=0.75 min.

Example 16

(R)—N-hydroxy-4-(5-((4-((R)-1-hydroxyethyl)phenyl)ethynyl)-1H-indazol-1-yl)-2-methyl-2-(methylsulfonyl)butanamide hydrochloride Starting from the compound of Preparation J (0.157 g; 0.374 mmol) and (R)-1-(4-iodophenyl)ethan-1-ol (0.106 g; 0.427 mmol; commercial), and proceeding successively in analogy to Reference Example 5, step RE5.i (88% yield) and Reference Example 1, step RE1.viii (32% yield), the title compound was obtained as a beige solid (0.050 g) recovered by filtration from water.

¹H NMR (d6-DMSO) δ: 11.0 (s, 1H); 9.23 (s, 1H); 8.11 (s, 1H); 7.98 (s, 1H); 7.67 (d, J=8.8 Hz, 1H); 7.45-7.56 (m, 3H); 7.32-7.40 (m, 2H); 4.67-4.77 (m, 1H); 4.44-4.58 (m, 1H); 4.21-4.35 (m, 1H); 3.01 (s, 3H); 2.66-2.85 (m, 1H); 2.11-2.31 (m, 1H); 1.53 (s, 1H); 1.31 (d, J=6.7 Hz, 3H).

MS (ESI, m/z): 455.9 [M+H+] for $C_{23}H_{25}N_3O_5S$; $t_R$=0.70 min.

Example 17

(R)—N-hydroxy-4-(5-(((1S,2S)-2-(hydroxymethyl) cyclopropyl)buta-1,3-diyn-1-yl)-1H-indol-1-yl)-2-methyl-2-(methylsulfonyl)butanamide 17.i. ((1S,2S)-2-((1-((3R)-3-methyl-3-(methylsulfonyl)-4-oxo-4-(((tetrahydro-2H-pyran-2-yl)oxy) amino)butyl)-1H-indol-5-yl)buta-1, 3-diyn-1-yl) cyclopropyl)methyl acetate Starting from the compound of Preparation M (0.141 g; 0.36 mmol) and the (1S,2S)-configured compound of Preparation P, (0.088 g; 0.39 mmol), and proceeding in analogy to Reference Example 5, step RE5.i, the title compound was obtained, after purification by CC (Hept-EA), as a brownish oil (0.076 g; 43% yield).

¹H NMR (d6-DMSO) δ: 11.45 (m, 1H); 7.86-7.76 (m, 1H); 7.66-7.46 (m, 2H); 7.38-7.26 (m, 1H); 6.50 (m, 1H); 5.00 (m, 1H); 4.36-4.23 (m, 1H); 4.09-3.91 (m, 3H); 3.86-3.79 (m, 1H); 3.63-3.43 (m, 1H); 3.03 (s, 1.5H); 3.01 (s, 1.5H); 2.75-2.60 (m, 1H); 2.22-2.06 (m, 1H); 2.04-1.98 (m, 3H); 1.72 (m, 3H); 1.58 (m, 6H); 1.23 (m, 1H); 1.17 (t, J=7.3 Hz, 1H); 1.11-0.90 (m, 2H).

MS (ESI, m/z): 555.1 [M+H⁺] for $C_{29}H_{34}N_2O_7S$; $t_R$=0.70 min.

17.ii. (2R)-4-(5-(((1S,2S)-2-(hydroxymethyl)cyclopropyl)buta-1, 3-diyn-1-yl)-1H-indol-1-yl)-2-methyl-2-(methylsulfonyl)-N-((tetrahydro-2H-pyran-2-yl)oxy)butanamide To a solution of intermediate 17.i (0.0765 g; 0.138 mmol) in MeOH (0.7 mL) was added $K_2CO_3$ (0.0381 g; 0.276 mmol). The suspension was stirred at rt for 30 min. The reaction mixture was diluted with DCM (6 mL) and washed with water (10 mL). The aq. layer was extracted with DCM-MeOH (9-1, 3×10 mL). The combined org. layers were dried over $MgSO_4$, filtered and evaporated under reduced pressure to afford the title compound (0.063 g; 89% yield).

¹H NMR (d6-DMSO) δ: 11.44 (m, 1H); 7.85-7.76 (m, 1H); 7.65-7.45 (m, 2H); 7.37-7.28 (m, 1H); 6.53-6.47 (m, 1H); 5.03 (m, 1H); 4.68 (t, J=5.9 Hz, 1H); 4.41-4.25 (m, 1H); 4.15-3.99 (m, 2H); 3.58-3.35 (m, 2H); 3.30-3.22 (overlapped m, 1H); 3.02 (m, 3H); 2.69-2.50 (m, 1H); 2.20-2.08 (m, 1H); 1.71 (m, 3H); 1.56 (m, 6H); 1.45-1.35 (m, 1H); 1.27-1.20 (m, 1H); 0.88 (m, 2H).

MS (ESI, m/z): 512.96 [M+H+] for $C_{27}H_{32}N_2O_6S$; $t_R$=0.87 min.

17.iii. (R)—N-hydroxy-4-(5-(((1S,2S)-2-(hydroxymethyl)cyclopropyl)buta-1,3-diyn-1-yl)-1H-indol-1-yl)-2-methyl-2-(methylsulfonyl)butanamide Starting from intermediate 17.ii (0.063 g, 0.12 mmol) and proceeding in analogy to Reference Example 1, step RE1.viii (34% yield), the title compound was obtained, after purification by prep-HPLC (Method 2), as a beige solid (0.018 g).

¹H NMR (d6-DMSO) δ: 9.27 (br. s, 1H); 7.76 (s, 1H); 7.52-7.45 (m, 2H); 7.28 (d, J=8.5 Hz, 1H); 6.48 (d, J=2.7 Hz, 1H); 4.67 (t, J=5.6 Hz, 1H); 4.38-4.24 (m, 1H); 4.08-3.94 (m, 1H); 3.46-3.34 (m, 1H); 3.30-3.20 (m, overlapped, 1H); 3.01 (s, 3H); 2.74-2.58 (m, 1H); 2.19-2.04 (m, 1H); 1.57 (s, 3H); 1.46-1.35 (m, 2H); 0.95-0.79 (m, 2H).

MS (ESI, m/z): 429.0 [M+H⁺] for $C_{22}H_{24}N_2O_5S$; $t_R$=0.74 min.

Example 18

(R)—N-hydroxy-4-(5-(((1R,2R)-2-(hydroxymethyl) cyclopropyl)buta-1,3-diyn-1-yl)-1H-indol-1-yl)-2-methyl-2-(methylsulfonyl)butanamide Starting from the compound of Preparation M (0.136 g; 0.32 mmol) and the (1R,2R)-configured compound of Preparation P (0.095 g; 0.43 mmol), and proceeding in analogy to Example 17, steps 17.i to 17.iii (Sonogashira coupling: 37% yield; acetate cleavage: 89% yield; deprotection: 55% yield), the title compound was obtained, after purification by prep-HPLC (Method 2), as a brownish oil (0.027 g).

¹H NMR (d6-DMSO) δ: 9.27 (br. s, 1H); 7.76 (s, 1H); 7.52-7.45 (m, 2H); 7.28 (d, J=8.5 Hz, 1H); 6.48 (d, J=2.7 Hz, 1H); 4.67 (t, J=5.6 Hz, 1H); 4.38-4.24 (m, 1H); 4.08-3.94 (m, 1H); 3.46-3.34 (m, 1H); 3.30-3.20 (m, overlapped, 1H); 3.01 (s, 3H); 2.74-2.58 (m, 1H); 2.19-2.04 (m, 1H); 1.57 (s, 3H); 1.46-1.35 (m, 2H); 0.95-0.79 (m, 2H).

MS (ESI, m/z): 429.0 [M+H+] for $C_{22}H_{24}N_2O_5S$; $t_R$=0.74 min.

Example 19

(R)—N-hydroxy-4-(5-((4-((1S,2S)-2-(hydroxymethyl)cyclopropyl)phenyl)ethynyl)-1H-indazol-1-yl)-2-methyl-2-(methylsulfonyl)butanamide Starting from the compound of Preparation J (0.114 g; 0.27 mmol) and the (1S,2S)-configured compound of Preparation Q (0.085 g; 0.31 mmol), and proceeding successively in analogy to Reference Example 5, step RE5.i (76% yield) and Reference Example 1, step RE1.viii (29% yield), the title compound was obtained, after purification by prep-HPLC (Method 2), as a white solid (0.029 g).

¹H NMR (d6-DMSO) δ: 11.06 (s, 1H); 9.30 (s, 1H); 8.14 (s, 1H); 8.00 (s, 1H); 7.69 (m, 1H); 7.55 (m, 1H); 7.43 (d, J=8.1 Hz, 2H); 7.12 (d, J=8.2 Hz, 2H); 4.66 (t, J=5.6 Hz, 1H); 4.50-4.59 (m, 1H); 4.26-4.35 (m, 1H); 3.45-3.52 (m, 1H); 3.35 (overlapped m, 1H); 3.04 (s, 3H); 2.71-2.81 (m, 1H); 2.18-2.27 (m, 1H); 1.80-1.87 (m, 1H); 1.55 (s, 3H); 1.28-1.36 (m, 1H); 0.86-0.97 (m, 2H).

MS (ESI, m/z): 481.9 [M+H+] for $C_{25}H_{27}N_3O_5S$; $t_R$=0.75 min.

Example 20

(R)—N-hydroxy-4-(5-((4-((1R,2R)-2-(hydroxymethyl)cyclopropyl)phenyl)ethynyl)-1H-indazol-1-yl)-2-methyl-2-(methylsulfonyl)butanamide Starting from the compound of Preparation J (0.114 g; 0.27 mmol) and the (1R,2R)-configured compound of Preparation Q (0.085 g; 0.31 mmol), and proceeding successively in analogy to Reference Example 5, step RE5.i (90% yield) and Reference Example 1, step RE1.viii (5% yield), the title compound was obtained, after purification by prep-HPLC (Method 2), as a white solid (0.006 g).

¹H NMR (d6-DMSO) δ: 11.06 (s, 1H); 9.30 (s, 1H); 8.14 (s, 1H); 8.00 (s, 1H); 7.70 (m, 1H); 7.56 (dd, J=1.0, 8.7 Hz, 1H); 7.43 (d, J=8.2 Hz, 2H); 7.12 (d, J=8.3 Hz, 2H); 4.50-4.59 (m, 1H); 4.26-4.35 (m, 1H); 3.45-3.52 (m, 1H); 3.35 (overlapped m, 1H); 3.04 (s, 3H); 2.71-2.81 (m, 1H); 2.18-2.27 (m, 1H); 1.80-1.87 (m, 1H); 1.55 (s, 3H); 1.28-1.36 (m, 1H); 0.86-0.97 (m, 2H).

MS (ESI, m/z): 481.9 [M+H+] for $C_{25}H_{27}N_3O_5S$; $t_R$=0.75 min.

Example 21

(R)-4-(5-((4-((R)-1,2-dihydroxyethyl)phenyl)ethynyl)-1H-indazol-1-yl)-N-hydroxy-2-methyl-2-(methylsulfonyl)butanamide Starting from the compound of Preparation J (0.137 g; 0.32 mmol) and (R)-1-(4-iodophenyl)-1,2-ethanediol (0.1 g; 0.37 mmol; commercial), and proceeding successively in analogy to Reference Example 5, step RE5.i (76% yield) and Reference Example 1, step RE1.viii (44% yield), the title compound was obtained, after purification by prep-HPLC (Method 2), as a white solid (0.051 g).

¹H NMR (d6-DMSO) δ: 11.06 (s, 1H); 9.30 (s, 1H); 8.15 (s, 1H); 8.02 (s, 1H); 7.70 (d, J=8.7 Hz, 1H); 7.57 (d, J=8.6 Hz, 1H); 7.51 (m, 2H); 7.40 (d, J=7.7 Hz, 2H); 5.35 (m, 1H); 4.50-4.61 (m, 2H); 4.32 (m, 1H); 3.43-3.47 (m, 2H); 3.05 (s, 3H); 2.77 (m, 1H); 2.23 (m, 1H); 1.56 (s, 3H).

MS (ESI, m/z): 471.9 [M+H⁺] for $C_{23}H_{25}N_3O_6S$; $t_R$=0.62 min.

Example 22

(R)-4-(5-((4-((S)-1,2-dihydroxyethyl)phenyl)ethynyl)-1H-indazol-1-yl)-N-hydroxy-2-methyl-2-(methylsulfonyl)butanamide Starting from the compound of Preparation J (0.137 g; 0.32 mmol) and (S)-1-(4-iodophenyl)-1,2-ethanediol (0.1 g; 0.37 mmol; commercial), and proceeding successively in analogy to Reference Example 5, step RE5.i (64% yield) and Reference Example 1, step RE1.viii (60% yield), the title compound was obtained, after purification by prep-HPLC (Method 2), as a white solid (0.060 g).

¹H NMR (d6-DMSO) δ: 11.06 (s, 1H); 9.30 (s, 1H); 8.15 (s, 1H); 8.02 (s, 1H); 7.70 (d, J=8.7 Hz, 1H); 7.57 (d, J=8.6 Hz, 1H); 7.51 (m, 2H); 7.40 (d, J=7.7 Hz, 2H); 5.35 (m, 1H); 4.50-4.61 (m, 2H); 4.32 (m, 1H); 3.43-3.47 (m, 2H); 3.05 (s, 3H); 2.77 (m, 1H); 2.23 (m, 1H); 1.56 (s, 3H).

MS (ESI, m/z): 471.9 [M+H⁺] for $C_{23}H_{25}N_3O_6S$; $t_R$=0.62 min.

Example 23

(R)—N-hydroxy-4-(5-((4-((S)-1-hydroxyethyl)phenyl)ethynyl)-1H-indazol-1-yl)-2-methyl-2-(methylsulfonyl)butanamide Starting from the compound of Preparation J (0.157 g; 0.374 mmol) and (S)-1-(4-iodophenyl)ethan-1-ol (0.106 g; 0.427 mmol; commercial), and proceeding successively in analogy to Reference Example 5, step RE5.i (88% yield) and Reference Example 1, step RE1.viii (40% yield), the title compound was obtained, after purification by prep-HPLC (Method 2), as a yellow solid (0.069 g).

¹H NMR (d6-DMSO) δ: 10.90 (br s, 1H); 9.26 (br. s, 1H); 8.14 (s, 1H); 8.02 (s, 1H); 7.71 (d, J=8.6 Hz, 1H); 7.57 (d, J=8.6 Hz, 1H); 7.52 (d, J=7.4 Hz, 2H); 7.40 (d, J=7.5 Hz, 2H); 5.26 (m, 1H); 4.75 (m, 1H); 4.55 (m, 1H); 4.33 (m, 1H); 3.05 (s, 3H); 2.76 (m, 1H); 2.23 (m, 1H); 1.55 (s, 3H); 1.34 (d, J=6.1 Hz, 3H).

MS (ESI, m/z): 455.9 [M+H⁺] for $C_{23}H_{25}N_3O_5S$; $t_R$=0.72 min.

Example 24

(R)-4-(5-(5-amino-5-methylhexa-1,3-diyn-1-yl)-1H-indazol-1-yl)-N-hydroxy-2-methyl-2-(methylsulfonyl)butanamide Starting from the compound of Preparation J (0.145 g; 0.34 mmol) and the compound of Preparation R (0.082 g; 0.39 mmol), and proceeding successively in analogy to Reference Example 5, step RE5.i (67% yield) and Reference Example 1, step RE1.viii (3% yield), the title compound was obtained, after purification by prep-HPLC (Method 2), as a white solid (0.003 g).

¹H NMR (d6-DMSO) δ: 10.90 (br. s, 1H); 9.28 (br. s, 1H); 8.14 (s, 1H); 8.03 (s, 1H); 7.68 (d, J=8.6 Hz, 1H); 7.53 (d, J=8.6 Hz, 1H); 7.28 (br. s, 1H); 6.68 (br. s, 1H); 4.53 (m, 1H); 4.30 (m, 1H); 3.03 (s, 3H); 2.73 (m, 1H); 2.20 (m, 1H); 1.54 (s, 3H); 1.34 (s, 6H).
MS (ESI, m/z): 418.1 [M+H$^+$] for $C_{20}H_{24}N_4O_4S$; $t_R$=0.55 min.

Example 25

(R)—N-hydroxy-4-(5-((4-(1-(hydroxymethyl)cyclopropyl)phenyl)ethynyl)-1H-indol-1-yl)-2-methyl-2-(methylsulfonyl)butanamide Starting from the compound of Preparation L (0.189 g; 0.365 mmol) and the compound of Preparation S (0.092 g; 0.47 mmol), and proceeding in analogy to Reference Example 5, step RE5.i (100% yield) and Reference Example 1, step RE1.viii (53% yield), the title compound was obtained, after filtration and washing with water, as an off-white solid (0.096 g).
¹H NMR (d6-DMSO) δ: 11.08 (br. s, 1H); 9.30 (br. s, 1H); 7.78 (s, 1H); 7.54 (d, J=8.1 Hz, 1H); 7.48 (d, J=2.9 Hz, 1H); 7.44 (d, J=8.1 Hz, 2H); 7.33 (d, J=8.1 Hz, 3H); 6.50 (d, J=2.9 Hz, 1H); 4.73 (t, J=5.5 Hz, 1H); 4.29-4.38 (m, 1H); 3.99-4.07 (m, 1H); 3.56 (d, J=5.5 Hz, 2H); 3.04 (s, 3H); 2.63-2.72 (m, 1H); 2.11-2.19 (m, 1H); 1.59 (s, 3H); 0.86-0.90 (m, 2H); 0.76-0.80 (m, 2H).
MS (ESI, m/z): 483.1 [M+H$^+$] for $C_{26}H_{28}N_2O_5S$; $t_R$=0.81 min.

Example 26

(R)—N-hydroxy-4-(5-(((1S,2S)-2-(hydroxymethyl)cyclopropyl)buta-1,3-diyn-1-yl)-1H-indazol-1-yl)-2-methyl-2-(methylsulfonyl)butanamide Starting from the compound of Preparation J (0.120 g; 0.28 mmol) and the (1S,2S)-configured compound of Preparation P (0.071 g; 0.32 mmol), and proceeding in analogy to Example 17, steps 17.i to 17.iii (Sonogashira coupling: 67% yield; acetate cleavage: 68% yield; deprotection: 12% yield), the title compound was obtained, after purification by prep-HPLC (Method 2), as a brownish oil (0.007 g).
¹H NMR (d6-DMSO) δ: 11.0 (s, 1H); 9.26 (s, 1H); 8.13 (s, 1H); 8.02 (s, 1H); 7.67 (d, J=8.7 Hz, 1H); 7.51 (d, J=8.7 Hz, 1H); 4.71 (t, J=5.6 Hz, 1H); 4.48-4.58 (m, 1H); 4.25-4.35 (m, 1H); 3.39-3.46 (m, 1H); 3.22-3.30 (m, 1H); 3.03 (s, 3H); 2.68-2.78 (m, 1H); 2.15-2.25 (m, 1H); 1.53 (s, 3H); 1.39-1.47 (m, 2H); 0.82-0.96 (m, 2H).
MS (ESI, m/z): 429.9 [M+H$^+$] for $C_{21}H_{23}N_3O_5S$; $t_R$=0.70 min.

Example 27

(R)—N-hydroxy-4-(5-((4-(2-hydroxyethoxy)phenyl)ethynyl)-1H-indazol-1-yl)-2-methyl-2-(methylsulfonyl)butanamide Starting from the compound of Preparation J (0.133 g; 0.31 mmol) and 2-(4-iodophenoxy)ethanol (0.096 g; 0.36 mmol; commercial), and proceeding successively in analogy to Reference Example 5, step RE5.i (69% yield) and Reference Example 1, step RE1.viii (82% yield), the title compound was obtained, after purification by prep-HPLC (Method 2), as a white solid (0.085 g).

¹H NMR (d6-DMSO) δ: 11.06 (s, 1H); 9.27 (s, 1H); 8.13 (s, 1H); 7.99 (s, 1H); 7.69 (d, J=8.7 Hz, 1H); 7.55 (d, J=10.1 Hz, 1H); 7.50 (d, J=8.8 Hz, 2H); 7.00 (d, J=8.8 Hz, 2H); 4.90 (t, J=5.6 Hz, 1H); 4.50-4.58 (m, 1H); 4.23-4.36 (m, 1H); 4.03 (t, J=4.9 Hz, 2H); 3.71-3.75 (m, 2H); 3.04 (s, 3H); 2.71-2.81 (m, 1H); 2.17-2.28 (m, 1H); 1.55 (s, 3H).
MS (ESI, m/z): 471.9 [M+H$^+$] for $C_{23}H_{25}N_3O_6S$; $t_R$=0.70 min.

Example 28

(R)—N-hydroxy-4-(5-((4-(2-hydroxyacetamido)phenyl)ethynyl)-1H-indazol-1-yl)-2-methyl-2-(methylsulfonyl)butanamide Starting from the compound of Preparation J (0.130 g; 0.31 mmol) and 2-hydroxy-N-(4-iodophenyl)acetamide (0.096 g; 0.36 mmol; commercial), and proceeding successively in analogy to Reference Example 5, step RE5.i (42% yield) and Reference Example 1, step RE1.viii (82% yield), the title compound was obtained, after purification by prep-HPLC (Method 2), as a white solid (0.085 g).
¹H NMR (d6-DMSO) δ: 11.00 (s, 1H); 9.88 (s, 1H); 9.29 (s, 1H); 8.14 (s, 1H); 8.00 (s, 1H); 7.79 (d, J=8.7 Hz, 2H); 7.70 (d, J=8.8 Hz, 1H); 7.56 (d, J=8.8 Hz, 1H); 7.51 (d, J=8.7 Hz, 2H); 5.70 (t, J=6.1 Hz, 1H); 4.50-4.58 (m, 1H); 4.27-4.35 (m, 1H); 4.02 (d, J=6.0 Hz, 2H); 3.04 (s, 3H); 2.72-2.81 (m, 1H); 2.18-2.26 (m, 1H); 1.56 (s, 3H).
MS (ESI, m/z): 484.8 [M+H$^+$] for $C_{23}H_{24}N_4O_6S$; $t_R$=0.66 min.

Example 29

(R)—N-hydroxy-4-(5-((4-(2-hydroxypropan-2-yl)phenyl)ethynyl)-1H-indol-1-yl)-2-methyl-2-(methylsulfonyl)butanamide Starting from the compound of Preparation L (0.180 g, 0.43 mmol) and 2-(4-ethynylphenyl)propan-2-ol (0.147 g; 0.43 mmol; commercial), and proceeding in analogy to Reference Example 5, step RE5.i (45% yield) and Reference Example 1, step RE1.viii (47% yield), the title compound was obtained, after purification by prep-HPLC (Method 2), as a white solid (0.043 g).
¹H NMR (d6-DMSO) δ: 11.08 (s, 1H); 9.29 (s, 1H); 7.79 (s, 1H); 7.45-7.56 (m, 6H); 7.33 (dd, J=1.0, 8.4 Hz, 1H); 6.50 (d, J=3.0 Hz, 1H); 5.10 (s, 1H); 4.30-4.38 (m, 1H); 4.00-4.08 (m, 1H); 3.04 (s, 3H); 2.65-2.72 (m, 1H); 2.10-2.19 (m, 1H); 1.59 (s, 3H); 1.44 (s, 6H).
MS (ESI, m/z): 469.0 [M+H$^+$] for $C_{25}H_{28}N_2O_5S$; $t_R$=0.79 min.

Example 30

(R)-4-(4-fluoro-5-((4-(3-hydroxyoxetan-3-yl)phenyl)ethynyl)-1H-indazol-1-yl)-N-hydroxy-2-methyl-2-(methylsulfonyl)butanamide Starting from the compound of Preparation T (0.288 g; 0.533 mmol) and intermediate RE13.i (0.105 g; 0.6 mmol), and proceeding in analogy to Reference Example 5, step RE5.i (51% yield) and Reference Example 1, step RE1.viii (33% yield), the title compound was obtained, after purification by prep-HPLC (Method 2), as a white solid (0.046 g).
¹H NMR (d6-DMSO) δ: 11.04 (s, 1H); 9.27 (s, 1H); 8.31 (s, 1H); 7.66-7.69 (m, 2H); 7.56-7.63 (m, 4H); 6.49 (s, 1H); 4.79 (d, J=6.5 Hz, 2H); 4.68 (d, J=6.5 Hz, 2H); 4.54-4.61 (m, 1H); 4.29-4.37 (m, 1H); 3.04 (s, 3H); 2.74-2.81 (m, 1H); 2.19-2.26 (m, 1H); 1.56 (s, 3H).

MS (ESI, m/z): 501.9 [M+H⁺] for $C_{24}H_{24}N_3O_6FS$; $t_R$=0.71 min.

Example 31

(R)-4-(4-fluoro-5-(((1S,2S)-2-(hydroxymethyl)cyclopropyl)buta-1,3-diyn-1-yl)-1H-indazol-1-yl)-N-hydroxy-2-methyl-2-(methylsulfonyl)butanamide CuCl (0.004 g, 0.042 mmol) was added to a solution of nBuNH₂ (30% in water, 0.46 mL) at rt. NH₂OH.HCl (0.039 g; 0.57 mmol) was added. The compound of Preparation T (0.201 g; 0.46 mmol) was added and the solution was immediately ice-chilled. The (1S,2S)-configured compound of Preparation P (0.087 g, 0.40 mmol) was added in one portion. The reaction proceeded at rt for 1.75 h. The reaction mixture was diluted with water (7 mL) and extracted four times with EA (4×10 mL). The combined org. layers were dried over MgSO₄, filtered and evaporated under reduced pressure to afford a crude mixture. The latter was converted into the title compound by proceeding in analogy to Example 17, steps 17.ii to 17.iii (acetate cleavage and deprotection). After purification by prep-HPLC (Method 2), a yellowish foam (0.019 g) was obtained.

¹H NMR (d6-DMSO) δ: 11.05 (br. s, 1H); 9.26 (br. s, 1H); 8.29 (s, 1H); 7.51-7.55 (m, 2H); 4.71 (t, J=5.4 Hz, 1H); 4.51-4.59 (m, 1H); 4.27-4.35 (m, 1H); 3.39-3.46 (m, 1H); 3.23-3.28 (m, 1H); 3.02 (s, 3H); 2.70-2.78 (m, 1H); 2.15-2.23 (m, 1H); 1.54 (s, 3H); 1.41-1.48 (m, 2H); 0.92-0.97 (m, 1H); 0.85-0.90 (m, 1H).

MS (ESI, m/z): 447.95 [M+H⁺] for $C_{21}H_{22}N_3O_5FS$; $t_R$=0.72 min.

Example 32

(R)—N-hydroxy-4-(5-((3-hydroxythietan-3-yl)buta-1,3-diyn-1-yl)-1H-indol-1-yl)-2-methyl-2-(methylsulfonyl)butanamide Starting from the compound of Preparation M (0.18 g; 0.43 mmol) and the compound of Preparation N (0.135 g; 0.55 mmol), and proceeding successively in analogy to Reference Example 5, step RE5.i (48% yield) and Reference Example 1, step RE1.viii (28% yield), the title compound was obtained, after purification by prep-HPLC (Method 2), as a white solid (0.025 g).

¹H NMR (d6-DMSO) δ: 11.07 (s, 1H); 9.30 (s, 1H); 7.86 (s, 1H); 7.55 (d, J=8.6 Hz, 1H); 7.52 (d, J=3.0 Hz, 1H); 7.37 (d, J=8.6 Hz, 1H); 6.81 (s, 1H); 6.52 (d, J=3.0 Hz, 1H); 4.30-4.40 (m, 1H); 3.99-4.08 (m, 1H); 3.51 (d, J=9.6 Hz, 2H); 3.38 (d, J=9.6 Hz, 2H); 3.03 (s, 3H); 2.62-2.70 (m, 1H); 2.07-2.16 (m, 1H); 1.58 (s, 3H).

MS (ESI, m/z): 468.98 [M+H⁺] for $C_{25}H_{28}N_2O_5S$; $t_R$=0.79 min.

Example 33

(R)—N-hydroxy-4-(5-((4-((1S,2S)-2-(hydroxymethyl)cyclopropyl)phenyl)ethynyl)-1H-indol-1-yl)-2-methyl-2-(methylsulfonyl)butanamide Starting from the compound of Preparation M (0.105 g; 0.25 mmol) and the (1R,2R)-configured compound of Preparation Q (0.090 g; 0.32 mmol), and proceeding successively in analogy to Reference Example 5, step RE5.i (87% yield) and Reference Example 1, step RE1.viii (3% yield), the title compound was obtained, after purification by prep-HPLC (Method 2), as a white solid (0.004 g).

¹H NMR (d6-DMSO) δ: 11.09 (s, 1H); 9.33 (s, 1H); 7.78 (s, 1H); 7.53 (d, J=8.2 Hz, 1H); 7.48 (s, 1H); 7.41 (d, J=7.4 Hz, 2H); 7.33 (d, J=8.2 Hz, 1H); 7.11 (d, J=7.4 Hz, 2H); 6.50 (s, 1H); 4.65 (br. s, 1H); 4.29-4.39 (m, 1H); 3.98-4.08 (m, 1H); 3.45-3.54 (m, 1H); 3.18 (d, J=3.6 Hz, 1H); 3.04 (s, 3H); 2.63-2.72 (m, 1H); 2.10-2.20 (m, 1H); 1.83 (br. s, 1H); 1.60 (s, 3H); 1.32 (br. s, 1H); 0.86-0.98 (m, 2H).

MS (ESI, m/z): 480.9 [M+H⁺] for $C_{26}H_{28}N_2O_5S$; $t_R$=0.79 min.

Example 34

(R)—N-hydroxy-4-(5-((1-(hydroxymethyl)cyclopropyl)buta-1,3-diyn-1-yl)-1H-indazol-1-yl)-2-methyl-2-(methylsulfonyl)butanamide 34.i. (2R)-4-(5-((1-(((tert-butyldiphenylsilyl)oxy)methyl)cyclopropyl)buta-1,3-diyn-1-yl)-1H-indazol-1-yl)-2-methyl-2-(methylsulfonyl)-N-((tetrahydro-2H-pyran-2-yl)oxy)butanamide Starting from the compound of Preparation J (0.150 g; 0.35 mmol) and the compound of Preparation U (0.170 g; 0.40 mmol), and proceeding in analogy to Reference Example 5, step RE5.i, the title compound was obtained, after purification by CC (DCM-MeOH gradient), as a yellowish oil (0.11 g; 41% yield).

MS (ESI, m/z): 751.9 [M+H⁺] for $C_{42}H_{49}N_3O_6SSi$; $t_R$=1.14 min.

34.ii. (R)—N-hydroxy-4-(5-((1-(hydroxymethyl)cyclopropyl)buta-1, 3-diyn-1-yl)-1H-indazol-1-yl)-2-methyl-2-(methylsulfonyl)butanamide To a solution of the intermediate 34.i (0.111 g; 0.147 mmol) in EtOH (4 mL) was added (±)-camphor-10-sulfonic acid (0.034 g; 0.147 mmol). The reaction mixture was stirred at rt for 4 h. The reaction mixture was concentrated to dryness and the residue was taken up in THF (2 mL). A solution of TBAF (1M in THF; 0.9 mL) was added. The mixture was stirred at rt overnight. The crude mixture was purified by prep-HPLC (Method 1) to afford the title compound as a white solid (0.014 g).

¹H NMR (d6-DMSO) δ: 11.04 (s, 1H); 9.27 (s, 1H); 8.14 (d, J=0.8 Hz, 1H); 8.03 (dd, J=0.8, 1.4 Hz, 1H); 7.67 (d, J=8.8 Hz, 1H); 7.52 (dd, J=1.5, 8.7 Hz, 1H); 5.03 (t, J=6.1 Hz, 1H); 4.49-4.57 (m, 1H); 4.26-4.35 (m, 1H); 3.40 (d, J=6.1 Hz, 2H); 3.03 (s, 3H); 2.69-2.79 (m, 1H); 2.15-2.24 (m, 1H); 1.54 (s, 3H); 0.91-0.97 (m, 2H); 0.84-0.90 (m, 2H).

MS (ESI, m/z): 430.0 [M+H⁺] for $C_{21}H_{23}N_3O_5S$; $t_R$=0.70 min.

Example 35

(R)—N-hydroxy-4-(5-((4-((S)-1-hydroxyethyl)phenyl)ethynyl)-1H-indol-1-yl)-2-methyl-2-(methylsulfonyl)butanamide Starting from the compound of Preparation M (0.120 g; 0.287 mmol) and (S)-1-(4-iodophenyl)ethan-1-ol (0.071 g; 0.287 mmol; commercial), and proceeding successively in analogy to Reference Example 5, step RE5.i (27% yield) and Reference Example 1, step RE1.viii (33% yield), the title compound was obtained, after purification by prep-HPLC (Method 2), as a white solid (0.011 g).

$^1$H NMR (d6-DMSO) δ: 11.07 (s, 1H); 9.30 (s, 1H); 7.86 (s, 1H); 7.55 (d, J=8.6 Hz, 1H); 7.52 (d, J=3.0 Hz, 1H); 7.37 (d, J=8.6 Hz, 1H); 6.81 (s, 1H); 6.52 (d, J=3.0 Hz, 1H); 4.30-4.40 (m, 1H); 3.99-4.08 (m, 1H); 3.51 (d, J=9.6 Hz, 2H); 3.38 (d, J=9.6 Hz, 2H); 3.03 (s, 3H); 2.62-2.70 (m, 1H); 2.07-2.16 (m, 1H); 1.58 (s, 3H).

MS (ESI, m/z): 455.0 [M+H$^+$] for $C_{24}H_{26}N_2O_5S$; $t_R$=0.76 min.

Example 36

(R)-4-(4-fluoro-5-((4-(2-hydroxyethyl)phenyl)ethynyl)-1H-indazol-1-yl)-N-hydroxy-2-methyl-2-(methylsulfonyl)butanamide Starting from the compound of Preparation T (0.154 g; 0.352 mmol) and 2-(4-iodophenyl)ethanol (0.093 g; 0.375 mmol; commercial), and proceeding in analogy to Reference Example 5, step RE5.i (94% yield) and Reference Example 1, step RE1.viii (8% yield), the title compound was obtained, after purification by prep-HPLC (Method 1), as a yellowish solid (0.013 g).

$^1$H NMR (d6-DMSO) δ: 11.05 (br. s, 1H); 9.26 (br. s, 1H); 8.30 (s, 1H); 7.54-7.60 (m, 2H); 7.45-7.52 (m, 2H); 7.26-7.33 (m, 2H); 4.68 (br. s, 1H); 4.52-4.61 (m, 1H); 4.28-4.37 (m, 1H); 3.58-3.66 (m, 2H); 3.04 (s, 3H); 2.17-2.82 (overlapped m, 4H); 1.55 (s, 3H).

MS (ESI, m/z): 474.0 [M+H$^+$] for $C_{23}H_{24}N_3O_5FS$; $t_R$=0.74 min.

Example 37

(R)-4-(4-fluoro-5-((4-((R)-1-hydroxyethyl)phenyl)ethynyl)-1H-indazol-1-yl)-N-hydroxy-2-methyl-2-(methylsulfonyl)butanamide Starting from the compound of Preparation T (0.154 g; 0.352 mmol) and (R)-1-(4-iodophenyl)ethan-1-ol (0.106 g; 0.427 mmol; commercial), and proceeding in analogy to Reference Example 5, step RE5.i (65% yield) and Reference Example 1, step RE1.viii (44% yield), the title compound was obtained, after purification by CC (DCM-MeOH gradient), as an off-white foam (0.048 g).

$^1$H NMR (d6-DMSO) δ: 11.04 (s, 1H); 9.27 (s, 1H); 8.30 (s, 1H); 7.55-7.60 (m, 2H); 7.51-7.54 (m, 2H); 7.39-7.42 (m, 2H); 5.27 (d, J=4.3 Hz, 1H); 4.72-4.79 (m, 1H); 4.53-4.61 (m, 1H); 4.29-4.37 (m, 1H); 3.04 (s, 3H); 2.73-2.81 (m, 1H); 2.17-2.26 (m, 1H); 1.56 (s, 3H); 1.33 (d, J=6.5 Hz, 3H).

MS (ESI, m/z): 474.0 [M+H$^+$] for $C_{23}H_{24}N_3O_5FS$; $t_R$=0.74 min.

Example 38

(R)-4-(4-fluoro-5-((3-hydroxyoxetan-3-yl)buta-1,3-diyn-1-yl)-1H-indazol-1-yl)-N-hydroxy-2-methyl-2-(methylsulfonyl)butanamide Starting from the compound of Preparation T (0.118 g; 0.27 mmol) and the compound of Preparation K (0.093 g; 0.375 mmol), and proceeding in analogy to Example 31 (23% yield) and Reference Example 1, step RE1.viii (28% yield), the title compound was obtained, after purification by prep-HPLC (Method 2), as an off-white solid (0.013 g).

$^1$H NMR (d6-DMSO) δ: 11.07 (br. s, 1H); 9.28 (br. s, 1H); 8.33 (s, 1H); 7.54-7.63 (m, 2H); 6.81 (s, 1H); 4.74 (d, J=6.6 Hz, 2H); 4.53-4.61 (overlapped m, 1H); 4.56 (d, J=6.6 Hz, 2H); 4.29-4.36 (m, 1H); 3.02 (s, 3H); 2.70-2.79 (m, 1H); 2.16-2.25 (m, 1H); 1.54 (s, 3H).

MS (ESI, m/z): 450.9 [M+H$^+$] for $C_{20}H_{20}N_3O_6FS$; $t_R$=0.67 min.

Example 39

(R)-4-(4-fluoro-5-((1-(hydroxymethyl)cyclopropyl)buta-1,3-diyn-1-yl)-1H-indazol-1-yl)-N-hydroxy-2-methyl-2-(methylsulfonyl)butanamide Starting from the compound of Preparation T (0.073 g; 0.167 mmol) and the compound of Preparation U (0.079 g; 0.19 mmol), and proceeding in analogy to Example 31 (23% yield) and Example 34, step 34.ii (24% yield), the title compound was obtained, after purification by prep-HPLC (Method 1), as an off-white solid (0.012 g).

$^1$H NMR (d6-DMSO) δ: 11.03 (br. s, 1H); 9.25 (br. s, 1H); 8.30 (s, 1H); 7.51-7.56 (m, 2H); 5.05 (t, J=6.1 Hz, 1H); 4.51-4.59 (m, 1H); 4.27-4.35 (m, 1H); 3.40 (d, J=6.1 Hz, 2H); 3.02 (s, 3H); 2.70-2.78 (m, 1H); 2.15-2.23 (m, 1H); 1.54 (s, 3H); 0.94-0.97 (m, 2H); 0.87-0.91 (m, 2H).

MS (ESI, m/z): 448.0 [M+H+] for $C_{21}H_{22}N_3O_5FS$; $t_R$=0.72 min.

Example 40

(R)-4-(4-fluoro-5-((4-(3-(hydroxymethyl)oxetan-3-yl)phenyl)ethynyl)-1H-indazol-1-yl)-N-hydroxy-2-methyl-2-(methylsulfonyl)butanamide Starting from the compound of Preparation T (0.11 g, 0.25 mmol) and the compound of Preparation V (0.074 g; 0.254 mmol), and proceeding in analogy to Reference Example 5, step RE5.i (76% yield) and Reference Example 1, step RE1.viii (16% yield), the title compound was obtained, after purification by prep-HPLC (Method 1) as a yellowish foam (0.016 g).

$^1$H NMR (d6-DMSO) δ: 11.05 (br. s, 1H); 9.27 (br. s, 1H); 8.30 (s, 1H); 7.53-7.61 (m, 4H); 7.22 (d, J=8.1 Hz, 2H); 5.15-5.19 (m, 1H); 4.70-4.74 (m, 4H); 4.53-4.61 (m, 1H); 4.29-4.37 (m, 1H); 3.73 (d, J=4.5 Hz, 2H); 3.04 (s, 3H); 2.74-2.81 (m, 1H); 2.19-2.26 (m, 1H); 1.56 (s, 3H).

MS (ESI, m/z): 517.0 [M+H+] for $C_{25}H_{26}N_3O_6FS$; $t_R$=0.71 min.

Example 41

(R)-4-(6-fluoro-5-(((1R*,2R*)-2-(hydroxymethyl)cyclopropyl)buta-1,3-diyn-1-yl)-1H-indol-1-yl)-N-hydroxy-2-methyl-2-(methylsulfonyl)butanamide 41.i. (2R)-4-(5-(((1R*,2R*)-2-(((tert-butyldimethylsilyl)oxy)methyl)cyclopropyl) buta-1, 3-diyn-1-yl)-6-fluoro-1H-indol-1-yl)-2-methyl-2-(methylsulfonyl)-N-((tetrahydro-2H-pyran-2-yl)oxy)butanamide Starting from the compound of Preparation E (0.093 g, 0.2 mmol) and the compound of Preparation G (0.088 g, 0.44 mmol), and proceeding in analogy to Reference Example 5, step RE5.i, the title compound was obtained, after purification by CC (Hept-EA), as a brown gum (0.061 g; 44% yield).

MS (ESI, m/z): 645.01 [M+H+] for $C_{33}H_{45}N_2O_6FSSi$; $t_R$=1.13 min.

41.ii. (2R)-4-(6-fluoro-5-(((1R*,2R*)-2-(hydroxymethyl)cyclopropyl)buta-1, 3-diyn-1-yl)-1H-indol-1-yl)-2-methyl-2-(methylsulfonyl)-N-((tetrahydro-2H-pyran-2-yl)oxy)butanamide To a solution of intermediate 41.i (0.061 g; 0.101 mmol) in THF (0.5 mL) was added 1M TBAF in THF (0.2 mL; 0.2 mmol). The reaction was stirred at rt for 1 h. The solvent was removed under reduced pressure and the residue was purified by CC (DCM/MeOH) to afford the title compound as an orange brown solid (0.04 g, 74% yield).
MS (ESI, m/z): 531.01 [M+H$^+$] for $C_{27}H_{31}N_2O_6FS$; $t_R$=0.88 min.

41.iii. (R)-4-(6-fluoro-5-(((1R*,2R*)-2-(hydroxymethyl)cyclopropyl)buta-1, 3-diyn-1-yl)-1H-indol-1-yl)-N-hydroxy-2-methyl-2-(methylsulfonyl)butanamide Starting from intermediate 41.ii (0.04 g; 0.074 mmol) and proceeding in analogy to Reference Example 1, step RE1.viiii, the title compound was obtained, after purification by prep-HPLC (Method 2), as an off-white foam (0.01 g; 32% yield).
$^1$H NMR (d6-DMSO) δ: 9.26 (br. s, 1H); 7.79 (d, J=7.1 Hz, 1H); 7.51-7.43 (m, 2H); 6.48 (d, J=3.2 Hz, 1H); 4.68 (t, J=5.6 Hz, 1H); 4.34-4.19 (m, 1H); 4.01-3.88 (m, 1H); 3.51-3.37 (overlapped, m, 1H); 3.30-3.20 (overlapped, m, 1H); 3.01 (s, 3H); 2.71-2.50 (overlapped, m, 1H); 2.21-2.01 (m, 1H); 1.56 (s, 3H); 1.43 (m, 2H); 0.91 (m, 2H).
MS (ESI, m/z): 446.99 [M+H+] for $C_{22}H_{23}N_2O_5FS$; $t_R$=0.76 min.

Example 42

(R)—N-hydroxy-4-(5-(((1R,2R)-2-(hydroxymethyl)cyclopropyl)buta-1,3-diyn-1-yl)-1H-indazol-1-yl)-2-methyl-2-(methylsulfonyl)butanamide Starting from the compound of Preparation J (0.120 g; 0.28 mmol) and the (1R,2R)-configured compound of Preparation P (0.071 g; 0.32 mmol), and proceeding in analogy to Example 31 (95% yield) and Example 17, steps 17.ii and 17.iii (acetate cleavage: 95% yield; deprotection: 56% yield), the title compound was obtained, after purification by prep-HPLC (Method 2), as a brown solid (0.064 g).
$^1$H NMR (d6-DMSO) δ: 11.0 (s, 1H); 9.26 (s, 1H); 8.13 (s, 1H); 8.02 (s, 1H); 7.67 (d, J=8.7 Hz, 1H); 7.51 (d, J=8.7 Hz, 1H); 4.71 (t, J=5.6 Hz, 1H); 4.48-4.58 (m, 1H); 4.25-4.35 (m, 1H); 3.39-3.46 (m, 1H); 3.22-3.30 (m, 1H); 3.03 (s, 3H); 2.68-2.78 (m, 1H); 2.15-2.25 (m, 1H); 1.53 (s, 3H); 1.39-1.47 (m, 2H); 0.82-0.96 (m, 2H).
MS (ESI, m/z): 430.0 [M+H+] for $C_{21}H_{23}N_3O_5S$; $t_R$=0.58 min.

Example 43

(R)-4-(5-((2-fluoro-4-(hydroxymethyl)phenyl)ethynyl)-1H-indol-1-yl)-N-hydroxy-2-methyl-2-(methylsulfonyl)butanamide Starting from the compound of Preparation M (0.120 g; 0.287 mmol) and (3-fluoro-4-iodophenyl)methanol (0.073 g; 0.287 mmol; commercial), and proceeding successively in analogy to Reference Example 5, step RE5.i (31% yield) and Reference Example 1, step RE1.viii (42% yield), the title compound was obtained, after purification by prep-HPLC (Method 2), as a yellow solid (0.017 g).
$^1$H NMR (d6-DMSO) δ: 11.08 (br. s, 1H); 9.32 (br. s, 1H); 7.81 (d, J=0.9 Hz, 1H); 7.54-7.60 (m, 2H); 7.50 (d, J=3.1 Hz, 1H); 7.34 (dd, J=1.3, 8.5 Hz, 1H); 7.25 (d, J=10.7 Hz, 1H); 7.20 (d, J=8.0 Hz, 1H); 6.52 (d, J=3.1 Hz, 1H); 5.41 (t, J=5.8 Hz, 1H); 4.55 (d, J=5.8 Hz, 2H); 4.31-4.39 (m, 1H); 4.00-4.08 (m, 1H); 3.04 (s, 3H); 2.65-2.74 (m, 1H); 2.11-2.19 (m, 1H); 1.59 (s, 3H).
MS (ESI, m/z): 459.0 [M+H$^+$] for $C_{23}H_{23}N_2O_5FS$; $t_R$=0.76 min.

Example 44

(R)-4-(5-((4-((R)-1,2-dihydroxyethyl)phenyl)ethynyl)-1H-indol-1-yl)-N-hydroxy-2-methyl-2-(methylsulfonyl)butanamide Starting from the compound of Preparation M (0.120 g; 0.287 mmol) and (R)-1-(4-iodophenyl)ethane-1,2-diol (0.076 g; 0.287 mmol; commercial), and proceeding successively in analogy to Reference Example 5, step RE5.i (27% yield) and Reference Example 1, step RE1.viii (44% yield), the title compound was obtained, after purification by prep-HPLC (Method 2), as a yellow solid (0.016 g).
$^1$H NMR (d6-DMSO) δ: 11.07 (m, 1H); 9.32 (m, 1H); 7.79 (s, 1H); 7.54 (d, J=8.5 Hz, 1H); 7.48 (m, 3H); 7.38 (d, J=8.1 Hz, 2H); 7.33 (d, J=8.6 Hz, 1H); 6.51 (d, J=2.9 Hz, 1H); 5.33 (d, J=4.2 Hz, 1H); 4.76 (t, J=5.6 Hz, 1H); 4.56 (m, 1H); 4.34 (m, 1H); 4.03 (m, 1H); 3.44 (d, J=3.6 Hz, 3H); 3.04 (s, 3H); 2.69 (m, 1H); 2.15 (m, 1H); 1.59 (s, 3H).
MS (ESI, m/z): 470.1 [M+H+] for $C_{24}H_{26}N_2O_6S$; $t_R$=0.67 min.

Example 45

(R)—N-hydroxy-4-(5-((4-(2-hydroxyethyl)phenyl)ethynyl)-1H-indol-1-yl)-2-methyl-2-(methylsulfonyl)butanamide Starting from the compound of Preparation M (0.120 g; 0.287 mmol) and 2-(4-iodophenyl)ethanol (0.071 g; 0.287 mmol; commercial), and proceeding successively in analogy to Reference Example 5, step RE5.i (72% yield) and Reference Example 1, step RE1.viii (42% yield), the title compound was obtained, after purification by prep-HPLC (Method 2), as a grey solid (0.04 g).
$^1$H NMR (d6-DMSO) δ: 11.06 (br. s, 1H); 9.31 (br. s, 1H); 7.78 (d, J=0.7 Hz, 1H); 7.53 (d, J=8.5 Hz, 1H); 7.48 (d, J=3.1 Hz, 1H); 7.45 (d, J=8.0 Hz, 2H); 7.33 (dd, J=1.3, 8.5 Hz, 1H); 7.27 (d, J=8.0 Hz, 2H); 6.50 (d, J=3.1 Hz, 1H); 4.68 (t, J=5.2 Hz, 1H); 4.30-4.38 (m, 1H); 4.00-4.07 (m, 1H); 3.60-3.65 (m, 2H); 3.04 (s, 3H); 2.76 (t, J=6.9 Hz, 2H); 2.65-2.72 (m, 2H); 2.10-2.20 (m, 1H); 1.59 (s, 3H).
MS (ESI, m/z): 455.0 [M+H+] for $C_{24}H_{26}N_2O_5S$; $t_R$=0.76 min.

Example 46

(R)-4-(6-fluoro-5-(((1S,2S)-2-(hydroxymethyl)cyclopropyl)buta-1,3-diyn-1-yl)-1H-indazol-1-yl)-N-hydroxy-2-methyl-2-(methylsulfonyl)butanamide Starting from the compound of Preparation W (0.110 g; 0.25 mmol) and the (1S,2S)-configured compound of Preparation P (0.061 g; 0.28 mmol), and proceeding successively in analogy to Example 31 and Example 17, steps 17.ii and 17.iii, the title compound was obtained, after purification by prep-HPLC (Method 2), as a beige foam (0.024 g).

$^1$H NMR (d6-DMSO) δ: 11.03 (br. s, 1H); 9.26 (br. s, 1H); 8.14 (s, 1H); 8.09 (d, J=6.7 Hz, 1H); 7.66 (d, J=10.0 Hz, 1H); 4.68-4.73 (m, 1H); 4.44-4.52 (m, 1H); 4.20-4.27 (m, 1H); 3.40-3.45 (m, 1H); 3.23-3.36 (overlapped m, 1H); 3.02 (s, 3H); 2.68-2.76 (m, 1H); 2.14-2.22 (m, 1H); 1.53 (s, 3H); 1.42-1.49 (m, 2H); 0.92-0.97 (m, 1H); 0.85-0.90 (m, 1H).

MS (ESI, m/z): 449.0 [M+H+] for $C_{21}H_{22}N_3O_5FS$; $t_R$=0.71 min.

Example 47

(R)-4-(6-fluoro-5-((4-(2-hydroxyethyl)phenyl)ethynyl)-1H-indazol-1-yl)-N-hydroxy-2-methyl-2-(methylsulfonyl)butanamide Starting from the compound of Preparation W (0.097 g; 0.222 mmol) and 2-(4-iodophenyl)ethanol (0.058 g; 0.233 mmol; commercial), and proceeding successively in analogy to Reference Example 5, step RE5.i (51% yield) and Reference Example 1, step RE1.iii (10% yield), the title compound was obtained, after purification by prep-HPLC (Method 1), as a beige solid (0.006 g).

$^1$H NMR (d6-DMSO) δ: 11.07 (br. s, 1H); 9.26 (br. s, 1H); 8.15 (s, 1H); 8.09 (d, J=6.8 Hz, 1H); 7.69 (d, J=10.0 Hz, 1H); 7.48 (d, J=8.1 Hz, 2H); 7.29 (d, J=8.1 Hz, 2H); 4.68 (t, J=5.1 Hz, 1H); 4.47-4.54 (m, 1H); 4.22-4.29 (m, 1H); 3.60-3.65 (m, 2H); 3.04 (s, 3H); 2.76 (t, J=6.8 Hz, 2H); 2.71-2.78 (overlapped m, 1H); 2.16-2.25 (m, 1H); 1.55 (s, 3H).

MS (ESI, m/z): 473.95 [M+H$^+$] for $C_{23}H_{24}N_3O_5FS$; $t_R$=0.73 min.

Example 48

(R)-(1-(4-((1-(4-(hydroxyamino)-3-methyl-3-(methylsulfonyl)-4-oxobutyl)-1H-indazol-5-yl)ethynyl)phenyl)cyclopropyl)methyl dihydrogen phosphate 48.i. (R)-di-tert-butyl ((1-(4-((1-(3-methyl-3-(methylsulfonyl)-4-oxo-4-((((RS)-tetrahydro-2H-pyran-2-yl)oxy)amino)butyl)-1H-indazol-5-yl)ethynyl)phenyl)cyclopropyl)methyl) phosphate Starting from the compound of Preparation I (0.225 g; 0.432 mmol) and the compound of Preparation AA (0.173 g; 0.475 mmol) and proceeding in analogy to Reference Example 5, step RE5.i (32% yield), the title compound was obtained, after purification by CC (DCM-MeOH), as a yellow gum (0.104 g).

MS (ESI, m/z): [M+H$^+$] for $C_{38}H_{52}N_3O_9PS$; $t_R$=1.01 min.

48.ii. (R)-(1-(4-((1-(4-(hydroxyamino)-3-methyl-3-(methylsulfonyl)-4-oxobutyl)-1H-indazol-5-yl)ethynyl)phenyl)cyclopropyl)methyl dihydrogen phosphate A solution of intermediate 48.i (0.1 g; 0.077 mmol) in DCM (3.4 mL) was treated with TFA (1.56 mL; 20.2 mmol) and stirred at rt for 15 min. The mixture was concentrated to dryness. The residue was purified by prep-HPLC (Method 1) to afford the title compound as a white solid (0.003 g; 4% yield).

$^1$H NMR (d6-DMSO) δ: 11.01-11.10 (br. s, 1H); 9.18-9.40 (br. s, 1H); 8.13 (d, J=0.6 Hz, 1H); 8.01 (d, J=0.9 Hz, 1H); 7.69 (d, J=8.7 Hz, 1H); 7.56 (dd, J=1.4, 8.7 Hz, 1H), 7.45-7.48 (m, 2H); 7.32-7.35 (m, 2H); 4.50-4.57 (m, 1H); 4.27-4.34 (m, 1H); 3.88-3.94 (m, 2H); 3.04 (s, 3H); 2.72-2.79 (m, 1H); 2.19-2.25 (m, 1H); 1.54 (s, 3H); 0.98-1.01 (m, 2H); 0.88-0.92 (m, 2H).

MS (ESI, m/z): 561.93 [M+H$^+$] for $C_{25}H_{28}N_3O8PS$; $t_R$=0.65 min.

Example 49

(R)-(1-(4-((1-(4-(hydroxyamino)-3-methyl-3-(methylsulfonyl)-4-oxobutyl)-1H-indazol-5-yl)ethynyl)phenyl)cyclopropyl)methyl dimethylglycinate formate 49.i. (R)-(1-(4-((1-(3-methyl-3-(methylsulfonyl)-4-oxo-4-((((RS)-tetrahydro-2H-pyran-2-yl)oxy)amino)butyl)-1H-indazol-5-yl)ethynyl)phenyl)cyclopropyl)methyl dimethylglycinate Starting from the compound of Preparation I (0.223 g; 0.428 mmol) and the compound of Preparation AB (0.11 g; 0.428 mmol) and proceeding in analogy to Reference Example 5, step RE5.i, the title compound was obtained, after purification by CC (DCM-MeOH), as a brown oil (0.123 g; 44% yield).

$^1$H NMR (d6-DMSO) δ (mixture of stereoisomers): 11.49 (s, 0.5H); 11.43 (s, 0.5H); 8.14 (dd, J=0.7, 3.4 Hz, 1H); 8.01 (d, J=0.8 Hz, 1H); 7.67-7.72 (m, 1H); 7.54-7.58 (m, 1H); 7.46-7.50 (m, 2H); 7.31-7.34 (m, 2H); 4.97-4.99 (m, 1H); 4.50-4.59 (m, 1H); 4.32-4.42 (m, 1H); 4.24 (s, 2H); 4.14-4.20 (m, 0.5H); 4.02-4.11 (m, 0.5H); 3.51-3.58 (m, 1H); 3.14 (s, 2H); 3.05 (s, 1.5H); 3.04 (s, 1.5H); 2.70-2.81 (m, 1H); 2.22-2.30 (m, 1H); 2.19 (s, 6H); 1.67-1.74 (m, 3H); 1.50-1.59 (m, 6H); 1.00-1.03 (m, 2H), 0.94-0.97 (m, 2H).

MS (ESI, m/z): 651.97 [M+H+] for $C_{34}H_{42}N_4O_7S$; $t_R$=0.76 min.

49.ii. (R)-(1-(4-((1-(4-(hydroxyamino)-3-methyl-3-(methylsulfonyl)-4-oxobutyl)-1H-indazol-5-yl)ethynyl)phenyl)cyclopropyl)methyl dimethylglycinate formate To a mixture of intermediate 49.i (0.12 g; 0.19 mmol) in water (0.4 mL) was added TFA (0.7 mL; 9 mmol). The reaction was stirred at rt for 30 min and directly purified by prep-HPLC (Method 1) to afford a yellow solid (0.014 g; 12% yield).

$^1$H NMR (d6-DMSO) δ: 11.05 (s, 1H); 9.28 (s, 1H); 8.14 (m, 2H); 8.01 (s, 1H); 7.70 (d, J=8.8 Hz, 1H); 7.55 (dd, J=1.4, 8.8 Hz, 1H); 7.49 (d, J=8.4 Hz, 2H); 7.35 (d, J=8.4 Hz, 2H); 4.50-4.58 (m, 1H); 4.28-4.39 (overlapped m, 1H); 4.36 (s, 2H); 3.99 (s, 2H); 3.04 (s, 3H); 2.60-2.81 (overlapped m, 1H); 2.68 (s, 6H); 2.16-2.27 (m, 1H); 1.55 (s, 3H); 1.04-1.08 (m, 2H); 0.97-1.01 (m, 2H).

MS (ESI, m/z): 567 [M+H+] for $C_{30}H_{36}N_4O_8S$; $t_R$=0.67 min.

Example 50

(R)-4-(5-((R)-6,7-dihydroxyhepta-1,3-diyn-1-yl)-1H-indazol-1-yl)-N-hydroxy-2-methyl-2-(methylsulfonyl)butanamide Starting from the compound of Preparation J (0.092 g; 0.22 mmol) and the compound of Preparation AC (0.119 g; 0.665 mmol) and proceeding successively in analogy to Example 31, step 31.i (25% yield) and Reference Example 1, step RE1.iii (18% yield), the title compound was obtained, after purification by prep-HPLC (Method 2), as a brown solid (0.004 g).

$^1$H NMR (d6-DMSO) δ: 8.13 (s, 1H); 8.04 (s, 1H); 7.69 (d, J=8.8 Hz, 1H); 7.53 (d, J=8.8 Hz, 1H); 5.05 (br. s, 1H); 4.71 (br. s, 1H); 4.49-4.57 (m, 1H); 4.28-4.36 (m, 1H); 3.60-3.67 (m, 1H); 3.23-3.43 (overlapped m, 2H); 3.03 (s, 3H); 2.68-2.75 (m, 1H); 2.43-2.65 (overlapped m, 2H); 2.14-2.23 (m, 1H); 1.53 (s, 3H).

MS (ESI, m/z): 434.94 [M+H$^+$] for $C_{20}H_{23}N_3O_6S$; $t_R$=0.59 min.

Example 51

(R)-4-(5-(((1s,3R,4S)-3,4-dihydroxycyclopentyl) buta-1,3-diyn-1-yl)-1H-indazol-1-yl)-N-hydroxy-2-methyl-2-(methylsulfonyl)butanamide Starting from the compound of Preparation J (0.099 g; 0.237 mmol) and the compound of Preparation AD (0.07 g; 0.287 mmol) and proceeding successively in analogy to Example 31, step 31.i (72% yield) and Example 49, step 49.ii (12% yield), the title compound was obtained, after purification by prep-HPLC (Method 1), as a yellow solid (0.009 g).

$^1$H NMR (d6-DMSO) δ: 11.04 (br. s, 1H); 9.30 (br. s, 1H); 8.13 (s, 1H); 8.02 (s, 1H); 7.67 (d, J=8.8 Hz, 1H); 7.51 (dd, J=1.1, 8.8 Hz, 1H); 4.49-4.60 (m, 3H); 4.26-4.34 (m, 1H); 3.96 (s, 2H); 3.12-3.21 (m, 1H); 3.02 (s, 3H); 2.69-2.78 (m, 1H); 2.16-2.24 (m, 1H); 1.89-1.99 (m, 2H); 1.75-1.83 (m, 2H); 1.53 (s, 3H).

MS (ESI, m/z): 459.96 [M+H$^+$] for $C_{22}H_{25}N_3O_6S$; $t_R$=0.64 min.

Example 52

(R)—N-hydroxy-4-(5-((4-(1-(hydroxymethyl)cyclopropyl)phenyl)ethynyl)-1H-indazol-1-yl)-2-methyl-2-(methylsulfonyl)butanamide Starting from the compound of Preparation J (0.15 g; 0.358 mmol) and the compound of Preparation AE (0.112 g; 0.41 mmol) and proceeding successively in analogy to Reference Example 5, step RE5.i (90% yield) and Reference Example 1, step RE1.iii (36% yield), the title compound was obtained, after purification by prep-HPLC (Method 2), as a yellow solid (0.056 g).

$^1$H NMR (d6-DMSO) δ: 11.06 (s, 1H); 9.29 (s, 1H); 8.14 (s, 1H); 8.01 (s, 1H); 7.70 (d, J=8.7 Hz, 1H); 7.56 (d, J=10.1 Hz, 1H); 7.47 (d, J=8.4 Hz, 2H); 7.34 (d, J=8.4 Hz, 2H); 4.74 (t, J=5.6 Hz, 1H); 4.50-4.59 (m, 1H); 4.27-4.37 (m, 1H); 3.57 (d, J=5.5 Hz, 2H); 3.05 (s, 3H); 2.72-2.82 (m, 1H); 2.18-2.28 (m, 1H); 1.55 (s, 3H); 0.86-0.92 (m, 2H); 0.76-0.82 (m, 2H).

MS (ESI, m/z): 482.02 [M+H$^+$] for $C_{25}H_{27}N_3O_5S$; $t_R$=0.76 min.

Example 53

(R)—N-hydroxy-4-(5-((3-(hydroxymethyl)bicyclo[1.1.1]pentan-1-yl)buta-1,3-diyn-1-yl)-1H-indazol-1-yl)-2-methyl-2-(methylsulfonyl)butanamide Starting from the compound of Preparation J (0.061 g; 0.145 mmol) and the compound of Preparation AF (0.067 g; 0.145 mmol) and proceeding successively in analogy to Example 31, step 31.i (95% yield) and Example 49, step 49.ii (22% yield), the title compound was obtained, after purification by prep-HPLC (Method 2), as a brown foam (0.014 g).

$^1$H NMR (d6-DMSO) δ: 8.13 (s, 1H); 8.04 (s, 1H); 7.71 (d, J=8.7 Hz, 1H); 7.51 (d, J=8.7 Hz, 1H); 4.57-4.65 (m, 1H); 4.46-4.56 (m, 1H); 4.31-4.44 (m, 1H); 3.14-3.21 (m, 2H); 3.03 (s, 3H); 2.58-2.75 (m, 1H); 2.07-2.20 (m, 1H); 1.99 (s, 6H); 1.48 (s, 3H).

MS (ESI, m/z): 456.0 [M+H$^+$] for $C_{23}H_{25}N_3O_5S$; $t_R$=0.74 min.

Example 54

(R)-4-(5-((1-(aminomethyl)cyclopropyl)buta-1,3-diyn-1-yl)-1H-indazol-1-yl)-N-hydroxy-2-methyl-2-(methylsulfonyl)butanamide Starting from the compound of Preparation J (0.14 g; 0.334 mmol) and the compound of Preparation AG (0.137 g; 0.5 mmol) and proceeding successively in analogy to Example 31, step 31.i (64% yield) and Example 49, step 49.ii (7% yield), the title compound was obtained, after purification by prep-HPLC (Method 2), as a beige solid (0.006 g).

$^1$H NMR (d6-DMSO) δ: 8.14 (s, 1H); 8.03 (s, 1H); 7.68 (d, J=8.7 Hz, 1H); 7.52 (d, J=8.7 Hz, 1H); 4.48-4.62 (m, 1H); 4.26-4.37 (m, 1H); 3.03 (s, 3H); 2.67-2.79 (m, 1H); 2.61-2.67 (m, 2H); 2.14-2.26 (m, 1H); 1.54 (s, 3H); 0.84-0.98 (m, 4H).

MS (ESI, m/z): 456.0 [M+H+] for $C_{21}H_{24}N_4O_4S$; $t_R$=0.57 min.

Besides, the racemic mixtures of Reference Examples 1 to 13 can be separated into their enantiomers using, for example, chiral HPLC. Thus the following further invention compounds or salts would be obtained:

(R)-4-(5-(but-2-yn-1-yloxy)-1H-indol-1-yl)-N-hydroxy-2-methyl-2-(methylsulfonyl)butanamide;

(R)-4-(5-(2-fluoro-3-methoxyphenyl)-1H-indazol-1-yl)-N-hydroxy-2-methyl-2-(methylsulfonyl)butanamide;

(R)-(E)-N-hydroxy-2-methyl-2-(methylsulfonyl)-4-(5-styryl-1H-indazol-1-yl)butanamide;

(R)—N-hydroxy-2-methyl-2-(methylsulfonyl)-4-(5-phenethyl-1H-indazol-1-yl)butanamide;

(R)—N-hydroxy-2-methyl-2-(methylsulfonyl)-4-(5-((4-(morpholinomethyl)phenyl)ethynyl)-1H-indazol-1-yl)butanamide 4-toluenesulfonic acid salt;

(R)-4-(5-((4-aminophenyl)ethynyl)-1H-indazol-1-yl)-N-hydroxy-2-methyl-2-(methylsulfonyl)butanamide;

(R)—N-hydroxy-2-methyl-2-(methylsulfonyl)-4-(5-(4-(trifluoromethoxy)phenyl)-1H-indazol-1-yl)butanamide;

(R)-4-(5-(4-(2H-1,2,3-triazol-2-yl)phenyl)-1H-indol-1-yl)-N-hydroxy-2-methyl-2-(methylsulfonyl)butanamide formate;

(R)—N-hydroxy-2-methyl-2-(methylsulfonyl)-4-(5-(4-(trifluoromethoxy)phenyl)-1H-indol-1-yl)butanamide;

(R)-4-(5-(2-fluoro-4-(methylthio)phenyl)-1H-indol-1-yl)-N-hydroxy-2-methyl-2-(methylsulfonyl)butanamide;

(R)-4-(6-fluoro-5-(2-fluoro-4-methoxyphenyl)-1H-indol-1-yl)-N-hydroxy-2-methyl-2-(methylsulfonyl)butanamide;

(R)-4-(4-fluoro-5-(2-fluoro-4-methoxyphenyl)-1H-indol-1-yl)-N-hydroxy-2-methyl-2-(methylsulfonyl)butanamide; and (R)-4-(4-fluoro-5-((4-(3-hydroxyoxetan-3-yl)phenyl)ethynyl)-1H-indol-1-yl)-N-hydroxy-2-methyl-2-(methylsulfonyl)butanamide.

Pharmacological Properties of the Invention Compounds
In Vitro Assays
Bacterial Growth Minimal Inhibitory Concentrations:
Experimental Methods:

Minimal Inhibitory Concentrations (MICs; mg/L) were determined in cation-adjusted Mueller-Hinton Broth by a microdilution method following the description given in "*Methods for Dilution Antimicrobial Susceptibility Tests for Bacteria that Grow Aerobically*", Approved standard, 7th ed., Clinical and Laboratory Standards Institute (CLSI) Document M7-A7, Wayne, Pa., USA (2006).

Results:

All Example compounds were tested against several Gram-positive and Gram-negative bacteria. Typical antibacterial test results are given in Table 1 hereafter (MICs in mg/L). *K. pneumoniae* A-651 and *Acinetobacter baumannii* T6474 are multiply-resistant strains (in particular quinolone-resistant), while *E. coli* ATCC25922 and *P. aeruginosa* ATCC27853 are quinolone-sensitive strains.

TABLE 1

| Example No. | MIC for E. coli ATCC25922 | MIC for P. aeruginosa ATCC27853 | MIC for A. Baumannii T6474 | MIC for K. Pneumoniae A-651 |
|---|---|---|---|---|
| RE1 | 8 | 16 | 16 | 16 |
| RE2 | 8 | 16 | 32 | 16 |
| RE3 | 0.25 | 16 | 0.25 | 1 |
| RE4 | 2 | 8 | 8 | 0.5 |
| RE5 | 0.5 | 16 | 32 | 0.5 |
| RE6 | 0.25 | 8 | 1 | 0.5 |
| RE7 | 4 | 8 | 8 | 1 |
| RE8 | 0.25 | 8 | 0.5 | ≤0.063 |
| RE9 | 4 | 8 | 2 | 2 |
| RE10 | 2 | 8 | 4 | 0.5 |
| RE11 | 1 | 8 | 4 | 2 |
| RE12 | 2 | 2 | 2 | 4 |
| RE13 | 0.25 | 2 | 4 | 0.5 |
| 1 | ≤0.063 | 4 | 16 | 0.25 |
| 2 | 0.125 | 2 | 8 | 2 |
| 3 | 0.25 | 1 | 1 | 1 |
| 4 | 0.125 | 2 | 0.125 | ≤0.063 |
| 5 | 1 | 2 | >32 | 1 |
| 6 | ≤0.063 | 2 | 0.125 | 0.125 |
| 7 | 0.5 | 2 | 32 | 1 |
| 8 | 0.125 | 2 | 0.25 | 0.25 |
| 9 | ≤0.063 | 1 | 0.125 | 0.125 |
| 10 | 0.125 | 1 | 0.125 | 0.25 |
| 11 | 0.5 | 1 | 16 | 0.25 |
| 12 | 0.25 | 1 | 0.25 | 0.25 |
| 13 | 0.25 | 1 | 8 | 0.25 |
| 14 | ≤0.063 | 1 | 0.125 | 0.25 |
| 15 | 0.5 | 1 | 0.25 | 0.5 |
| 16 | ≤0.063 | 1 | 0.25 | 0.125 |
| 17 | ≤0.063 | 0.5 | 16 | 0.125 |
| 18 | ≤0.063 | 0.5 | 16 | ≤0.063 |
| 19 | 0.125 | 1 | ≤0.063 | 0.25 |
| 20 | ≤0.063 | 1 | ≤0.063 | 0.25 |
| 21 | 1 | 1 | 0.5 | 1 |
| 22 | 0.5 | 1 | 0.5 | 1 |
| 23 | 0.125 | 1 | 0.125 | 0.5 |
| 24 | 1 | 1 | >32 | 4 |
| 25 | 0.25 | 2 | 0.5 | 0.5 |
| 26 | ≤0.063 | 0.5 | 2 | 0.125 |
| 27 | 0.25 | 2 | 0.125 | 0.5 |
| 28 | 1 | 4 | 0.5 | 2 |
| 29 | 0.25 | 2 | 0.5 | 0.5 |
| 30 | 0.25 | 1 | 0.125 | 0.5 |
| 31 | ≤0.063 | 0.5 | 1 | ≤0.063 |
| 32 | 0.125 | 2 | 16 | 0.25 |
| 33 | 0.125 | 2 | 0.125 | 0.25 |
| 34 | 0.25 | 1 | 16 | 0.5 |
| 35 | ≤0.063 | 2 | 0.25 | 0.25 |
| 36 | ≤0.063 | 1 | ≤0.063 | 0.125 |
| 37 | ≤0.063 | 1 | ≤0.063 | 0.125 |
| 38 | 0.5 | 1 | 32 | 1 |

TABLE 1-continued

| Example No. | MIC for E. coli ATCC25922 | MIC for P. aeruginosa ATCC27853 | MIC for A. Baumannii T6474 | MIC for K. Pneumoniae A-651 |
|---|---|---|---|---|
| 39 | 0.25 | 2 | 32 | 0.5 |
| 40 | 0.5 | 4 | 0.5 | 1 |
| 41 | 0.125 | 1 | 16 | 0.125 |
| 42 | ≤0.063 | 0.5 | 32 | 0.25 |
| 43 | 0.5 | 1 | 16 | 0.5 |
| 44 | 0.125 | 2 | 8 | 0.25 |
| 45 | ≤0.063 | 1 | 8 | 0.25 |
| 46 | ≤0.063 | 1 | >32 | 0.125 |
| 47 | ≤0.063 | 2 | 0.25 | 0.25 |
| 49 | 1 | 16 | 2 | 2 |
| 50 | 4 | 2 | 32 | 4 |
| 51 | 0.5 | 1 | 4 | 1 |
| 52 | ≤0.063 | 2 | 0.125 | 0.25 |
| 53 | 0.125 | 1 | 1 | 0.25 |
| 54 | 8 | 8 | >32 | 16 |
| Cipro | 0.5 | >32 | >8 | >32 |

The compounds of Examples 48 and 49 were tested against wild-type *E. coli* A-1261 in the absence of alkaline phosphatase or esterase, in the presence of an alkaline phosphatase and in the presence of an esterase. The corresponding antibacterial test results are given in Table 2 hereafter (MICs in mg/L).

TABLE 2

| | MIC for E. coli A-1261 | | |
|---|---|---|---|
| Example No. | In the absence of alkaline phosphatase or esterase | In the presence of an alkaline phosphatase (2 i.U./mL) | In the presence of an esterase (10 i.U./mL) |
| 48 | 16 | 1 | 16 |
| 49 | 1 | 1 | 0.125 |

The invention claimed is:

1. A compound of formula I

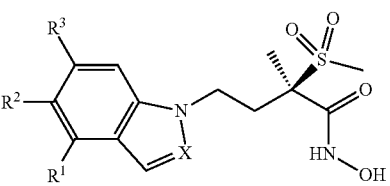

wherein
  X represents N or CH;
  $R^1$ represents H or halogen;
  $R^2$ represents $(C_3-C_4)$alkynyloxy or the group M;
  $R^3$ represents H or halogen;
  M is one of the groups $M^A$ and $M^B$ represented below

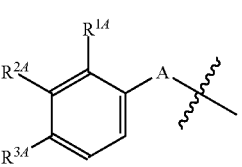

-continued

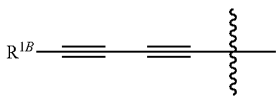
$M^B$ wherein A represents a bond, $CH_2CH_2$, $CH=CH$ or $C\equiv C$;
$R^{1A}$ represents H or halogen;
$R^{2A}$ represents H, $(C_1-C_3)$alkoxy or halogen;
$R^{3A}$ represents H, $(C_1-C_3)$alkoxy, hydroxy$(C_1-C_4)$alkoxy, $(C_1-C_3)$alkoxy$(C_2-C_3)$alkoxy, $(C_1-C_3)$thioalkoxy, trifluoromethoxy, amino, hydroxy$(C_1-C_4)$alkyl, 2-hydroxyacetamido, 1-aminocyclopropyl, 1-hydroxymethyl-cycloprop-1-yl, 1-((phosphonooxy)methyl)cyclopropyl, 1-(((dimethylglycyl)oxy)methyl)cyclopropyl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, 3-hydroxythietan-3-yl, morpholin-4-yl$(C_2-C_3)$alkoxy, morpholin-4-yl-$(C_1-C_2)$alkyl, oxazol-2-yl or [1,2,3]triazol-2-yl; and
$R^{1B}$ represents hydroxy$(C_1-C_3)$alkyl, dihydroxy$(C_1-C_4)$alkyl, amino$(C_1-C_3)$alkyl, (dimethylamino)methyl, 1-hydroxymethyl-cycloprop-1-yl, trans-2-(1,2-dihydroxyethyl)cycloprop-1-yl, 1-methyl-2-hydroxymethyl-cycloprop-1-yl, 2-(hydroxymethyl)-2-methylcyclopropyl, 1-aminomethyl-cycloprop-1-yl, trans-2-hydroxymethyl-cycloprop-1-yl, 1-fluoro-2-(hydroxymethyl)cyclopropyl, 2-fluoro-2-(hydroxymethyl)cyclopropyl, 1-(hydroxymethyl)cyclobutyl, 3-hydroxyoxetan-3-yl, 3-hydroxymethyl-oxetan-3-yl, 3-hydroxythietan-3-yl, 1-(2-hydroxyacetyl)azetidin-3-yl, 1-(2-aminoacetyl)azetidin-3-yl, 1-glycylazetidin-3-yl, 1-(2-amino-2-methylpropanoyl)azetidin-3-yl, 3-(2-aminoacetamido)cyclopentyl, trans-(cis-3,4-dihydroxy)-cyclopent-1-yl, 3-hydroxymethylbicyclo[1,1,1]pentan-1-yl, 3-hydroxymethylbicyclo[1,1,1]pentan-1-yl, piperidin-4-yl, 1-(2-hydroxyacetyl)piperidin-4-yl, 4-hydroxytetrahydro-2H-pyran-4-yl, 5-aminotetrahydro-2H-pyran-2-yl, (1s,3r)-(1-hydroxy-3-(hydroxymethyl)cyclobutyl)methyl or 3-hydroxyoxetan-3-ylmethyl;
or a salt thereof.

2. The compound of formula I according to claim 1, which is a compound of formula $I_P$

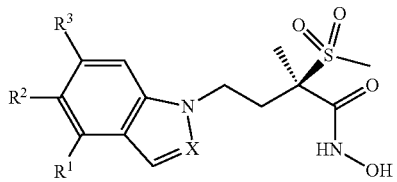
$I_P$ wherein
X represents N or CH;
$R^1$ represents H or halogen;
$R^2$ represents $(C_3-C_4)$alkynyloxy or the group M;
$R^3$ represents H or halogen;

M is one of the groups $M^A$ and $M^B$ represented below

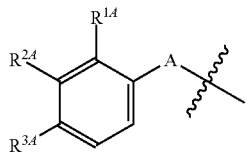
$M^A$

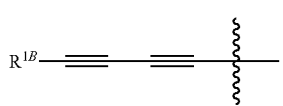
$M^B$ wherein A represents a bond, $CH_2CH_2$, $CH=CH$ or $C\equiv C$;
$R^{1A}$ represents H or halogen;
$R^{2A}$ represents H, $(C_1-C_3)$alkoxy or halogen;
$R^{3A}$ represents H, $(C_1-C_3)$alkoxy, hydroxy$(C_1-C_4)$alkoxy, $(C_1-C_3)$thioalkoxy, trifluoromethoxy, amino, hydroxy$(C_1-C_4)$alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-aminooxetan-3-yl, 3-hydroxythietan-3-yl, morpholin-4-yl$(C_2-C_3)$alkoxy, morpholin-4-yl-$(C_1-C_2)$alkyl, oxazol-2-yl or [1,2,3]triazol-2-yl; and
$R^{1B}$ represents 3-hydroxyoxetan-3-yl, 3-hydroxythietan-3-yl, hydroxy$(C_1-C_3)$alkyl, amino$(C_1-C_3)$alkyl, 1-hydroxymethyl-cycloprop-1-yl or trans-2-hydroxymethyl-cycloprop-1-yl;
or a salt thereof.

3. The compound of formula I according to claim 1, which is a compound of formula $I_{CE}$

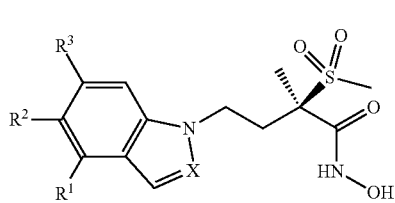
$I_{CE}$ wherein
X represents N or CH;
$R^1$ represents H or halogen;
$R^2$ represents $(C_3-C_4)$alkynyloxy or the group M;
$R^3$ represents H or halogen;
M is one of the groups $M^A$ and $M^B$ represented below

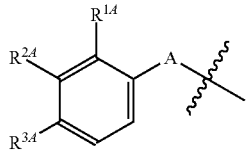
$M^A$

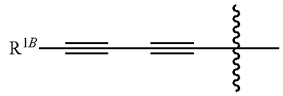
$M^B$ wherein A represents a bond, $CH_2CH_2$, CH=CH or C≡C;
$R^{1A}$ represents H or halogen;
$R^{2A}$ represents H or $(C_1-C_3)$alkoxy;
$R^{3A}$ represents H, $(C_1-C_3)$alkoxy, hydroxy$(C_1-C_4)$alkoxy, $(C_1-C_3)$thioalkoxy, trifluoromethoxy, amino, hydroxy $(C_1-C_4)$alkyl, 2-hydroxyacetamido, 1-hydroxymethyl-cycloprop-1-yl, 1-((phosphonooxy)methyl)cyclopropyl, 1-(((dimethylglycyl)oxy)methyl)cyclopropyl, trans-2-hydroxymethyl-cycloprop-1-yl, 1,2-dihydroxyethyl, 3-hydroxyoxetan-3-yl, 3-(hydroxy$(C_1-C_3)$alkyl)oxetan-3-yl, 3-hydroxythietan-3-yl, morpholin-4-yl-$(C_1-C_2)$alkyl or [1,2,3]triazol-2-yl; and
$R^{1B}$ represents 3-hydroxyoxetan-3-yl, 3-hydroxythietan-3-yl, hydroxy$(C_1-C_3)$alkyl, dihydroxy$(C_2-C_4)$alkyl, amino$(C_1-C_3)$alkyl, 1-hydroxymethyl-cycloprop-1-yl, 1-aminomethyl-cycloprop-1-yl, trans-2-hydroxymethyl-cycloprop-1-yl, trans-(cis-3,4-dihydroxy)-cyclopent-1-yl or 3-hydroxymethylbicyclo[1,1,1]pentan-1-yl;
or a salt thereof.

4. The compound of formula I according to claim 1, wherein $R^1$ represents H or fluorine, $R^3$ represents H or fluorine, $R^{1A}$ represents H or fluorine and $R^{2A}$ represents H; or a salt thereof.

5. The compound of formula I according to claim 1, wherein $R^2$ represents the group $M^A$;
or a salt thereof.

6. The compound of formula I according to claim 5, wherein A represents a bond;
or a salt thereof.

7. The compound of formula I according to claim 5, wherein A represents C≡C;
or a salt thereof.

8. The compound of formula I according to claim 7, wherein $R^{1A}$ represents H or fluorine, $R^{2A}$ represents H and $R^{3A}$ represents hydroxy$(C_1-C_4)$alkyl, trans-2-hydroxymethyl-cycloprop-1-yl, 1,2-dihydroxyethyl, 3-hydroxyoxetan-3-yl or 3-hydroxythietan-3-yl;
or a salt thereof.

9. The compound of formula I according to claim 1, wherein $R^2$ represents the group $M^B$;
or a salt thereof.

10. The compound of formula I according to claim 9, wherein $R^{1B}$ represents 3-hydroxyoxetan-3-yl, 2-aminoprop-2-yl, 1-hydroxymethyl-cycloprop-1-yl or trans-2-hydroxymethyl-cycloprop-1-yl;
or a salt thereof.

11. The compound of formula I according to claim 1, wherein the compound is:
(R)-4-(5-(but-2-yn-1-yloxy)-1H-indol-1-yl)-N-hydroxy-2-methyl-2-(methylsulfonyl)butanamide;
(R)-4-(5-(2-fluoro-3-methoxyphenyl)-1H-indazol-1-yl)-N-hydroxy-2-methyl-2-(methylsulfonyl)butanamide;
(R)-(E)-N-hydroxy-2-methyl-2-(methylsulfonyl)-4-(5-styryl-1H-indazol-1-yl)butanamide;
(R)—N-hydroxy-2-methyl-2-(methylsulfonyl)-4-(5-phenethyl-1H-indazol-1-yl)butanamide;
(R)—N-hydroxy-2-methyl-2-(methylsulfonyl)-4-(5-((4-(morpholinomethyl)phenyl)ethynyl)-1H-indazol-1-yl)butanamide 4-toluenesulfonic acid salt;
(R)-4-(5-((4-aminophenyl)ethynyl)-1H-indazol-1-yl)-N-hydroxy-2-methyl-2-(methylsulfonyl)butanamide;
(R)—N-hydroxy-2-methyl-2-(methylsulfonyl)-4-(5-(4-(trifluoromethoxy)phenyl)-1H-indazol-1-yl)butanamide;
(R)-4-(5-(4-(2H-1,2,3-triazol-2-yl)phenyl)-1H-indol-1-yl)-N-hydroxy-2-methyl-2-(methylsulfonyl)butanamide formate;
(R)—N-hydroxy-2-methyl-2-(methylsulfonyl)-4-(5-(4-(trifluoromethoxy)phenyl)-1H-indol-1-yl)butanamide;
(R)-4-(5-(2-fluoro-4-(methylthio)phenyl)-1H-indol-1-yl)-N-hydroxy-2-methyl-2-(methylsulfonyl)butanamide;
(R)-4-(6-fluoro-5-(2-fluoro-4-methoxyphenyl)-1H-indol-1-yl)-N-hydroxy-2-methyl-2-(methylsulfonyl)butanamide;
(R)-4-(4-fluoro-5-(2-fluoro-4-methoxyphenyl)-1H-indol-1-yl)-N-hydroxy-2-methyl-2-(methylsulfonyl)butanamide;
(R)-4-(4-fluoro-5-((4-(3-hydroxyoxetan-3-yl)phenyl)ethynyl)-1H-indol-1-yl)-N-hydroxy-2-methyl-2-(methylsulfonyl)butanamide;
(R)-4-(5-(2-fluoro-4-(methylthio)phenyl)-1H-indazol-1-yl)-N-hydroxy-2-methyl-2-(methylsulfonyl)butanamide;
(R)-4-(5-(2-fluoro-4-methoxyphenyl)-1H-indol-1-yl)-N-hydroxy-2-methyl-2-(methylsulfonyl)butanamide;
(R)-4-(5-(2-fluoro-4-methoxyphenyl)-1H-indazol-1-yl)-N-hydroxy-2-methyl-2-(methylsulfonyl)butanamide;
(R)—N-hydroxy-4-(5-((4-(hydroxymethyl)phenyl)ethynyl)-1H-indazol-1-yl)-2-methyl-2-(methylsulfonyl)butanamide;
(R)—N-hydroxy-4-(5-((3-hydroxyoxetan-3-yl)buta-1,3-diyn-1-yl)-1H-indazol-1-yl)-2-methyl-2-(methylsulfonyl)butanamide;
(R)-4-(5-(4-(2H-1,2,3-triazol-2-yl)phenyl)-1H-indazol-1-yl)-N-hydroxy-2-methyl-2-(methylsulfonyl)butanamide;
(R)—N-hydroxy-4-(5-(5-hydroxy-5-methylhexa-1,3-diyn-1-yl)-1H-indazol-1-yl)-2-methyl-2-(methylsulfonyl)butanamide;
(R)—N-hydroxy-4-(5-((4-(2-hydroxypropan-2-yl)phenyl)ethynyl)-1H-indazol-1-yl)-2-methyl-2-(methylsulfonyl)butanamide;
(R)—N-hydroxy-4-(5-((4-(hydroxymethyl)phenyl)ethynyl)-1H-indol-1-yl)-2-methyl-2-(methylsulfonyl)butanamide;
(R)—N-hydroxy-4-(5-((4-(3-hydroxyoxetan-3-yl)phenyl)ethynyl)-1H-indol-1-yl)-2-methyl-2-(methylsulfonyl)butanamide;
(R)—N-hydroxy-4-(5-((3-hydroxyoxetan-3-yl)buta-1,3-diyn-1-yl)-1H-indol-1-yl)-2-methyl-2-(methylsulfonyl)butanamide;
(R)—N-hydroxy-4-(5-((4-(3-hydroxyoxetan-3-yl)phenyl)ethynyl)-1H-indazol-1-yl)-2-methyl-2-(methylsulfonyl)butanamide;
(R)—N-hydroxy-4-(5-((3-hydroxythietan-3-yl)buta-1,3-diyn-1-yl)-1H-indazol-1-yl)-2-methyl-2-(methylsulfonyl)butanamide;
(R)—N-hydroxy-4-(5-((4-(2-hydroxyethyl)phenyl)ethynyl)-1H-indazol-1-yl)-2-methyl-2-(methylsulfonyl)butanamide;
(R)-4-(6-fluoro-5-((4-(3-hydroxyoxetan-3-yl)phenyl)ethynyl)-1H-indol-1-yl)-N-hydroxy-2-methyl-2-(methylsulfonyl)butanamide;
(R)—N-hydroxy-4-(5-((4-((R)-1-hydroxyethyl)phenyl)ethynyl)-1H-indazol-1-yl)-2-methyl-2-(methylsulfonyl)butanamide;
(R)—N-hydroxy-4-(5-(((1S,2S)-2-(hydroxymethyl)cyclopropyl)buta-1,3-diyn-1-yl)-1H-indol-1-yl)-2-methyl-2-(methylsulfonyl)butanamide;

(R)—N-hydroxy-4-(5-(((1R,2R)-2-(hydroxymethyl)cyclopropyl)buta-1,3-diyn-1-yl)-1H-indol-1-yl)-2-methyl-2-(methylsulfonyl)butanamide;
(R)—N-hydroxy-4-(5-((4-((1S,2S)-2-(hydroxymethyl)cyclopropyl)phenyl)ethynyl)-1H-indazol-1-yl)-2-methyl-2-(methylsulfonyl)butanamide;
(R)—N-hydroxy-4-(5-((4-((1R,2R)-2-(hydroxymethyl)cyclopropyl)phenyl)ethynyl)-1H-indazol-1-yl)-2-methyl-2-(methylsulfonyl)butanamide;
(R)-4-(5-((4-((R)-1,2-dihydroxyethyl)phenyl)ethynyl)-1H-indazol-1-yl)-N-hydroxy-2-methyl-2-(methylsulfonyl)butanamide;
(R)-4-(5-((4-((S)-1,2-dihydroxyethyl)phenyl)ethynyl)-1H-indazol-1-yl)-N-hydroxy-2-methyl-2-(methylsulfonyl)butanamide;
(R)—N-hydroxy-4-(5-((4-((S)-1-hydroxyethyl)phenyl)ethynyl)-1H-indazol-1-yl)-2-methyl-2-(methylsulfonyl)butanamide;
(R)-4-(5-(5-amino-5-methylhexa-1,3-diyn-1-yl)-1H-indazol-1-yl)-N-hydroxy-2-methyl-2-(methylsulfonyl)butanamide;
(R)—N-hydroxy-4-(5-((4-(1-(hydroxymethyl)cyclopropyl)phenyl)ethynyl)-1H-indol-1-yl)-2-methyl-2-(methylsulfonyl)butanamide;
(R)—N-hydroxy-4-(5-(((1S,2S)-2-(hydroxymethyl)cyclopropyl)buta-1,3-diyn-1-yl)-1H-indazol-1-yl)-2-methyl-2-(methylsulfonyl)butanamide;
(R)—N-hydroxy-4-(5-((4-(2-hydroxyethoxy)phenyl)ethynyl)-1H-indazol-1-yl)-2-methyl-2-(methylsulfonyl)butanamide;
(R)—N-hydroxy-4-(5-((4-(2-hydroxyacetamido)phenyl)ethynyl)-1H-indazol-1-yl)-2-methyl-2-(methylsulfonyl)butanamide;
(R)—N-hydroxy-4-(5-((4-(2-hydroxypropan-2-yl)phenyl)ethynyl)-1H-indol-1-yl)-2-methyl-2-(methylsulfonyl)butanamide;
(R)-4-(4-fluoro-5-((4-(3-hydroxyoxetan-3-yl)phenyl)ethynyl)-1H-indazol-1-yl)-N-hydroxy-2-methyl-2-(methylsulfonyl)butanamide;
(R)-4-(4-fluoro-5-(((1S,2S)-2-(hydroxymethyl)cyclopropyl)buta-1,3-diyn-1-yl)-1H-indazol-1-yl)-N-hydroxy-2-methyl-2-(methylsulfonyl) butanamide;
(R)—N-hydroxy-4-(5-((3-hydroxythietan-3-yl)buta-1,3-diyn-1-yl)-1H-indol-1-yl)-2-methyl-2-(methylsulfonyl)butanamide;
(R)—N-hydroxy-4-(5-((4-((1S,2S)-2-(hydroxymethyl)cyclopropyl)phenyl)ethynyl)-1H-indol-1-yl)-2-methyl-2-(methylsulfonyl)butanamide;
(R)—N-hydroxy-4-(5-((1-(hydroxymethyl)cyclopropyl)buta-1,3-diyn-1-yl)-1H-indazol-1-yl)-2-methyl-2-(methylsulfonyl)butanamide;
(R)—N-hydroxy-4-(5-((4-((S)-1-hydroxyethyl)phenyl)ethynyl)-1H-indol-1-yl)-2-methyl-2-(methylsulfonyl)butanamide;
(R)-4-(4-fluoro-5-((4-(2-hydroxyethyl)phenyl)ethynyl)-1H-indazol-1-yl)-N-hydroxy-2-methyl-2-(methylsulfonyl)butanamide;
(R)-4-(4-fluoro-5-((4-((R)-1-hydroxyethyl)phenyl)ethynyl)-1H-indazol-1-yl)-N-hydroxy-2-methyl-2-(methylsulfonyl)butanamide;
(R)-4-(4-fluoro-5-((3-hydroxyoxetan-3-yl)buta-1,3-diyn-1-yl)-1H-indazol-1-yl)-N-hydroxy-2-methyl-2-(methylsulfonyl)butanamide;
(R)-4-(4-fluoro-5-((1-(hydroxymethyl)cyclopropyl)buta-1,3-diyn-1-yl)-1H-indazol-1-yl)-N-hydroxy-2-methyl-2-(methylsulfonyl) butanamide;
(R)-4-(4-fluoro-5-((4-(3-(hydroxymethyl)oxetan-3-yl)phenyl)ethynyl)-1H-indazol-1-yl)-N-hydroxy-2-methyl-2-(methylsulfonyl) butanamide;
(R)-4-(6-fluoro-5-((2-(hydroxymethyl)cyclopropyl)buta-1,3-diyn-1-yl)-1H-indol-1-yl)-N-hydroxy-2-methyl-2-(methylsulfonyl)butanamide;
(R)—N-hydroxy-4-(5-(((1R,2R)-2-(hydroxymethyl)cyclopropyl)buta-1,3-diyn-1-yl)-1H-indazol-1-yl)-2-methyl-2-(methylsulfonyl)butanamide;
(R)-4-(5-((2-fluoro-4-(hydroxymethyl)phenyl)ethynyl)-1H-indol-1-yl)-N-hydroxy-2-methyl-2-(methylsulfonyl)butanamide;
(R)-4-(5-((4-((R)-1,2-dihydroxyethyl)phenyl)ethynyl)-1H-indol-1-yl)-N-hydroxy-2-methyl-2-(methylsulfonyl)butanamide;
(R)—N-hydroxy-4-(5-((4-(2-hydroxyethyl)phenyl)ethynyl)-1H-indol-1-yl)-2-methyl-2-(methylsulfonyl)butanamide;
(R)-4-(6-fluoro-5-(((1S,2S)-2-(hydroxymethyl)cyclopropyl)buta-1,3-diyn-1-yl)-1H-indazol-1-yl)-N-hydroxy-2-methyl-2-(methylsulfonyl) butanamide;
(R)-4-(6-fluoro-5-((4-(2-hydroxyethyl)phenyl)ethynyl)-1H-indazol-1-yl)-N-hydroxy-2-methyl-2-(methylsulfonyl)butanamide;
(R)-(1-(4-((1-(4-(hydroxyamino)-3-methyl-3-(methylsulfonyl)-4-oxobutyl)-1H-indazol-5-yl)ethynyl)phenyl)cyclopropyl)methyl dihydrogen phosphate;
(R)-(1-(4-((1-(4-(hydroxyamino)-3-methyl-3-(methylsulfonyl)-4-oxobutyl)-1H-indazol-5-yl)ethynyl)phenyl)cyclopropyl)methyl dimethylglycinate;
(R)-4-(5-((R)-6,7-dihydroxyhepta-1,3-diyn-1-yl)-1H-indazol-1-yl)-N-hydroxy-2-methyl-2-(methylsulfonyl) butanamide;
(R)-4-(5-(((1s,3R,4S)-3,4-dihydroxycyclopentyl)buta-1,3-diyn-1-yl)-1H-indazol-1-yl)-N-hydroxy-2-methyl-2-(methylsulfonyl)butanamide;
(R)—N-hydroxy-4-(5-((4-(1-(hydroxymethyl)cyclopropyl)phenyl)ethynyl)-1H-indazol-1-yl)-2-methyl-2-(methylsulfonyl)butanamide;
(R)—N-hydroxy-4-(5-((3-(hydroxymethyl)bicyclo[1.1.1]pentan-1-yl)buta-1,3-diyn-1-yl)-1H-indazol-1-yl)-2-methyl-2-(methylsulfonyl)butanamide; or
(R)-4-(5-((1-(aminomethyl)cyclopropyl)buta-1,3-diyn-1-yl)-1H-indazol-1-yl)-N-hydroxy-2-methyl-2-(methylsulfonyl)butanamide;

or a salt thereof.

12. The compound of formula I according to claim 1, or a pharmaceutically acceptable salt thereof, wherein the compound is formulated as a medicament.

13. A pharmaceutical composition comprising, as active principle, the compound of formula I according to claim 1, or a pharmaceutically acceptable salt thereof, and at least one therapeutically inert excipient.

14. A method of treating or preventing a bacterial infection comprising administering to a subject in need thereof the compound according to claim 1.

15. The method according to claim 14, wherein the bacterial infection is a Gram-negative bacterial infection.

* * * * *